(12) United States Patent
Flentie et al.

(10) Patent No.: US 12,312,632 B2
(45) Date of Patent: *May 27, 2025

(54) SYSTEMS AND METHODS FOR PERFORMING ANTIMICROBIAL SUSCEPTIBILITY TESTING

(71) Applicant: SeLux Diagnostics, Inc., Charlestown, MA (US)

(72) Inventors: Kelly Flentie, Charlestown, MA (US); Eric Stern, Charlestown, MA (US)

(73) Assignee: SeLux Diagnostics, Inc., Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/499,761

(22) Filed: Nov. 1, 2023

(65) Prior Publication Data

US 2024/0102074 A1 Mar. 28, 2024

Related U.S. Application Data

(63) Continuation of application No. 17/004,848, filed on Aug. 27, 2020, now Pat. No. 11,845,976.

(60) Provisional application No. 62/892,305, filed on Aug. 27, 2019.

(51) Int. Cl.
*C12Q 1/18* (2006.01)

(52) U.S. Cl.
CPC ..................... *C12Q 1/18* (2013.01)

(58) Field of Classification Search
None
See application file for complete search history.

(56) References Cited

U.S. PATENT DOCUMENTS

| | | |
|---|---|---|
| 3,798,320 A | 3/1974 | Cameron et al. |
| 4,169,096 A | 9/1979 | Kawaguchi et al. |
| 4,565,790 A | 1/1986 | Hemmila et al. |
| 4,647,536 A | 3/1987 | Mosbach et al. |
| 4,808,541 A | 2/1989 | Mikola et al. |
| 4,927,923 A | 5/1990 | Mathis et al. |
| 5,457,185 A | 10/1995 | Lehn et al. |
| 5,489,401 A | 2/1996 | Freeman |
| 5,512,493 A | 4/1996 | Mathis et al. |
| 5,527,684 A | 6/1996 | Mabile et al. |
| 5,627,074 A | 5/1997 | Mathis et al. |
| 5,665,554 A | 9/1997 | Reeve et al. |
| 5,695,946 A | 12/1997 | Benjamin et al. |
| 6,284,470 B1 | 9/2001 | Bitner et al. |
| 6,385,272 B1 | 5/2002 | Takahashi |
| 6,844,028 B2 | 1/2005 | Mao et al. |
| 7,341,841 B2 | 3/2008 | Metzger et al. |
| 7,629,029 B2 | 12/2009 | Mao et al. |
| 7,868,144 B2 | 1/2011 | Diller et al. |
| 8,178,602 B2 | 5/2012 | Mao et al. |
| 8,895,255 B1 | 11/2014 | Goldberg et al. |
| 9,834,808 B2 | 12/2017 | Stern et al. |
| 11,845,976 B2 * | 12/2023 | Flentie ............... C12Q 1/18 |
| 2004/0029254 A1 | 2/2004 | Stamm et al. |
| 2012/0149599 A1 | 6/2012 | Williams et al. |
| 2013/0217063 A1 | 8/2013 | Metzger et al. |
| 2014/0278136 A1 | 9/2014 | Shamsheyeva et al. |
| 2014/0323340 A1 | 10/2014 | Goldberg et al. |
| 2014/0363817 A1 | 12/2014 | Dukan et al. |
| 2015/0064703 A1 | 3/2015 | Super et al. |
| 2015/0337351 A1 | 11/2015 | Metzger |
| 2016/0010138 A1 | 1/2016 | Shamsheyeva et al. |
| 2017/0211121 A1 | 7/2017 | Stern et al. |
| 2018/0179572 A1 | 6/2018 | Stern et al. |
| 2018/0291419 A1 | 10/2018 | Richards et al. |
| 2020/0149086 A1 | 5/2020 | Stern et al. |

FOREIGN PATENT DOCUMENTS

| | | |
|---|---|---|
| EP | 0064484 A2 | 11/1982 |
| EP | 0139675 A1 | 5/1985 |
| EP | 3202885 A1 | 8/2017 |
| WO | 8403698 A1 | 9/1984 |
| WO | 2016015027 A1 | 1/2016 |
| WO | 2017015145 A2 | 1/2017 |
| WO | 2017127684 A1 | 7/2017 |
| WO | 2018119439 A1 | 6/2018 |

OTHER PUBLICATIONS

International Search Report and Written Opinion for International application No. PCT/US2020/048242, mailed on Jan. 22, 2021, 17 pages.
Partial Supplementary European Search Report for EP Patent Application No. 20856302.3, mailed Mar. 14, 2024.
Weibull, E., et al., "Bacterial Nanoscale Cultures for Phenotypic Multiplexed Antibiotic Susceptibility Testing", Journal of clinical microbiology, 52(9):3310-3317, Jul. 2, 2014.
Dorey, L., et al., "Activity of florfenicol forActinobacillus pleuropneumoniaeandPasteurella multocidausing standardised versus non-standardised methodology", Veterinary Journal, 218:65-70, 16 Nov. 16, 2016.
Bonnefoy, A., et al., "In vitro activity of AVE1330A, an innovative broad-spectrum non-.beta.-lactam .beta.-lactamase inhibitor", Journal of Antimicrobial Chemotherapy, 54(2):410-417, Aug. 1, 2004.

* cited by examiner

*Primary Examiner* — Blaine Lankford
(74) *Attorney, Agent, or Firm* — Goodwin Procter LLP

(57) ABSTRACT

Phenotypic antimicrobial susceptibility testing (AST), the gold-standard diagnostic that indicates whether an antimicrobial will be clinically effective, often suffer the slowest times-to-result for the most resistant pathogens. Here we introduce novel assays to be performed in parallel with standard AST assays that provide additional resistance information and enable rapid, same-shift reporting of AST results for a plurality of pathogens.

19 Claims, 5 Drawing Sheets

SYSTEMS AND METHODS FOR PERFORMING ANTIMICROBIAL SUSCEPTIBILITY TESTING

CROSS-REFERENCE TO RELATED APPLICATIONS

This application is a continuation of U.S. patent application Ser. No. 17/004,848, filed Aug. 27, 2020, which claims the benefit of and priority to U.S. Provisional Patent Application No. 62/892,305, filed Aug. 27, 2019. The entire contents of these applications are incorporated by reference in their entirety and for all purposes herein.

FIELD OF THE DISCLOSURE

This disclosure relates to clinical microbiological compositions, systems and methods, more particularly to compositions, systems and methods for the assessment of microbial susceptibility or resistance to antimicrobial agents.

BACKGROUND

Phenotypic AST is the gold-standard method for determining clinical efficacy of antibiotics. The key test output is the minimum inhibitory concentration (MIC). The MIC is determined for each antimicrobial by testing the growth of a microbe sample in multiple antimicrobial dilutions in parallel and determining the lowest antimicrobial concentration that effectively inhibited microbial growth. As dictated by the Centers for Laboratory Standards Institute (CLSI) M100 reference manual for broth microdilution (BMD) AST, doubling (serial) dilutions of antibiotics are the standard and all wells are to be inoculated with the same microorganism concentration, since MIC determinations are based on assessments of relative growth.

The desire to have same-shift AST results, important for improving infectious diseases patient care as well as for combatting the current antimicrobial resistance epidemic, poses an accuracy challenge for antimicrobials to which microorganisms have developed resistance mechanisms that are slowly induced and/or non-uniformly expressed (heteroresistance). Such strains either directly or effectively express resistant phenotypes as only a fraction of the total number of cells in a given reservoir, generally $<10^3$-$10^4$ cells out of in $10^5$-$10^6$ cells. For example, it is well known to those skilled in the art that some strains of Enterococci harbor slowly-induced vancomycin resistance mechanisms. Thus, rapid assays may be prone to false susceptibility calls, a particularly acute issue in the case of vancomycin, which is commonly relied upon by physicians as a broad-spectrum gram-positive agent.

SUMMARY

In an aspect, this disclosure describes a method for determining the minimum inhibitory concentration (MIC) and/or a qualitative susceptibility result of an antimicrobial for a microorganism-comprising sample. The method may comprise inoculating panels wherein a microorganism is present at concentration $C_{m0}$ in a plurality of reservoirs in a dilution series of antimicrobial A that extends 3 or more dilutions from a low concentration of antimicrobial ($C_{AL}$) that is at or below a susceptible breakpoint to a high concentration of antimicrobial ($C_{AH}$) that is at or above a resistant breakpoint, the microorganism is present at a concentration$\geq 2 \times C_{m0}$ in one or more high microorganism load reservoirs (HMLRs) comprising antimicrobial A at a concentration$\geq C_{AL}/4$, and no microorganism is present in one or more control HMLR, wherein the control HMLR optionally comprises the same antimicrobial concentration as in the HMLR. The method may also comprise incubating the panels under conditions promoting microorganism growth, determining growth at a minimum of two discrete time intervals, wherein the first interval, $T_1$, is between 30 and 240 minutes and the second interval, $T_2$, is between 30 and 120 minutes, and measuring relative growth during $T_2$ and based on said growth measurement, determining the MIC and/or qualitative susceptibility interpretations from the dilution series reservoirs.

In various embodiments, growth in the HMLR may be determined optically following addition of a metabolic viability probe. The viability probe may be added prior to the onset of panel incubation. The viability probe may comprise resazurin and methylene blue. The viability probe may comprise ferrous and ferric potassium salts. The viability probe may comprise 1-methoxy-5-methlyphenasinum methyl sulfate. The viability probe may generate an optical signal. The viability probe may be measured by fluorescence. The conditions promoting microorganism growth may comprise incubation at 31-39° C., 33-37° C. The conditions promoting microorganism growth may comprise orbital shaking. $C_{m0}$ may be between $1 \times 10^5$ and $5 \times 10^6$ CFU/mL, preferably between $2 \times 10^5$ and $2 \times 10^6$ CFU/mL. $T_1$ may be 30-240, preferably 120-210, minutes. $T_2$ may be 30-120, preferably 45-90, minutes. One or more additional growth periods ($T_n$) beyond $T_2$ may be performed. The data from the additional growth periods up to $T_n$ may be used to determine MIC. Multiple growth measurements in HMLR reservoirs may be performed during $T_1$ and/or $T_2$. The data may comprise multiple growth measurements during one or more of the growth periods. A sufficient growth assay may be used to determine when sufficient growth has been achieved in a plurality of dilution series reservoirs on the panel to initiate one or more MIC-determining assays. The sufficient growth assay may be performed with a metabolic dye. The sufficient growth assay may be used to determine the number of growth periods for the HMLR assay. Determining MIC may comprise a viability assay where a probe is added following a sufficient growth assay threshold being achieved and a surface area assay following the viability assay. Each reservoir may be in a panel comprising approximately 96, 384, or 1536 unique reservoirs.

In various embodiments, the microorganisms may be bacteria, fungi, protozoa, and/or archaea. The bacteria may be selected from the group consisting of *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardnerella* spp., *Haemophilus* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., and combinations thereof. The fungi may be selected from the group consisting of *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp., *Sporothrix, Exserohilum, Cladosporium*, ringworm, mucormycetes, and combinations thereof.

The sample may be one or more inoculates derived from samples selected from blood, cerebrospinal fluid, urine, stool, vaginal, sputum, bronchoalveolar lavage, throat, nasal/wound swabs, and combinations thereof. The sample may be an unprocessed raw biological sample. The sample may be a processed biological sample.

In various embodiments, a signaling agent may be associated with one or more binding moieties capable of binding directly or indirectly to the intact microorganisms. A may be one or more of, but not limited to, the following: Amikacin, Amikacin-fosfomycin, Amoxicillin, Amoxicillin-clavulanate, Ampicillin, Ampicillin-sulbactam, Azithromycin, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Voriconazole and a salt or hydrate form thereof.

In an aspect, the disclosure describes a method of determining a qualitative susceptibility result of an antimicrobial for a microorganism-comprising sample. The method may comprise inoculating panels comprising a plurality of fluid reservoirs wherein the panels comprise a microorganism and an antimicrobial A, the microorganism is present at concentration $C_{m0}$ in a positive growth control well comprising no antimicrobial, the microorganism is present at a concentration $\geq 2 \times C_{m0}$ in one or more high microorganism load reservoirs (HMLRs) comprising antimicrobial A, and no microorganism is present in one or more control HMLR, wherein the control HMLR optionally comprises the same antimicrobial concentration as in the HMLR. The method may also comprise incubating the panels under conditions promoting microorganism growth, determining growth at a growth interval, measuring growth in the HMLR and the positive growth control well during the growth interval and based on said growth measurement, comparing the growth measured in the HMLR and the positive growth control wells to one another, and, based on said comparison determining the qualitative susceptibility interpretation for antimicrobial A and the microbe containing sample.

In various embodiments, the panels may comprise a microorganism is present at concentration $C_{m0}$ in a plurality of reservoirs in a dilution series of antimicrobial A that extends 3 or more dilutions from a low concentration of antimicrobial ($C_{AL}$) that is at or below a susceptible breakpoint to a high concentration of antimicrobial ($C_{AH}$) that is at or above a resistant breakpoint, wherein antimicrobial A is present in the HMLR at a concentration $\geq C_{AL}/4$. The comparison may comprise evaluating the level of growth of the positive control well and the HMLR well against a look up table. The comparison may comprise normalizing the level of growth of HMLR well to the positive control well and comparing the normalized value against a predetermined threshold. Growth in the HMLR may be determined optically following addition of a metabolic viability probe. The viability probe may be added prior to the onset of panel incubation. The viability probe may comprise resazurin and methylene blue. The viability probe may comprise ferrous and ferric potassium salts. The viability probe may comprise 1-methoxy-5-methlyphenasinum methyl sulfate. The viability probe may generate an optical signal. The viability probe may be measured by fluorescence. The conditions promoting microorganism growth may comprise incubation at 31-39° C., 33-37° C. The conditions promoting microorganism growth may comprise orbital shaking. $C_{m0}$ may be between $1 \times 10^5$ and $5 \times 10^6$ CFU/mL, preferably between $2 \times 10^5$ and $2 \times 10^6$ CFU/mL. Each reservoir may be in a panel comprising approximately 96, 384, or 1536 unique reservoirs.

In various embodiments, the microorganisms may be bacteria, fungi, protozoa, and/or archaea. The bacteria may be selected from the group consisting of *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardnerella* spp., *Haemophilus* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., and combinations thereof. The fungi may be selected from the group consisting of *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp., *Sporothrix, Exserohilum, Cladosporium*, ringworm, mucormycetes, and combinations thereof. The sample may be one or more inoculates derived from samples selected from blood, cerebrospinal fluid, urine, stool, vaginal, sputum, bronchoalveolar lavage, throat, nasal/wound swabs, and combinations thereof. The sample may be an unprocessed raw biological sample. The sample may be a processed biological sample.

In various embodiments, a signaling agent may be associated with one or more binding moieties capable of binding directly or indirectly to the intact microorganisms. A may be one or more of, but not limited to, the following: Amikacin, Amikacin-fosfomycin, Amoxicillin, Amoxicillin-clavulanate, Ampicillin, Ampicillin-sulbactam, Azithromycin, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Voriconazole and a salt or hydrate form thereof.

In an aspect, the disclosure describes a rapid method of determining a qualitative susceptibility of a microbe-containing sample to an antimicrobial. This method may comprise the steps of inoculating at least two reference wells of an assay panel comprising a plurality of fluid wells with a first quantity of the microbe-containing sample, inoculating at least one experimental well of the assay panel with a second quantity of the microbe-containing sample, the experimental well comprising a quantity of the antimicrobial, storing the assay panel under conditions that promote microbial growth, interrogating a first reference well of the panel to assess a level of microbial growth, and if the assessed level of growth exceeds a predetermined threshold, and measuring a signal from the at least one experimental well and a second reference well, wherein the signal is proportional to one of a microbial surface area or a microbial metabolic process. The method may also comprise, based on the signal measured in the second reference well, determining a cutoff value for a signal measured in the experimental well, and comparing the signal measured in the experimental well to the cutoff value, and determining, based on said comparing, the qualitative susceptibility of the microbe-containing sample to the antimicrobial.

The systems, compositions and methods of the present disclosure can include one or more of the following enumerated embodiments:

1. A method for determining the minimum inhibitory concentration (MIC) and/or a qualitative susceptibility result of an antimicrobial for a microorganism-comprising sample, the method comprising:
   inoculating panels wherein
     a microorganism is present at concentration $C_{m0}$ in a plurality of reservoirs in a dilution series of antimicrobial A that extends 3 or more dilutions from a low concentration of antimicrobial ($C_{AL}$) that is at or below a susceptible breakpoint to a high concentration of antimicrobial ($C_{AH}$) that is at or above a resistant breakpoint;
     the microorganism is present at a concentration $\geq 2 \times C_{m0}$ in one or more high microorganism load reservoirs (HMLRs) comprising antimicrobial A at a concentration $\geq C_{AL}/4$;
   incubating the panels under conditions promoting microorganism growth;
   measuring relative growth in dilutions series reservoirs and in HMLRs; and
   determining the MIC and/or qualitative susceptibility interpretations from the relative growth measurements.
2. The method of embodiment 1, wherein growth in the HMLRs is determined optically.
3. The method of embodiment 2, wherein growth in the HMLRs is determined following addition of a metabolic viability probe.
4. The method of embodiment 2, wherein the viability probe is added prior to the onset of panel incubation.
5. The method of embodiment 2, wherein the viability probe comprises resazurin and methylene blue.
6. The method of embodiment 2, wherein the viability probe comprises ferrous and ferric potassium salts.
7. The method of embodiment 2, wherein the viability probe comprises 1-methoxy-5-methlyphenasinum methyl sulfate.
8. The method of embodiment 2, wherein the viability probe generates an optical signal.
9. The method of embodiment 2, wherein the viability probe is measured by fluorescence.
10. The method of embodiment 2, wherein two or more fluorescent measurements of the viability probe are made at distinct intervals.
11. The method of embodiment 2, wherein growth in the HMLRs is determined by time-resolved fluorescence or time-gated luminescence.
12. The method of embodiment 2, wherein growth in the HMLRs is determined following the addition of a probe capable of binding microbial surfaces.
13. The method of embodiment 2, wherein the surface binding probe is fluorescent.
14. The method of embodiment 1, wherein the conditions promoting microorganism growth comprise incubation at 31-39° C., 33-37° C.
15. The method of embodiment 1, wherein the conditions promoting microorganism growth comprise orbital shaking.
16. The method of embodiment 1, wherein Go is between $1 \times 10^5$ and $5 \times 10^6$ CFU/mL, preferably between $2 \times 10^5$ and $2 \times 10^6$ CFU/mL.
17. The method of embodiment 1, wherein one or more optical probes are added following an initial incubation period.
18. The method of embodiment 1, wherein determining MIC comprises a viability assay where a probe is added following a growth threshold being achieved and a surface area assay following the viability assay, wherein the surface area assay comprises
   incubating a liquid suspension of microorganisms in the presence of an antimicrobial under conditions that promote growth of the microorganisms,
   adding a signaling agent that binds to a surface of the microorganisms;
   separating the microorganisms bound by the signaling agent from unbound signaling agent; and measuring signal levels associated with the microorganisms as compared to one or more controls, thereby measuring the antimicrobial susceptibility of the microorganisms;
wherein the signaling agent comprises a linker group L, and an amplifier group 104 comprises an Europium coordination complex; and wherein,
L forms a covalent bond to the amplifier group 104; or
L forms one or more non-covalent interactions with an amplifier group 104.
19. The method of embodiment 18, wherein the antimicrobial susceptibility of the microorganisms is determined in less than 5 hours.
20. The method of embodiment 18, wherein adding the signaling agent occurs during the incubating step.
21. The method of embodiment 18, wherein adding the signaling agent occurs after the incubating step.
22. The method of embodiment 18, wherein the linker group L comprises:
a microorganism binding chemical moiety 101, which forms a covalent bond or a non-covalent interaction with the surface of a microorganism;
a spacer moiety 102, covalently attached to the chemical moiety 101 and to another chemical moiety 103; and
the chemical moiety 103, which forms a covalent or non-covalent interaction with the amplifier group 104.
23. The method of embodiment 22, wherein chemical moiety 101 forms covalent bond in the presence of one or more agents that promote coupling, selected from the group consisting of glutaraldehyde, formaldehyde, paraformaldehyde, EDC, DCC, CMC, DIC, HATU, Woodward's Reagent, N,N'-carbonyl diimidazole, acrylates, amides, imides, anhydrides, chlorotriazines, epoxides, isocyanates, isothiocyanates, organic acids, monomers, polymers, silanes, silcates, NHS, sulfo-NHS, and a combination thereof.
24. The method of embodiment 22, wherein chemical moiety 101 forms a non-covalent interaction with the surface of a microorganism, wherein the non-covalent interaction comprises ionic interactions, van der Waals interactions, hydrophobic interactions, π-π interactions, or hydrogen bonding, or any combination thereof.
25. The method of embodiment 22, wherein chemical moiety 101 comprises a nucleophilic functional group, wherein said nucleophilic functional group is amino, hydrazino, hydroxyamino, or thiol.
26. The method of embodiment 22, wherein chemical moiety 101 comprises an electrophilic functional group, wherein said electrophilic functional group comprises an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, an acryloyl derivative, aldehyde, ketone, carboxylic acid, ester, acetyl chloride, or acetic anhydride.
27. The method of embodiment 22, wherein spacer moiety 102 is hydrophobic.
28. The method of embodiment 22, wherein spacer moiety 102 is hydrophilic.

29. The method of embodiment 22, wherein spacer moiety 102 is oligomeric or polymeric, derived from peptide linkages, or comprised of inorganic linkages.
30. The method of embodiment 22, wherein spacer moiety 102 comprises a repeating group that is:

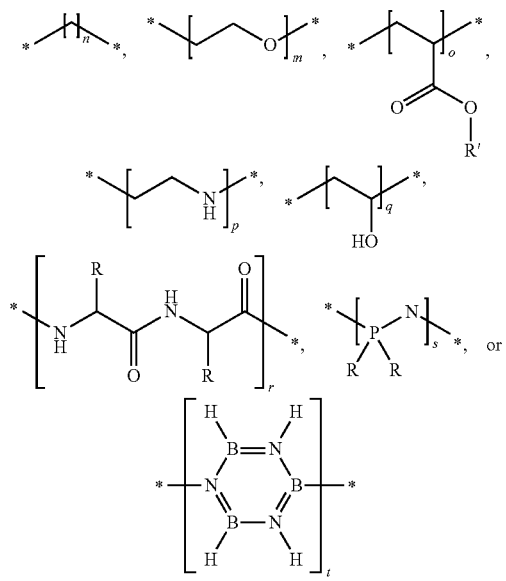

wherein,
each of n, m, o, p, and q independently is an integer of 1 to 300.
31. The method of embodiment 22, wherein spacer moiety 102 is

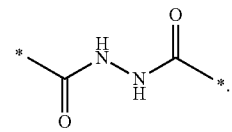

32. The method of embodiment 22, wherein chemical moiety 103 comprises a nucleophilic group.
33. The method of embodiment 22, wherein chemical moiety 103 comprises an electrophilic group.
34. The method of embodiment 22, wherein chemical moiety 103 comprises a group that is carbonyl, alkenyl, alkynyl, hydroxyl, amino, thiol, maleimide, succinimide, hydroxysuccinimide, or biotinyl.
35. The method of embodiment 22, wherein chemical moiety 103 comprises a group that is

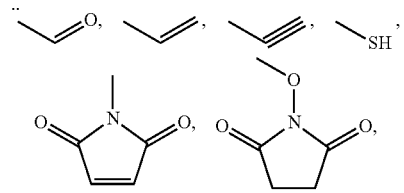

-continued

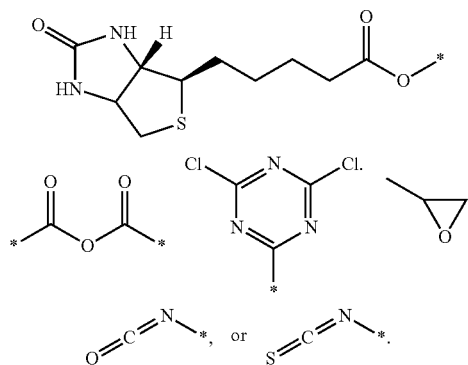

36. The method of embodiment 22, wherein chemical moiety 103 is formed from a chemical structure comprising a group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate.

37. The method of embodiment 36, wherein said group that is carbonyl, alkenyl, alkynyl, hydroxyl, amino, thiol, maleimide, succinimide, hydroxysuccinimide, or biotinyl forms a covalent bond to the amplifier group 104, or forms a non-covalent bond to the amplifier group 104.

38. The method of embodiment 18, wherein linker group L has the following structure or is formed from the following structure,

(I)

wherein
X is

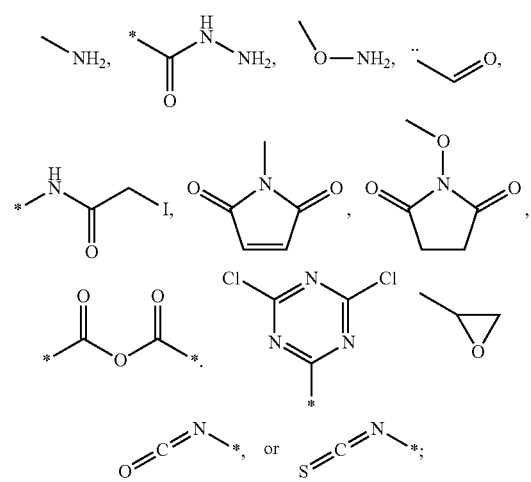

R is

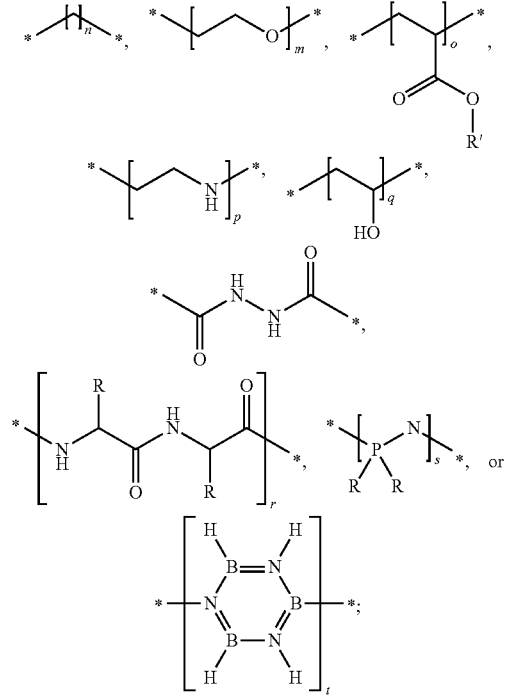

Y is

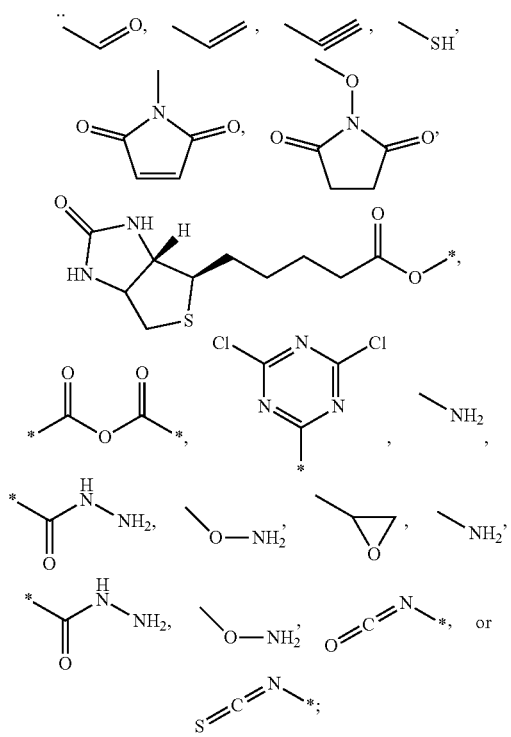

each of j and k independently is an integer of 0 to 100; and
each of n, m, o, p, and q independently is an integer of 1 to 100.

39. The method of embodiment 38, wherein X forms a covalent bond or a non-covalent interaction with the surface of a microorganism;
and/or
Y forms a covalent bond to an amplifier group 104 that is a chemical or biochemical amplifier.
40. The method of embodiment 18, wherein said Europium coordination complex comprises a structure that is:
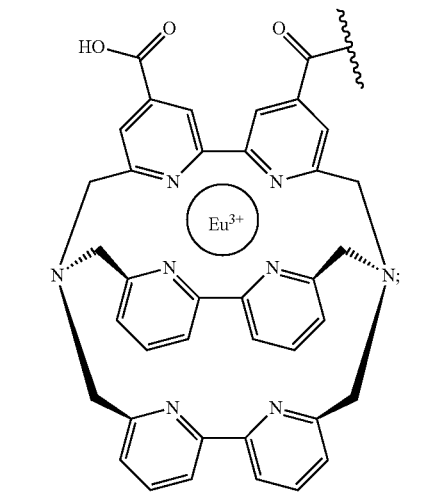
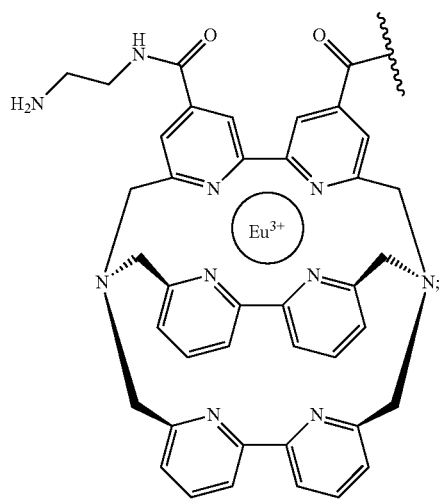
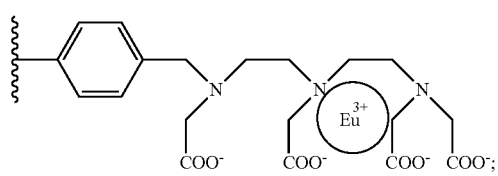
-continued
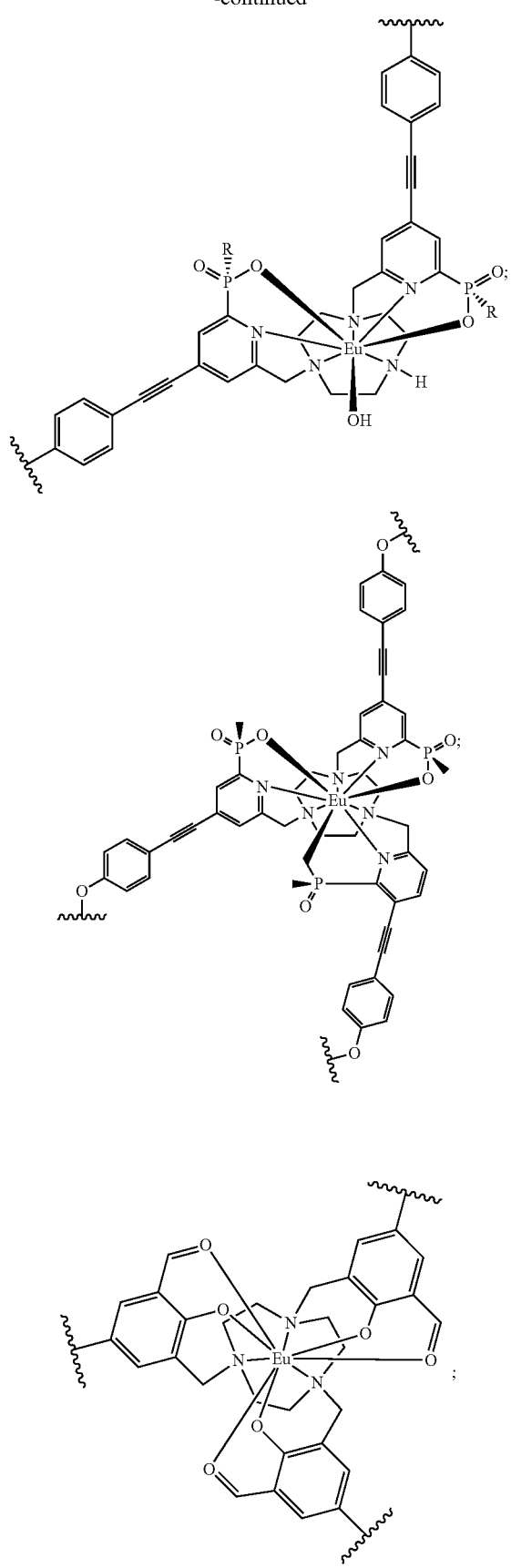

13
-continued
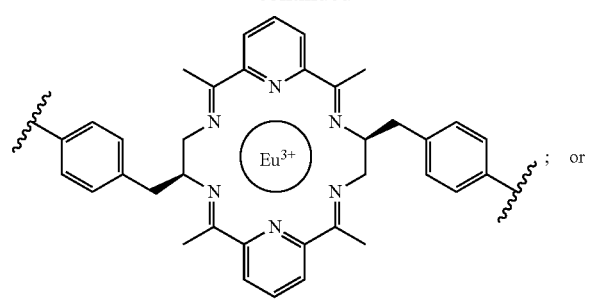
; or
14
-continued
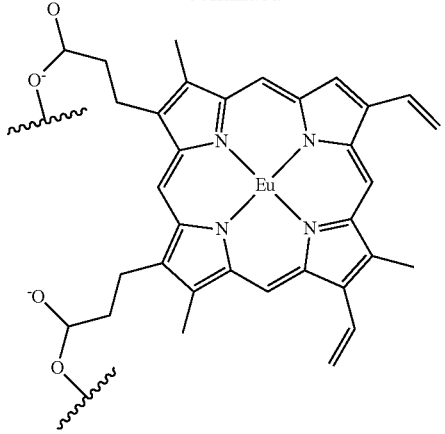
.
41. The method of embodiment 40, wherein the signaling agent comprises or is formed from a structure selected from the group consisting of:
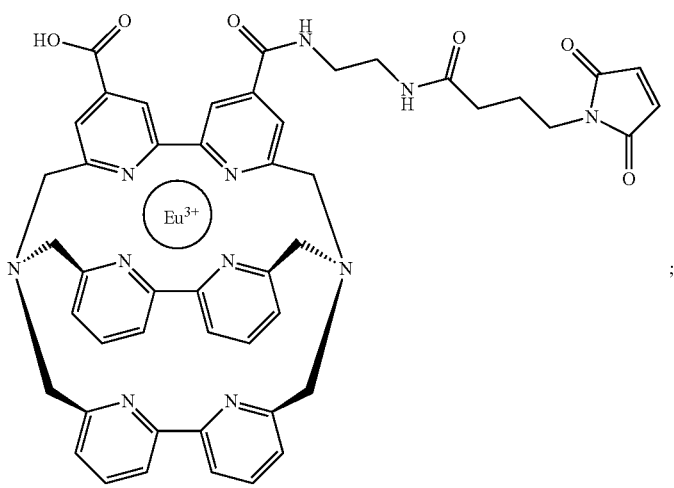
Eu-cryptate-maleimide
;
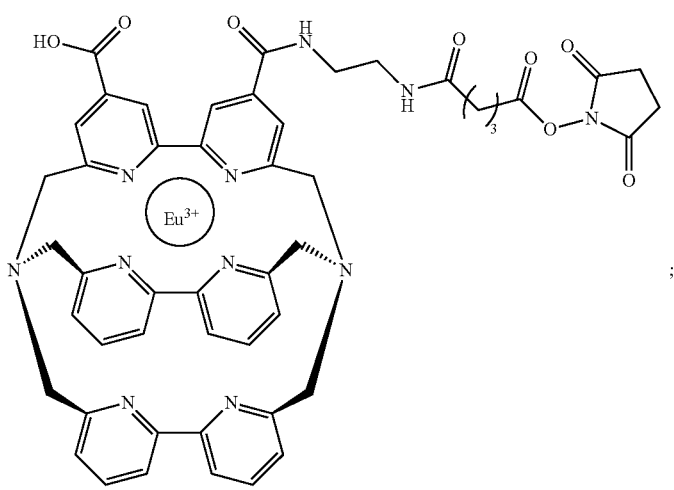
Eu-cryptate-NHS
;

-continued
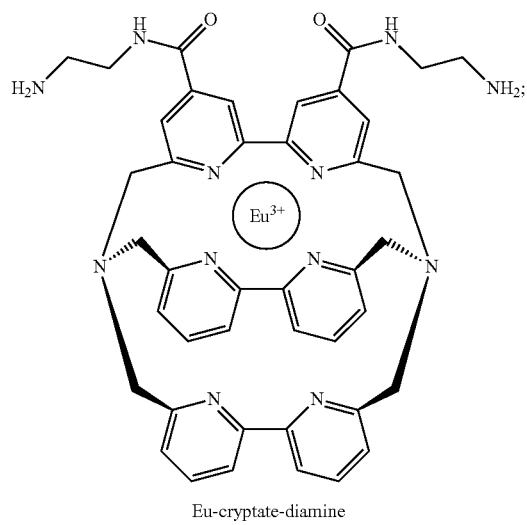
Eu-cryptate-diamine
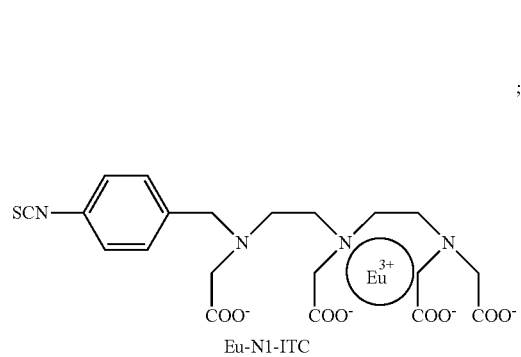
Eu-N1-ITC
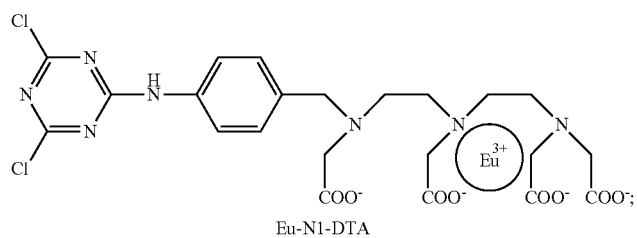
Eu-N1-DTA
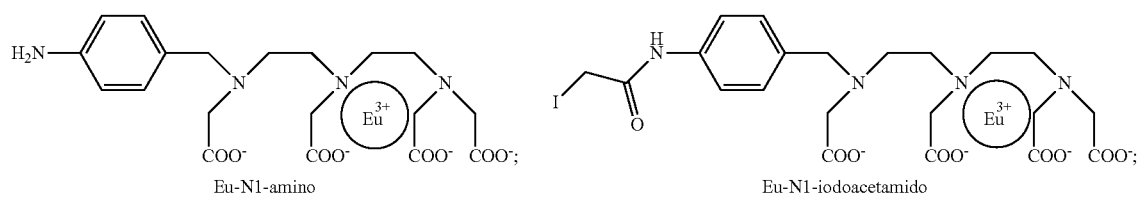
Eu-N1-amino          Eu-N1-iodoacetamido
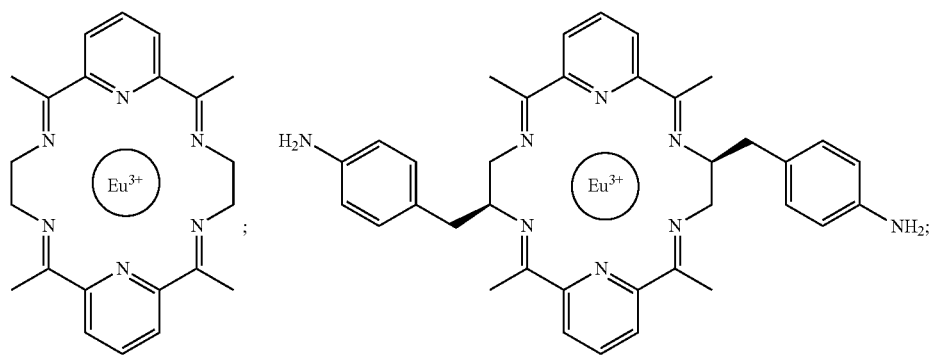
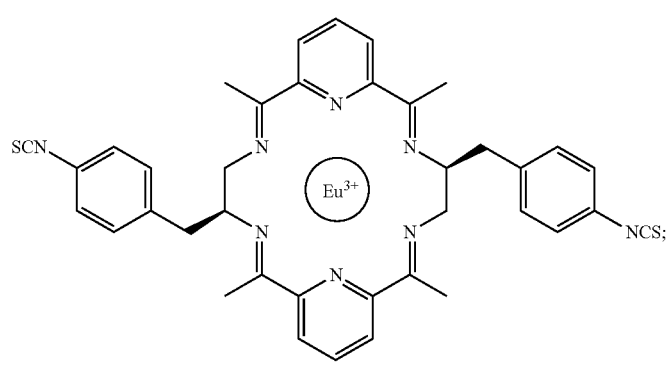

-continued

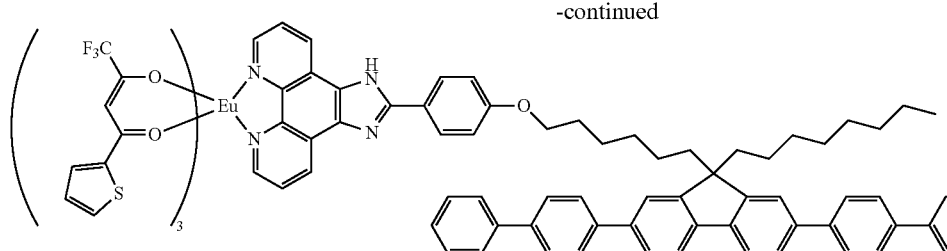

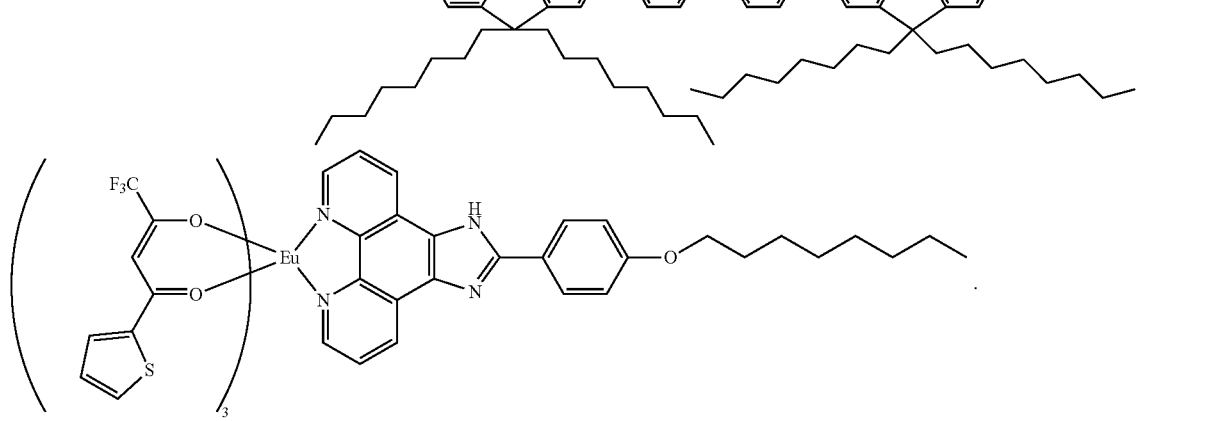
; and

42. The method of embodiment 1, wherein the HMLRs comprise antimicrobial A at a concentration $\geq C_{AL}$.
43. The method of embodiment 1, wherein the HMLRs comprise a microorganism concentration $\geq 3\times C_{m0}$, $\geq 4\times C_{m0}$, $\geq 5\times C_{m0}$, $\geq 6\times C_{m0}$, $\geq 7\times C_{m0}$, $\geq 8\times C_{m0}$, $\geq 9\times C_{m0}$, $\geq 10\times C_{m0}$, $\geq 11\times C_{m0}$, $\geq 12\times C_{m0}$, $\geq 13\times C_{m0}$, $\geq 14\times C_{m0}$, $\geq 15\times C_{m0}$, $\geq 16\times C_{m0}$, $\geq 17\times C_{m0}$, $\geq 18\times C_{m0}$, $\geq 19\times C_{m0}$, $\geq 20\times C_{m0}$.
44. The method of embodiment 1, wherein no microorganism and no antimicrobials are present in one or more positive control reservoirs.
45. The method of embodiment 1, wherein each reservoir is in a panel comprising approximately 96, 384, or 1536 unique reservoirs.
46. The method of embodiment 1, wherein the microorganisms are bacteria, fungi, protozoa, and/or archaea.
47. The method of embodiment 46, wherein the bacteria are selected from the group consisting of *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardnerella* spp., *Haemophilus* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., and combinations thereof.
48. The method of embodiment 46, wherein the fungi are selected from the group consisting of *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp., *Sporothrix*, *Exserohilum*, *Cladosporium*, ringworm, mucormycetes, and combinations thereof.
49. The method of embodiment 1, wherein the sample is one or more inoculates derived from samples selected from blood, cerebrospinal fluid, urine, stool, vaginal, sputum, bronchoalveolar lavage, throat, nasal/wound swabs, and combinations thereof
50. The method of embodiment 49, wherein the sample is an unprocessed raw biological sample.
51. The method of embodiment 49, wherein the sample is a processed biological sample.
52. The method of embodiment 1, wherein a signaling agent is associated with one or more binding moieties capable of binding directly or indirectly to the intact microorganisms.
53. The method of embodiment 1, wherein A is one or more of, but not limited to, the following: Amikacin, Amikacin-fosfomycin, Amoxicillin, Amoxicillin-clavulanate, Ampicillin, Ampicillin-sulbactam, Azithromycin, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Voriconazole and a salt or hydrate form thereof.

54. The method of embodiment 1, wherein the antimicrobial is vancomycin.

55. The method of embodiment 1, wherein the method further comprises performing one or more checkpoint assays to determine if microorganism growth has achieved a threshold value; and
   (a) if the threshold value is achieved, performing at least one assay to measure the relative growth in the reservoirs of the dilution series and the HMLRs, and based upon said measuring, determining a qualitative susceptibility result (QSR) and obtaining a minimum inhibitory concentration (MIC); or
   (b) if the threshold value is not achieved, performing one or more additional incubation periods under conditions promoting microorganism growth until
      (i) the threshold value is achieved, and thereafter performing step (a); or
      (ii) a maximum of 18 hours has transpired without the threshold value being achieved and no further assays are performed.

56. The method of embodiment 55, wherein at least one assay is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.

57. The method of embodiment 55, wherein each of the assays is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.

58. The method of embodiment 57, wherein the metabolic probe comprises 7-hydroxy-10-oxidophenoxazin-10-ium-3-one (resazurin).

59. The method of embodiment 57, wherein the surface-binding probe comprises a coordination complex of a lanthanide with diethylenetriaminetetraacetic acid or a cryptate ligand.

60. The method of embodiment 59, wherein the surface-binding probe comprises

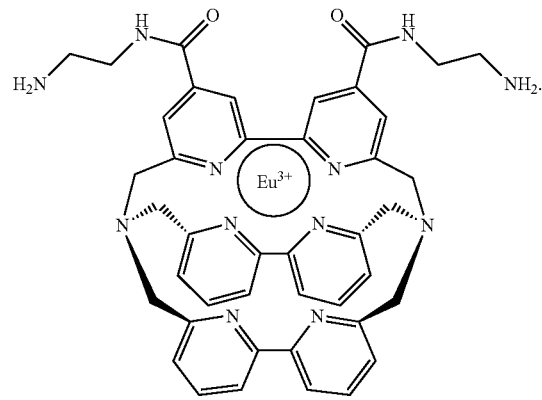

61. The method of embodiment 59, wherein the surface binding probe comprises europium, strontium, terbium, samarium, and dysprosium, or a combination thereof.

62. The method of embodiment 55, wherein the plurality of assays for determining microorganism growth comprises (a) nucleic acid amplification, (b) nucleic acid sequencing, (c) use of adenosine triphosphate, (d) light scattering, (e) optical microscopy, or (f) measuring microorganism mass.

63. The method of embodiment 55, wherein the different growth assays are performed (a) sequentially (b) or concurrently.

64. The method of embodiment 55, wherein at least one well of the panel is a checkpoint assay well comprising one of:
   (a) a growth indicator during the initial incubation period and/or additional incubation period; and/or
   (b) no growth indicator, wherein the checkpoint assay is performed by absorbance, nephelometry, mass resonance, or acoustically.

65. The method of embodiment 55, wherein at least one well of the panel is a checkpoint assay well and does not comprise antimicrobials.

66. The method of embodiment 55, wherein the threshold value comprises a value dependent on the microorganism.

67. The method of embodiment 64, wherein the growth indicator comprises resazurin.

68. The method of embodiment 55, wherein the one or more microorganisms derive from a clinical sample.

69. The method of embodiment 68, wherein the clinical sample comprises a microorganism from the group consisting of: *Escherichia* spp., *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardnerella* spp., *Haemophilus* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachy-*

*botrys* spp., *Sporothrix, Exserohilum, Cladosporium*, ringworm, mucormycetes, and a combination thereof
70. The method of embodiment 55, wherein the steps are performed in an automated platform for antimicrobial susceptibility testing.
71. A method of determining a qualitative susceptibility result of an antimicrobial for a microorganism-comprising sample, the method comprising:
    inoculating panels comprising a plurality of fluid reservoirs wherein
        the panels comprise a microorganism and an antimicrobial A;
        the microorganism is present at concentration $C_{m0}$ in a positive growth control well comprising no antimicrobial;
        the microorganism is present at a concentration $\geq 2 \times C_{m0}$ in one or more high microorganism load reservoirs (HMLRs) comprising antimicrobial A; and
        incubating the panels under conditions promoting microorganism growth;
    determining growth at a growth interval;
    measuring growth in the HMLR and the positive growth control well during the growth interval and based on said growth measurement;
    comparing the growth measured in the HMLR and the positive growth control wells to one another;
    based on said comparison, determining the qualitative susceptibility interpretation for antimicrobial A and the microbe containing sample; and
    combining these data with growth measurements from the antimicrobial dilution series to determine a minimal inhibitory concentration (MIC).
72. The method of embodiment 71, wherein the panels comprise a microorganism is present at concentration $C_{m0}$ in a plurality of reservoirs in a dilution series of antimicrobial A that extends 3 or more dilutions from a low concentration of antimicrobial ($C_{AL}$) that is at or below a susceptible breakpoint to a high concentration of antimicrobial ($C_{AH}$) that is at or above a resistant breakpoint,
    wherein antimicrobial A is present in the HMLR at a concentration $\geq C_{AL}/4$.
73. The method of embodiment 71, wherein the comparison comprises evaluating the level of growth of the positive control well and the HMLR well against a look up table.
74. The method of embodiment 71, wherein the comparison comprises normalizing the level of growth of HMLR well to the positive control well and comparing the normalized value against a predetermined threshold.
75. The method of embodiment 71, wherein growth in the HMLR is determined optically following addition of at least one of a metabolic viability probe and a surface binding probe.
76. The method of embodiment 75, wherein the viability probe is added prior to the onset of panel incubation.
77. The method of embodiment 75, wherein the viability probe comprises resazurin and methylene blue.
78. The method of embodiment 75, wherein the viability probe comprises ferrous and ferric potassium salts.
79. The method of embodiment 75, wherein the viability probe comprises 1-methoxy-5-methlyphenasinum methyl sulfate.
80. The method of embodiment 75, wherein the viability probe generates an optical signal.
81. The method of embodiment 75, wherein the viability probe is measured by fluorescence.
82. The method of embodiment 75, wherein the viability probe is fluorescently measured two or more discrete times.
83. The method of embodiment 71, wherein one or more optical probes are added following an initial incubation period.
84. The method of embodiment 71, wherein determining MIC comprises a viability assay where a probe is added following a growth threshold being achieved and a surface area assay following the viability assay, wherein the surface area assay comprises
    incubating a liquid suspension of microorganisms in the presence of an antimicrobial under conditions that promote growth of the microorganisms,
    adding a signaling agent that binds to a surface of the microorganisms;
    separating the microorganisms bound by the signaling agent from unbound signaling agent; and
    measuring signal levels associated with the microorganisms as compared to one or more controls, thereby measuring the antimicrobial susceptibility of the microorganisms;
    wherein the signaling agent comprises a linker group L, and an amplifier group 104 comprises an Europium coordination complex; and wherein,
    L forms a covalent bond to the amplifier group 104; or
    L forms one or more non-covalent interactions with an amplifier group 104.
85. The method of embodiment 84, wherein the antimicrobial susceptibility of the microorganisms is determined in less than 5 hours.
86. The method of embodiment 84, wherein adding the signaling agent occurs during the incubating step.
87. The method of embodiment 84, wherein adding the signaling agent occurs after the incubating step.
88. The method of embodiment 84, wherein the linker group L comprises:
    a microorganism binding chemical moiety 101, which forms a covalent bond or a non-covalent interaction with the surface of a microorganism;
    a spacer moiety 102, covalently attached to the chemical moiety 101 and to another chemical moiety 103; and
    the chemical moiety 103, which forms a covalent or non-covalent interaction with the amplifier group 104.
89. The method of embodiment 88, wherein chemical moiety 101 forms covalent bond in the presence of one or more agents that promote coupling, selected from the group consisting of glutaraldehyde, formaldehyde, paraformaldehyde, EDC, DCC, CMC, DIC, HATU, Woodward's Reagent, N,N'-carbonyl diimidazole, acrylates, amides, imides, anhydrides, chlorotriazines, epoxides, isocyanates, isothiocyanates, organic acids, monomers, polymers, silanes, silcates, NHS, sulfo-NHS, and a combination thereof.
90. The method of embodiment 88, wherein chemical moiety 101 forms a non-covalent interaction with the surface of a microorganism, wherein the non-covalent interaction comprises ionic interactions, van der Waals interactions, hydrophobic interactions, π-π interactions, or hydrogen bonding, or any combination thereof.
91. The method of embodiment 88, wherein chemical moiety 101 comprises a nucleophilic functional group, wherein said nucleophilic functional group is amino, hydrazino, hydroxyamino, or thiol.

92. The method of embodiment 88, wherein chemical moiety 101 comprises an electrophilic functional group, wherein said electrophilic functional group comprises an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, an acryloyl derivative, aldehyde, ketone, carboxylic acid, ester, acetyl chloride, or acetic anhydride.

93. The method of embodiment 88, wherein spacer moiety 102 is hydrophobic.
94. The method of embodiment 88, wherein spacer moiety 102 is hydrophilic.
95. The method of embodiment 88, wherein spacer moiety 102 is oligomeric or polymeric, derived from peptide linkages, or comprised of inorganic linkages.
96. The method of embodiment 88, wherein spacer moiety 102 comprises a repeating group that is:

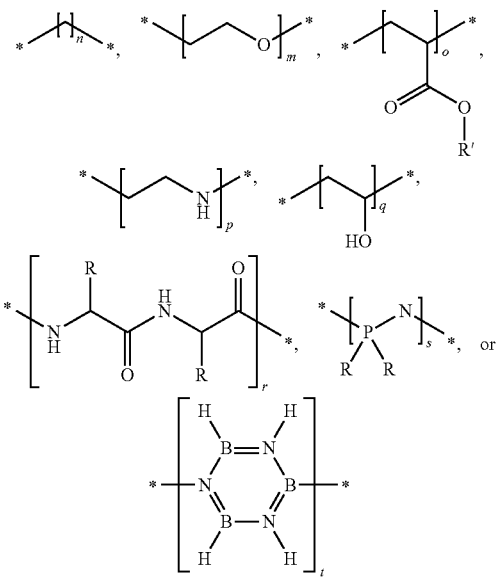

wherein,
each of n, m, o, p, and q independently is an integer of 1 to 300.

97. The method of embodiment 88, wherein spacer moiety 102 is

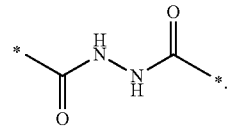

98. The method of embodiment 88, wherein chemical moiety 103 comprises a nucleophilic group.
99. The method of embodiment 88, wherein chemical moiety 103 comprises an electrophilic group.
100. The method of embodiment 88, wherein chemical moiety 103 comprises a group that is carbonyl, alkenyl, alkynyl, hydroxyl, amino, thiol, maleimide, succinimide, hydroxysuccinimide, or biotinyl.
101. The method of embodiment 88, wherein chemical moiety 103 comprises a group that is

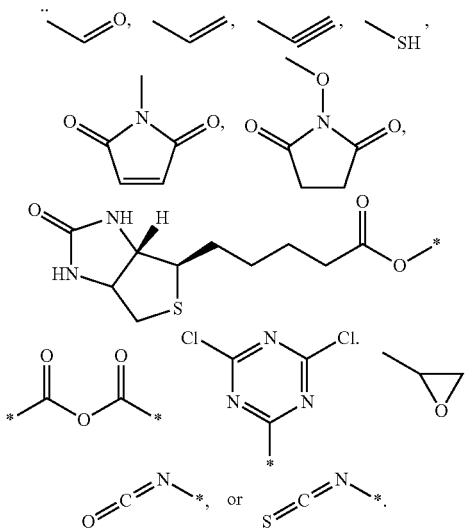

102. The method of embodiment 88, wherein chemical moiety 103 is formed from a chemical structure comprising a group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate.
103. The method of embodiment 102, wherein said group that is carbonyl, alkenyl, alkynyl, hydroxyl, amino, thiol, maleimide, succinimide, hydroxysuccinimide, or biotinyl forms a covalent bond to the amplifier group 104, or forms a non-covalent bond to the amplifier group 104.
104. The method of embodiment 84, wherein linker group L has the following structure or is formed from the following structure,

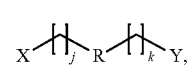

(I)

wherein
X is

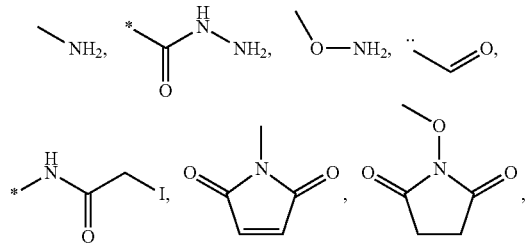

-continued

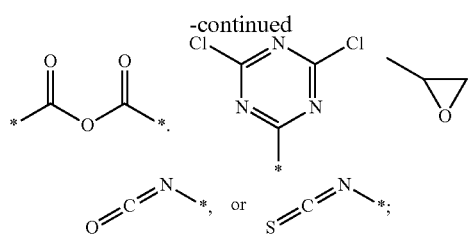

R is

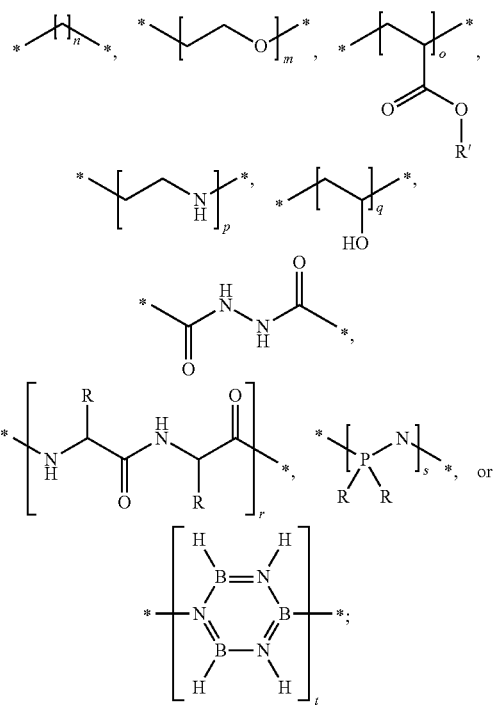

Y is

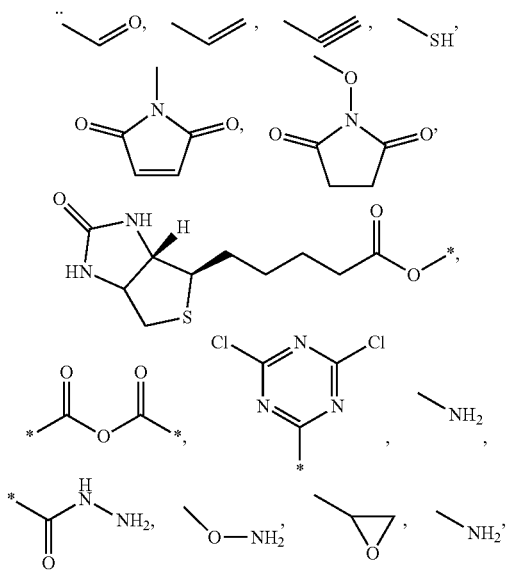

-continued

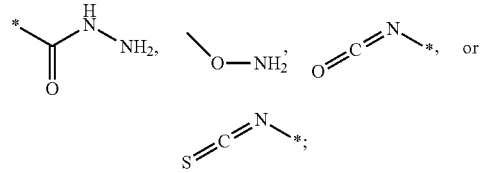

each of j and k independently is an integer of 0 to 100; and each of n, m, o, p, and q independently is an integer of 1 to 100.

105. The method of embodiment 104, wherein X forms a covalent bond or a non-covalent interaction with the surface of a microorganism;

and/or

Y forms a covalent bond to an amplifier group 104 that is a chemical or biochemical amplifier.

106. The method of embodiment 84, wherein said Europium coordination complex comprises a structure that is:

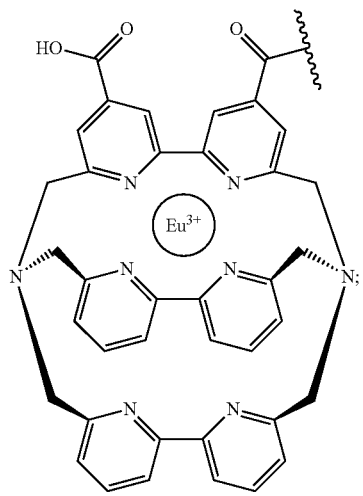

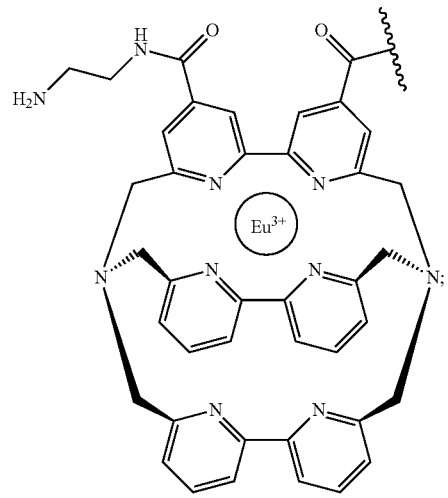

27
-continued
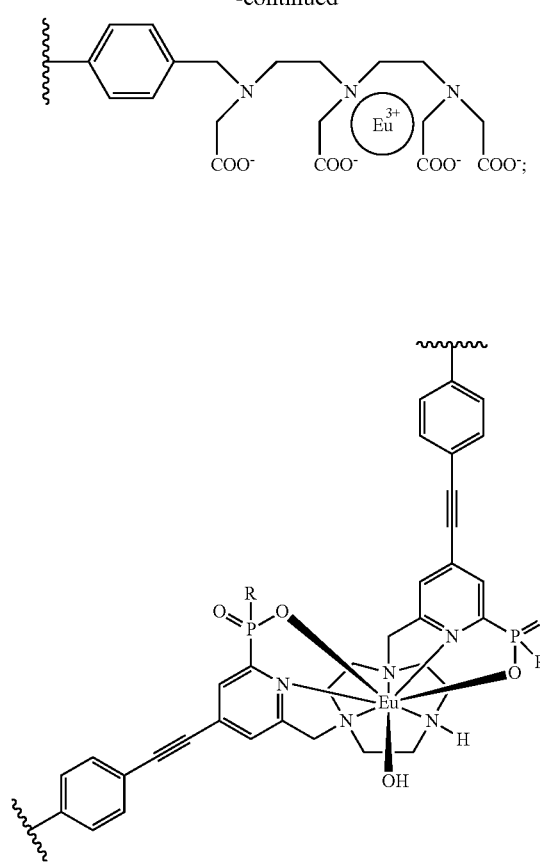
28
-continued
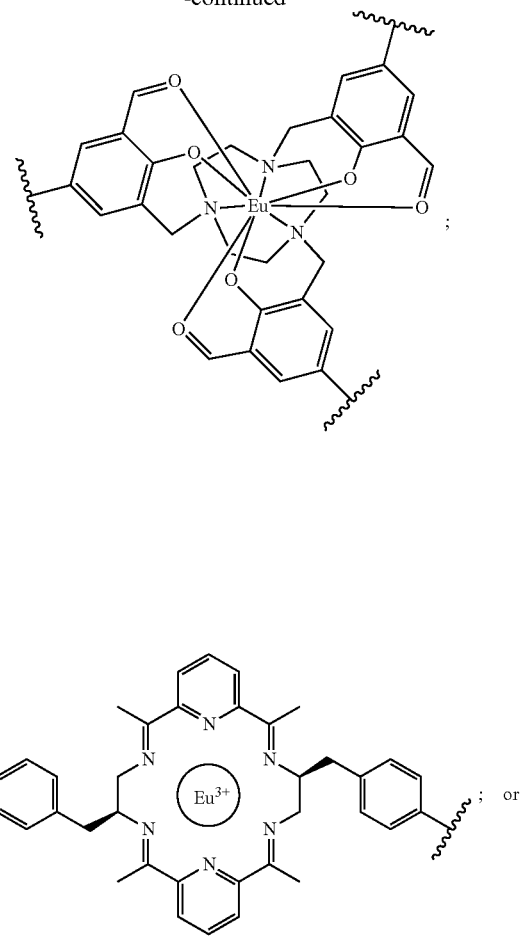
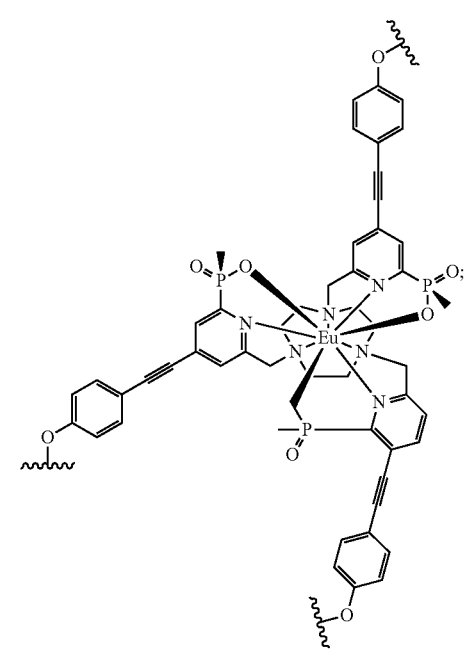
107. The method of embodiment 106, wherein the signaling agent comprises or is formed from a structure selected from the group consisting of:

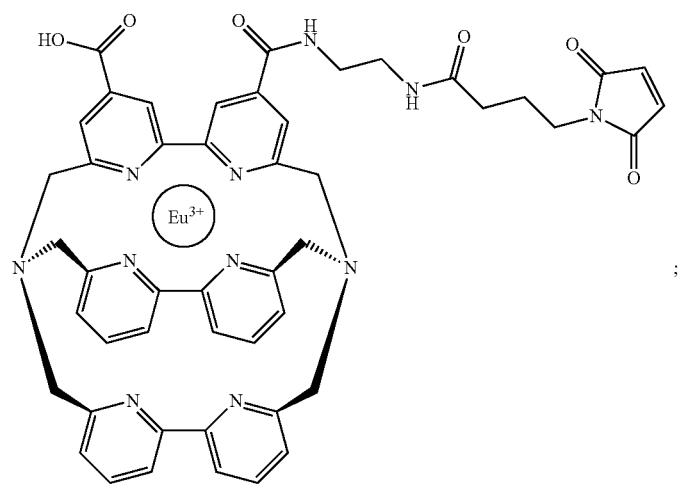
Eu-cryptate-maleimide
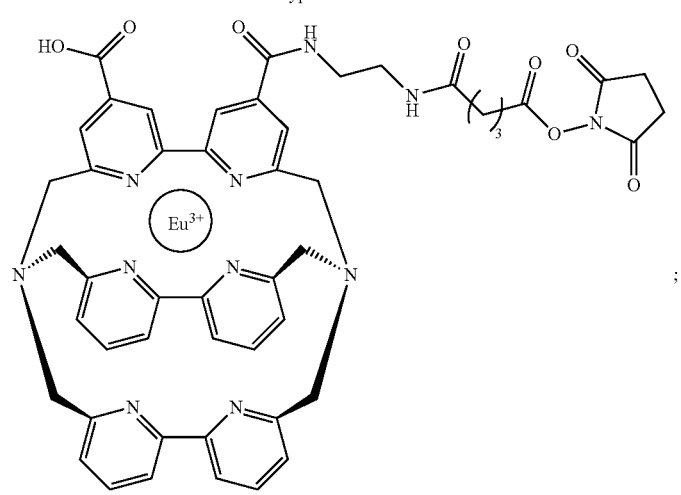
Eu-cryptate-NHS
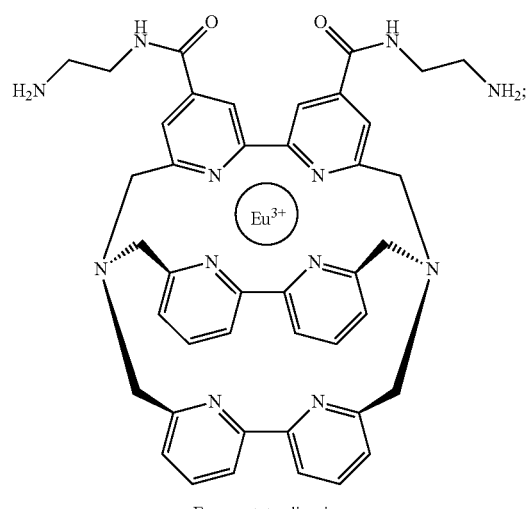
Eu-cryptate-diamine
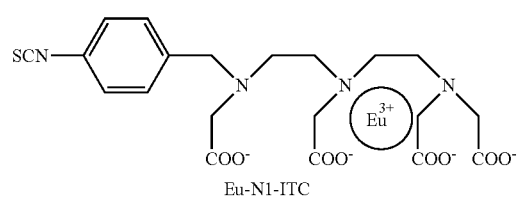
Eu-N1-ITC -continued
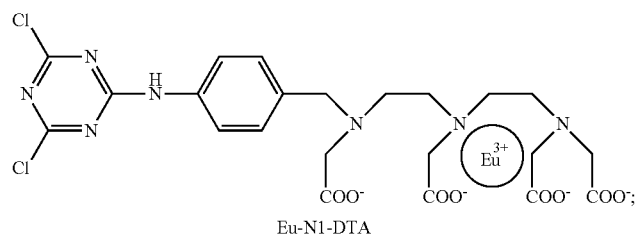
Eu-N1-DTA
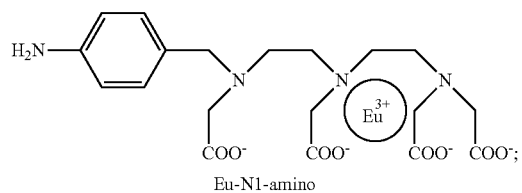
Eu-N1-amino
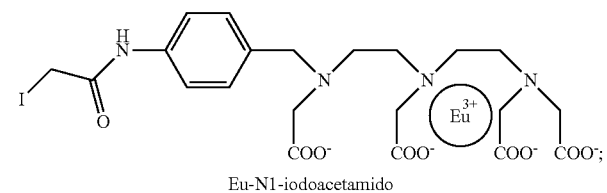
Eu-N1-iodoacetamido
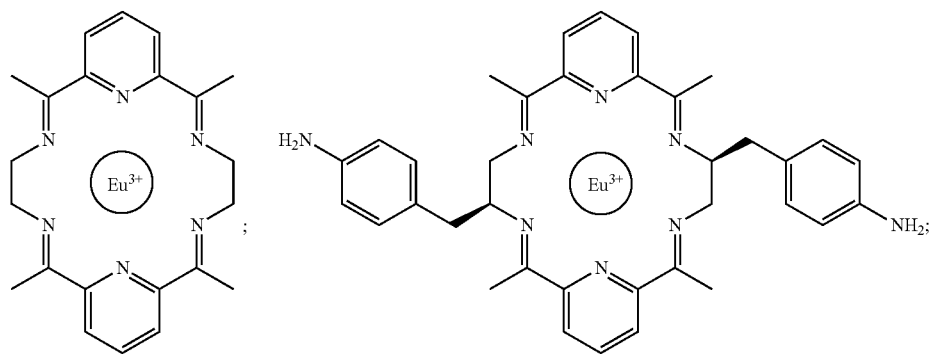
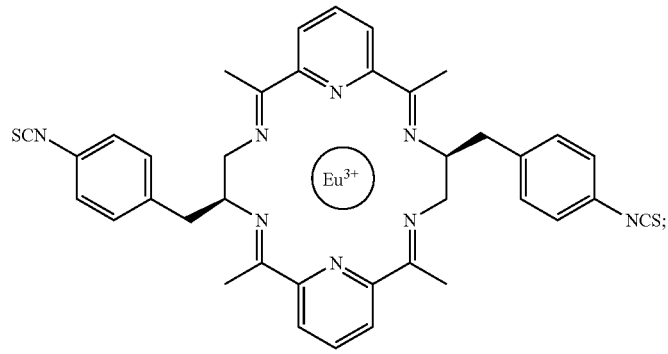
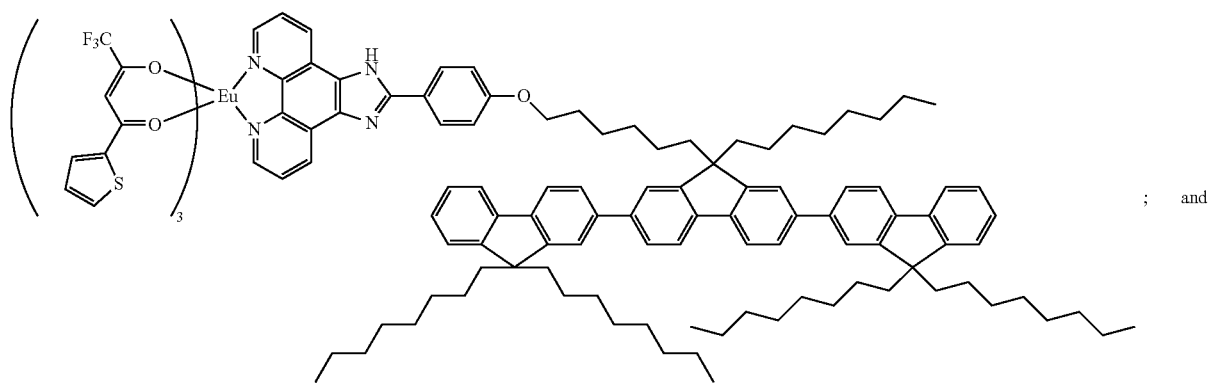
; and

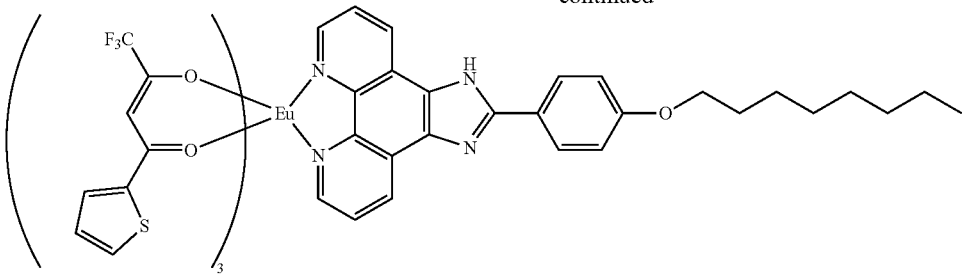

108. The method of embodiment 71, wherein the HMLRs comprise antimicrobial A at a concentration $\geq C_{AL}$.
109. The method of embodiment 71, wherein the HMLRs comprise a microorganism concentration $\geq 3 \times C_{m0}$, $\geq 4 \times C_{m0}$, $\geq 5 \times C_{m0}$, $\geq 6 \times C_{m0}$, $\geq 7 \times C_{m0}$, $\geq 8 \times C_{m0}$, $\geq 9 \times C_{m0}$, $\geq 10 \times C_{m0}$, $\geq 11 \times C_{m0}$, $\geq 12 \times C_{m0}$, $\geq 13 \times C_{m0}$, $\geq 14 \times C_{m0}$, $\geq 15 \times C_{m0}$, $\geq 16 \times C_{m0}$, $\geq 17 \times C_{m0}$, $\geq 18 \times C_{m0}$, $\geq 19 \times C_{m0}$, $\geq 20 \times C_{m0}$.
110. The method of embodiment 71, wherein the conditions promoting microorganism growth comprise incubation at 31-39° C., 33-37° C.
111. The method of embodiment 71, wherein the conditions promoting microorganism growth comprise orbital shaking.
112. The method of embodiment 71, wherein C m o is between $1 \times 10^5$ and $5 \times 10^6$ CFU/mL, preferably between $2 \times 10^5$ and $2 \times 10^6$ CFU/mL.
113. The method of embodiment 71, wherein each reservoir is in a panel comprising approximately 96, 384, or 1536 unique reservoirs.
114. The method of embodiment 71, wherein the method further comprises performing one or more checkpoint assays to determine if microorganism growth has achieved a threshold value; and
    (a) if the threshold value is achieved, performing at least one assay to measure the relative growth in the reservoirs of the dilution series and the HMLRs, and based upon said measuring, determining a qualitative susceptibility result (QSR) and obtaining a minimum inhibitory concentration (MIC); or
    (b) if the threshold value is not achieved, performing one or more additional incubation periods under conditions promoting microorganism growth until
        (i) the threshold value is achieved, and thereafter performing step (a); or
        (ii) a maximum of 18 hours has transpired without the threshold value being achieved and no further assays are performed.
115. The method of embodiment 114, wherein at least one assay is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.
116. The method of embodiment 114, wherein each of the assays is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.
117. The method of embodiment 116, wherein the metabolic probe comprises 7-hydroxy-10-oxidophenoxazin-10-ium-3-one (resazurin).
118. The method of embodiment 116, wherein the surface-binding probe comprises a coordination complex of a lanthanide with diethylenetriaminetetraacetic acid or a cryptate ligand.
119. The method of embodiment 118, wherein the surface-binding probe comprises

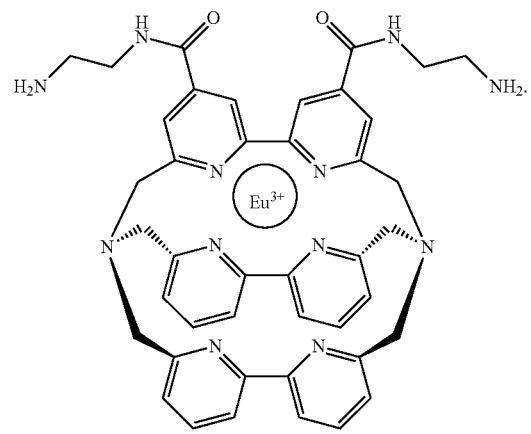

120. The method of embodiment 118, wherein the surface binding probe comprises europium, strontium, terbium, samarium, and dysprosium, or a combination thereof.
121. The method of embodiment 114, wherein the plurality of assays for determining microorganism growth comprises (a) nucleic acid amplification, (b) nucleic acid sequencing, (c) use of adenosine triphosphate, (d) light scattering, (e) optical microscopy, or (f) measuring microorganism mass.
122. The method of embodiment 114, wherein the different growth assays are performed (a) sequentially (b) or concurrently.
123. The method of embodiment 114, wherein at least one well of the panel is a checkpoint assay well comprising one of:
    (a) a growth indicator during the initial incubation period and/or additional incubation period; and/or
    (b) no growth indicator, wherein the checkpoint assay is performed by absorbance, nephelometry, mass resonance, or acoustically.
124. The method of embodiment 114, wherein at least one well of the panel is a checkpoint assay well and does not comprise antimicrobials.

125. The method of embodiment 124, wherein the checkpoint assay wells that do not comprise antimicrobials are different from the positive control wells for the one or more AST assays that does not comprise antimicrobials.

126. The method of embodiment 114, wherein the threshold value comprises a value dependent on the microorganism.

127. The method of embodiment 71, wherein the microorganisms are bacteria, fungi, protozoa, and/or archaea.

128. The method of embodiment 127, wherein the bacteria are selected from the group consisting of *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardnerella* spp., *Haemophilus* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., and combinations thereof.

129. The method of embodiment 127, wherein the fungi are selected from the group consisting of *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp., *Sporothrix, Exserohilum, Cladosporium,* ringworm, mucormycetes, and combinations thereof.

130. The method of embodiment 71, wherein the sample is one or more inoculates derived from samples selected from blood, cerebrospinal fluid, urine, stool, vaginal, sputum, bronchoalveolar lavage, throat, nasal/wound swabs, and combinations thereof 131. The method of embodiment 130, wherein the sample is an unprocessed raw biological sample.

132. The method of embodiment 130, wherein the sample is a processed biological sample.

133. The method of embodiment 71, wherein a signaling agent is associated with one or more binding moieties capable of binding directly or indirectly to the intact microorganisms.

134. The method of embodiment 71, wherein A is one or more of, but not limited to, the following: Amikacin, Amikacin-fosfomycin, Amoxicillin, Amoxicillin-clavulanate, Ampicillin, Ampicillin-sulbactam, Azithromycin, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Voriconazole and a salt or hydrate form thereof.

135. The method of embodiment 71, wherein the antimicrobial is vancomycin.

136. A rapid method of determining a qualitative susceptibility of a microbe-containing sample to an antimicrobial, comprising the steps of:
inoculating at least two reference wells of an assay panel comprising a plurality of fluid wells with a first quantity of the microbe-containing sample;
inoculating at least one experimental well of the assay panel with a second quantity of the microbe-containing sample, the experimental well comprising a quantity of the antimicrobial;
storing the assay panel under conditions that promote microbial growth;
interrogating a first reference well of the panel to assess a level of microbial growth, and if the assessed level of growth exceeds a predetermined threshold,
measuring a signal from the at least one experimental well and a second reference well, wherein the signal is proportional to one of a microbial surface area or a microbial metabolic process;
based on the signal measured in the second reference well, determining a cutoff value for a signal measured in the experimental well, and comparing the signal measured in the experimental well to the cutoff value; and
determining, based on said comparing, the qualitative susceptibility of the microbe-containing sample to the antimicrobial.

These and other features and advantages of the present disclosure will be readily apparent from the following detailed description, the scope of the claimed invention being set out in the appended claims.

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

DESCRIPTION OF FIGURES

The detailed description will be better understood in conjunction with the accompanying drawings, wherein like reference characters represent like elements, as follows.

Figure 1:
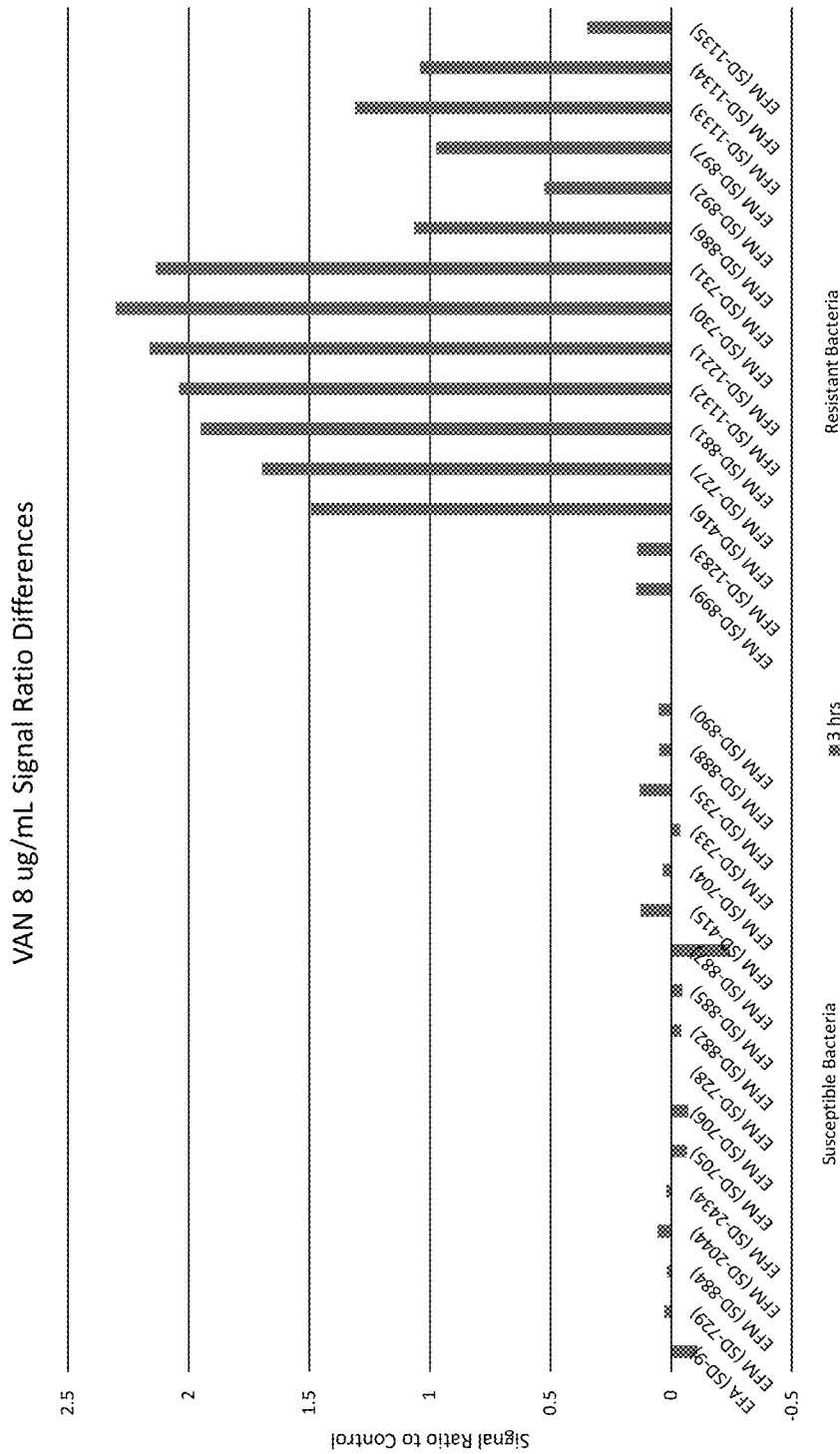
FIG. 1. Depiction of the difference of the ratios of fluorescent signal in wells containing vancomycin to uninoculated control wells at 4 and 3 hours following inoculation.

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. In the figures, identical or nearly identical or equivalent elements are typically represented by the same reference characters. For purposes of clarity and simplicity, not every element of each embodiment is shown where illustration is not necessary to allow those of ordinary skill in the art to understand the disclosure.

DETAILED DESCRIPTION

The following detailed description should be read with reference to the drawings, which, as noted above, depict illustrative embodiments. It will be appreciated that the present disclosure is set forth in various levels of detail in this application. In certain instances, details that are not necessary for one of ordinary skill in the art to understand the disclosure, or that render other details difficult to perceive may have been omitted. All of the compositions, systems and/or methods disclosed and claimed herein can be made and executed without undue experimentation in light of the present disclosure. It should be understood that the claimed subject matter is not necessarily limited to the particular embodiments or arrangements described or illustrated herein, the scope of the claimed invention being set out in the appended claims.

Definitions

The term "biological sample" refers to any sample that contains a microorganism, e.g., a bacterium and a fungal cell. Exemplary biological samples include, but are not limited to, whole blood, plasma, serum, sputum, urine, stool, white blood cells, red blood cells, buffy coat, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchoalveolar lavage, bronchial lavage, or pulmonary lavage, lung aspirates, and organs and tissues, including but not limited to, liver, spleen, kidney, lung, intestine, brain, heart, muscle, pancreas, and the like, swabs (including, without limitation, wound swabs, buccal swabs, throat swabs, vaginal swabs, urethral swabs, cervical swabs, rectal swabs, lesion swabs, abscess swabs, nasopharyngeal swabs, and the like), and any combination thereof. Also included are bacteria cultures or bacteria isolates, fungal cultures or fungal isolates. The ordinary-skilled artisan will also appreciate that isolates, extracts, or materials obtained from any of the above exemplary biological samples are also within the scope of this disclosure.

As used herein, the terms "infection" and "infectious agent" are meant to include any infectious agent of a microbial origin, e.g., a bacterium, a fungal cell, an archaeon, and a protozoan. In preferred examples, the infectious agent is a bacterium, e.g., a gram-positive bacterium, a gram-negative bacterium, and an atypical bacteria. The term "antimicrobial resistant microorganism" is a microorganism (e.g., bacterium, fungus, archaeon, and protozoan) that is resistant to one or more distinct antimicrobials, i.e., anti-bacterial drugs, antifungal drugs, anti-archaea medications, and anti-protozoan drugs.

"Microorganisms" as used in this specification refers to e.g., a liquid suspension of microorganisms, and may include one strain of microorganism, or more than one strain of microorganism. The microorganisms may include one species of microorganism. The microorganisms may include more than one strain of microorganism. The microorganisms may include one order of microorganism. The microorganisms may include one class of microorganism. The microorganisms may include one family of microorganism. The microorganisms may include one kingdom of microorganism.

The microorganism may be a bacterium. Examples of bacterium include and are not limited to *Acetobacter aurantius, Acinetobacter bitumen, Acinetobacter* spp., *Actinomyces israelii, Actinomyces* spp., *Aerococcus* spp., *Agrobacterium radiobacter, Agrobacterium tumefaciens, Anaplasma, Anaplasma phagocytophilum, Azorhizobium caulinodans, Azotobacter vinelandii, Bacillus, Bacillus anthracis, Bacillus brevis, Bacillus cereus, Bacillus fusiformis, Bacillus licheniformis, Bacillus megaterium, Bacillus mycoides, Bacillus* spp., *Bacillus stearothermophilus, Bacillus subtilis, Bacillus Thuringiensis, Bacteroides, Bacteroides fragilis, Bacteroides gingivalis, Bacteroides melaninogenicus* (also known as *Prevotella melaninogenica*), *Bartonella, Bartonella henselae, Bartonella quintana, Bartonella* spp., *Bordetella, Bordetella bronchiseptica, Bordetella pertussis, Bordetella* spp., *Borrelia burgdorferi, Brucella, Brucella abortus, Brucella melitensis, Brucella* spp., *Brucella suis, Burkholderia, Burkholderia cepacia, Burkholderia mallei, Burkholderia pseudomallei, Calymmatobacterium granulomatis, Campylobacter, Campylobacter coli, Campylobacter fetus, Campylobacter jejuni, Campylobacter pylori, Campylobacter* spp., *Chlamydia, Chlamydia* spp., *Chlamydia trachomatis, Chlamydophila, Chlamydophila pneumoniae* (previously called *Chlamydia pneumoniae*), *Chlamydophila psittaci* (previously called *Chlamydia psittaci*), *Chlamydophila* spp., *Clostridium, Clostridium botulinum, Clostridium*

*difficile, Clostridium perfringens* (previously called *Clostridium welchii*), *Clostridium* spp., *Clostridium tetani, Corynebacterium, Corynebacterium diphtheriae, Corynebacterium fusiforme, Corynebacterium* spp., *Coxiella burnetii, Ehrlichia chaffeensis, Ehrlichia* spp., *Enterobacter cloacae, Enterobacter* spp., *Enterococcus, Enterococcus avium, Enterococcus durans, Enterococcus faecalis, Enterococcus faecium, Enterococcus gallinarum, Enterococcus maloratus, Enterococcus* spp., *Escherichia coli, Francisella* spp., *Francisella tularensis, Fusobacterium nucleatum, Gardnerella* spp., *Gardnerella vaginalis, Haemophilus* spp., *Haemophilus, Haemophilus ducreyi, Haemophilus influenzae, Haemophilus parainfluenzae, Haemophilus pertussis, Haemophilus vaginalis, Helicobacter pylori, Helicobacter* spp., *Klebsiella pneumoniae, Klebsiella* spp., *Lactobacillus, Lactobacillus acidophilus, Lactobacillus bulgaricus, Lactobacillus casei, Lactobacillus* spp., *Lactococcus lactis, Legionella pneumophila, Legionella* spp., *Leptospira* spp., *Listeria monocytogenes, Listeria* spp., *Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium* spp., *Mycobacterium tuberculosis, Mycoplasma, Mycoplasma fermentans, Mycoplasma genitalium, Mycoplasma hominis, Mycoplasma penetrans, Mycoplasma pneumoniae, Mycoplasma* spp., *Neisseria, Neisseria gonorrhoeae, Neisseria meningitidis, Neisseria* spp., *Nocardia* spp., *Pasteurella, Pasteurella multocida, Pasteurella* spp., *Pasteurella tularensis, Peptostreptococcus, Porphyromonas gingivalis, Prevotella melaninogenica* (previously called *Bacteroides melaninogenicus*), *Proteus* spp., *Pseudomonas aeruginosa, Pseudomonas* spp., *Rhizobium radiobacter, Rickettsia, Rickettsia prowazekii, Rickettsia psittaci, Rickettsia quintana, Rickettsia rickettsii, Rickettsia* spp., *Rickettsia trachomae, Rochalimaea, Rochalimaea henselae, Rochalimaea quintana, Rothia dentocariosa, Salmonella, Salmonella enteritidis, Salmonella* spp., *Salmonella typhi, Salmonella typhimurium, Serratia marcescens, Shigella dysenteriae, Shigella* spp., *Spirillum volutans, Staphylococcus, Staphylococcus aureus, Staphylococcus epidermidis, Staphylococcus* spp., *Stenotrophomonas maltophilia, Stenotrophomonas* spp., *Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oxalis, Streptococcus pneumoniae, Streptococcus pyogenes, Streptococcus rattus, Streptococcus salivarius, Streptococcus sanguis, Streptococcus sobrinus, Streptococcus* spp., *Treponema, Treponema denticola, Treponema pallidum, Treponema* spp., *Ureaplasma* spp., *Vibrio, Vibrio cholerae, Vibrio comma, Vibrio parahaemolyticus, Vibrio* spp., *Vibrio vulnificus, viridans* streptococci, *Wolbachia, Yersinia, Yersinia enterocolitica, Yersinia pestis, Yersinia pseudotuberculosis*, and *Yersinia* spp.

The microorganism may be a fungus. Examples of fungi include and are not limited to *Aspergillus* spp., *Blastomyces* spp., *Candida* spp., *Cladosporium, Coccidioides* spp., *Cryptococcus* spp., *Exserohilum, fusarium, Histoplasma* spp., *Issatchenkia* spp., mucormycetes, *Pneumocystis* spp., ringworm, *Scedosporium, Sporothrix*, and *Stachybotrys* spp.

The microorganism may be a protozoan. Examples of protozoan include and are not limited to *Entamoeba histolytica, Plasmodium* spp., *Giardia lamblia*, and *Trypanosoma brucei*.

The terms "kits" and "systems," as used herein in the present disclosure, are intended to refer to such things as combinations of multiple signaling agents with one or more other types of elements or components (e.g., other types of biochemical reagents, signal detection reagents, controls (i.e., positive and negative controls, e.g., chemically sensitive/resistant microorganisms), separation means (e.g., filters and magnetic beads), containers, packages such as packaging intended for commercial sale, substrates/cartridges to which microorganism suspensions can be cultured, processed, or contained, electronic hardware components, and software recorded on a non-transitory processor-readable medium). Certain embodiments of this disclosure relate to kits for Rapid AST, for MIC or QSR determinations, etc.

The term "panel," refers to an arrangement of fluid wells configured to permit the performance of a multivariate or multiplex microbial assay. Panels used in the present disclosure, for example, may be dedicated to rapid AST determinations, and may include one or more positive control wells (e.g., wells for growth checkpoint assays) and a series of experimental wells defining, e.g., one or more dilution series for an antimicrobial being examined, and/or wells that allow for variation of other conditions such as media conditions, etc. Panels may be embodied on consumables, such as AST cassettes, multi-well plates, etc. The terms "well," and "reservoir" are used interchangeably to refer to the fluid wells of a panel or consumable.

Overview

Embodiments of the present disclosure relate to the novel finding that the accuracy of rapid AST results can be improved by utilizing different microorganism concentrations for AST. This represents a significant departure from the broth microdilution standard and from existing AST assay platforms, which reflect significant efforts in equipment and consumables design to ensure an approximately equal volume and/or number of microorganisms is inoculated into each reservoir on each panel, with the exception of negative, contamination control reservoirs.

The CLSI M07 manual follows the broth microdilution definition in the International Organization for Standardization (ISO) 16782 standard *Clinical laboratory testing—Criteria for acceptable lots of dehydrated Mueller-Hinton agar and broth for antimicrobial susceptibility testing* in defining that "Each well [other than contamination controls] should contain approximately $5 \times 10^5$ colony forming units (CFU)/mL (range, $2\text{-}8 \times 10^5$ CFU/mL)." The M07 further describes "The most convenient method for preparing microdilution trays is by using a dispensing device . . . [which] delivers 0.1 (±0.02) mL into each of the 96 wells of a standard tray."

Automated and semi-automated systems are thus designed to provide approximately equal concentrations of microbe to each reservoir of a panel. For example, the Vitek® 2 (bioMerieux) and Phoenix™ (Becton-Dickinson) platforms use capillary forces in custom cartridges to fill a plurality of reservoirs with approximately the same concentration of microbes and the MicroScan™ (Danaher/Beckman-Coulter) and SensiTitre™ (Thermo Fisher) platforms provide custom inoculators.

In cases of slowly induced- and/or hetero-resistance, it may be challenging to differentiate the absence of growth resulting from such resistance mechanisms from the absence of growth resulting from true susceptibility. To meet this challenge, automated systems either follow the reference standards and wait approximately 18 or more hours (or, in some cases for vancomycin, 24 or more hours), as is the case for the MicroScan and the SensiTitre, or regularly assess growth in each reservoir and perform algorithmic interrogations to determine relative growth trends across each dilution, as is the case for the Vitek2 and Phoenix.

This latter approach typically requires longer times for AST determinations for microbes exhibiting slowly induced- and/or hetero-resistance mechanisms, resulting in slower results being delivered for patients infected with pathogens that may not respond to standard broad-spectrum therapies. Furthermore, as described in U.S. Patent Application Publication 2020-0149086 (which is incorporated by reference herein), repetitive growth measurements of every reservoir on each panel restrict the number of reservoirs that can be present and thereby limit the number of antimicrobial agents that can be tested in parallel.

However, the inventors have discovered that accurate AST determinations for a plurality of microbial strains, including those harboring slowly induced- and/or hetero-resistance, may be achieved by performing growth determinations using two or more microorganism concentrations. For example, if a microorganism concentration of approximately $C_{m0}$ is inoculated into each reservoir of a dilution series of an antimicrobial, this new method teaches that the inoculation into each of an additional two or more reservoirs of a concentration of $\geq 5 \times C_{m0}$ of the same microorganism, termed high microorganism load reservoirs (HMLRs), can improve the accuracy with which rapid AST determinations can be made.

The methods used to perform growth determinations in the dilution reservoirs and HMLRs may be similar or different. Growth in a plurality of dilution reservoirs may be assessed by metabolic (as described in U.S. Patent Application Publication 2020-0149086) and/or surface area (as described in U.S. Pat. No. 9,834,808) assays after the performance of a sufficient growth assay (as described in U.S. patent application Ser. No. 16/472,714). Growth in HMLRs may be assessed with a viability probe in parallel with the sufficient growth assay.

In the context of rapid AST assays such as those described by the inventors in, e.g., U.S. Pat. No. 9,834,808, which is incorporated by reference in its entirety, the use of HMLRs may facilitate the goal of providing single-shift AST results.

Figures 3A, 3B:
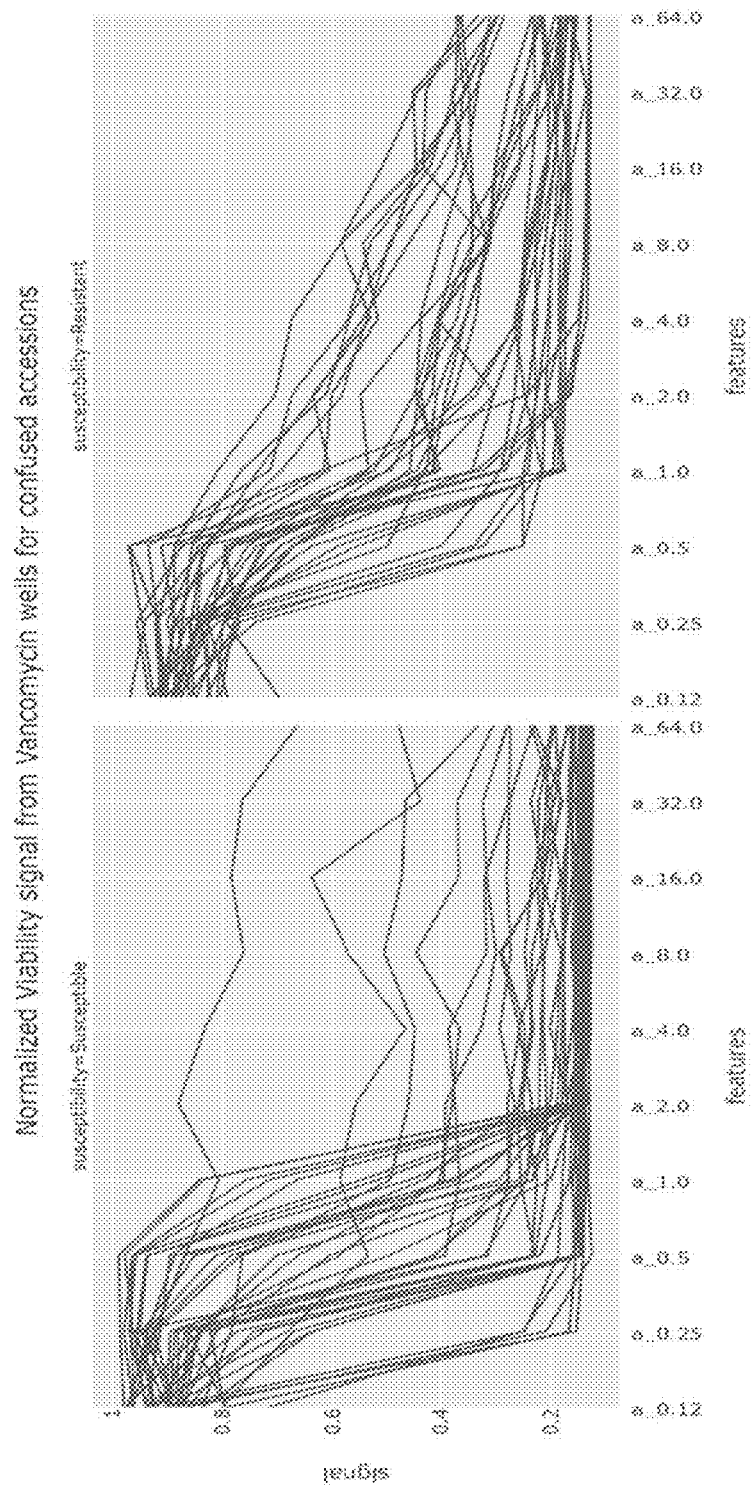
FIGS. 3A and 3B. Depiction of the normalized viability signal from Vancomycin wells for confused accessions.

The inventors have examined dose-response relationships of reference microbial strains that are known to be susceptible to, or resistant to, vancomycin. FIG. 3, depicts, for individual susceptible (panel A) or resistant (Panel B) reference strains, fluorescence signals observed across a representative vancomycin dilution series. The figure shows that, for many susceptible strains, the dose curves overlap with those of resistant strains, preventing consistent differentiation therebetween.

Figure 4:
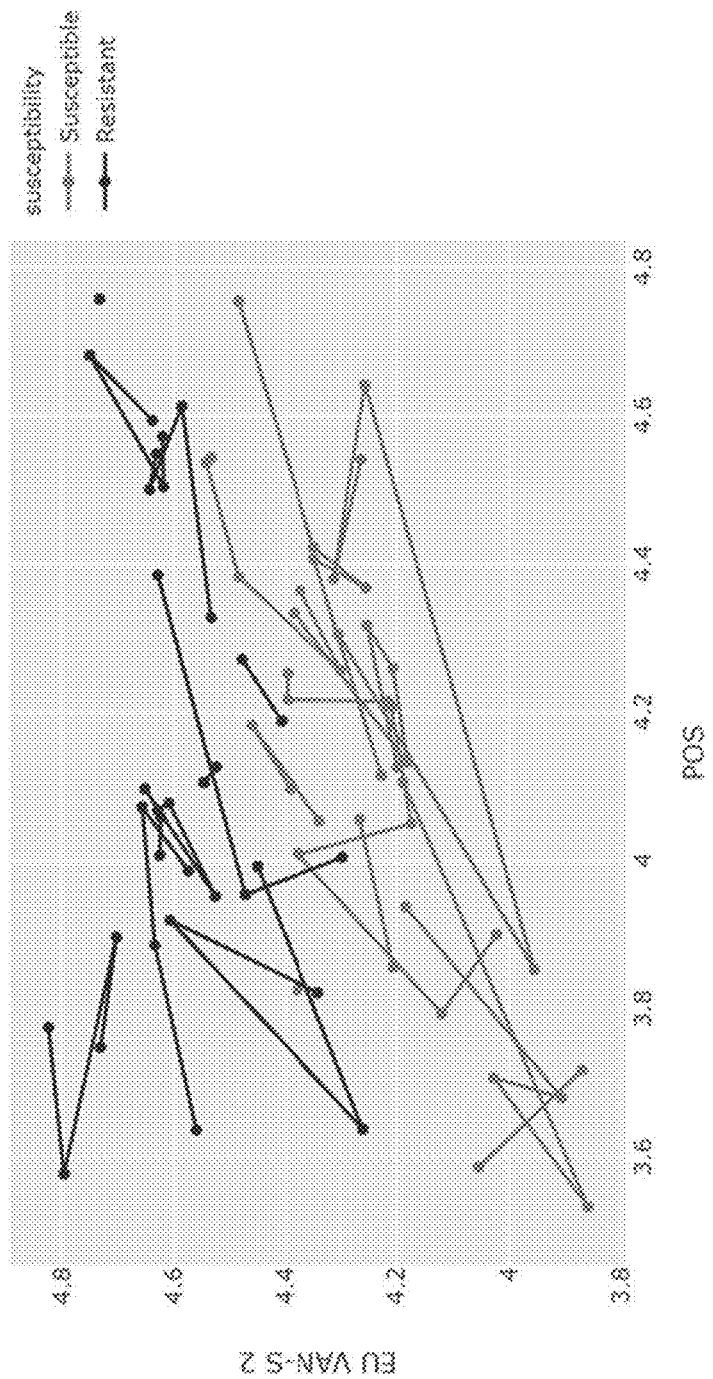
FIG. 4. Depiction of the clustering of signals measured in positive control wells comprising no antimicrobial, inoculated with a first quantity of microbe-containing sample $C_{m0}$, and signals measured in experimental HMLR wells comprising 4 µg/mL vancomycin within the range of the AST dilution series.

By increasing the number of cells being interrogated, however, susceptible and resistant samples can be clearly delineated. FIG. 4 shows, for individual reference strains, the clustering of (x) signals measured in positive control wells comprising no antimicrobial, inoculated with a first quantity of microbe-containing sample $C_{m0}$, and (y) signals measured in experimental HMLR wells comprising a concentration of vancomycin within the range of the AST dilution series, in this case 4 μg/mL. For each strain, multiple measurements were taken on multiple days to determine the ranges in which measurements cluster. As the figure demonstrates, the resistant reference strains tend to cluster at higher HMLR signal values than susceptible strains that cluster around similar positive control signal values.

Based on this finding, the inventors have determined that a series of threshold values, or a threshold function, can be used to differentiate between resistant and susceptible samples. For example, in certain methods of this disclosure, a positive control signal of an AST panel is used to select an HMLR cutoff value, and measured HMLR signals above the cutoff value are called as resistant while those below the cutoff are called susceptible. HMLR cutoff values can be pre-determined and stored in a look-up table or database, or may be determined at the time of each measurement by a function, formula, or mathematical model.

In the context of rapid AST panels, some embodiments of this disclosure relate to an AST panel comprising one or more dedicated HMLR wells. Methods utilizing such a panel will typically include inoculating a larger volume of patent-sample derived and/or microorganism-containing fluid into each HMLR well than is inoculated into the non-HMLR wells of the AST panel; the HMLR wells may then receive a smaller volume of other fluids such as microbial broths or buffers, or they may receive concentrated solutions to equalize concentrations of, e.g., nutrients or antimicrobials with those of the non-HMLR wells. Alternatively, similar fluid volumes are inoculated into both HMLR and non-HMLR wells, but the HMLR wells receive fluids with higher microbial concentrations.

Signals from the HMLR and non-HMLR wells may be based on, e.g., surface area measurements as described in [808 patent], or measurements of metabolic activity.

Broth microdilution AST determinations for an antimicrobial agent, A, are performed by assessing relative growth in each of a range of different concentrations of A, spanning from a low concentration $C_{AL}$ to a high concentration $C_{AH}$. The microorganism concentration is, by definition, held constant at $C_{m0}=2-8\times10^5$ CFU/mL. The value of $C_{AL}$ is typically less than or equal to the lowest susceptible breakpoint concentration for the organisms for which the panel is designed to test and the jurisdiction where the panel is designed to be used (ie. US, Europe, etc.). The value of $C_{AH}$ is typically greater than or equal to the highest resistant breakpoint concentration for the organisms for which the panel is designed to test and the jurisdiction where the panel is designed to be used (ie. US, Europe, etc.). In some cases, such as where no resistant breakpoint exists, the value of $C_{AH}$ may alternately be greater than or equal to the intermediate or susceptible breakpoint.

A typical dilution series from $C_{AL}$ to $C_{AH}$ may span 3-15 independent reservoirs, each with a different concentration of antimicrobial A. These may be doubling (serial) dilutions, as detailed in the ISO and CLSI standards or may be non-twofold dilutions. Dilution series may be comprised of a combination of doubling dilutions and non-twofold dilutions. The number of dilutions is dependent upon the drug and the species supported for testing with the panel.

It may be advantageous, in certain embodiments, for a minimum of one high microorganism load reservoir (HMLR) to be utilized together with a control comprising no microorganisms and no antimicrobial. The HMLR reservoir comprises antimicrobial A at a concentration $\geq C_{AL}/4$, preferably $\geq C_{AL}$, and a microorganism concentration $\geq 2\times C_{m0}$, preferably $\geq 5\times C_{m0}$. Additional HMLR reservoirs may also be present. These may comprise, for example, additional reservoirs at the same concentration of A and/or additional reservoirs at different concentrations of A. In some cases, the HMLRs comprise a microorganism concentration $\geq 3\times C_{m0}$, $\geq 4 \times C_{m0}$, $\geq 5 \times C_{m0}$, $\geq 6 \times C_{m0}$, $\geq 7 \times C_{m0}$, $\geq 8 \times C_{m0}$, $\geq 9 \times C_{m0}$, $\geq 10 \times C_{m0}$, $\geq 11 \times C_{m0}$, $\geq 12 \times C_{m0}$, $\geq 13 \times C_{m0}$, $\geq 14 \times C_{m0}$, $\geq 15 \times C_{m0}$, $\geq 16 \times C_{m0}$, $\geq 17 \times C_{m0}$, $\geq 18 \times C_{m0}$, $\geq 19 \times C_{m0}$, or $\geq 20 \times C_{m0}$.

In an embodiment, growth in the HMLR(s) and HMLR control(s) is assessed with a probe capable of associating with microorganism surfaces. The present disclosure permits rapid determination of antibiotic susceptibility of microbial infections. This disclosure is based in part upon the surprising discovery of non-specific surface binding assays that provide accurate and rapid Antimicrobial Susceptibility Testing (AST) determinations in fewer than twelve hours—and, specifically, under four hours. The present disclosure ("Fast-AST") provides accurate results that are consistent with results obtained using the Clinical Laboratory Standards Institute (CLSI) reference methods when tested with multiple antimicrobials and on a plurality of microorganisms; however, the present disclosure takes significantly less time to obtain results than the CLSI methods. Moreover, the present disclosure accurately differentiates an antimicrobial's MIC for clinically-relevant microbial strains that are resistant to one or more antimicrobials and the antimicrobial's MIC for strains of the same microorganism that are sensitive to the antimicrobials. Furthermore, the present disclosure may include signaling agents (e.g., Europium compounds) that are bound to microorganisms non-specifically rather than specifically (e.g., via chemically conserved groups or biochemically conserved binding sites on microorganisms), thereby expanding the generalization of the present disclosure to any microorganism and allowing onset of an appropriate treatment without first needing to identify the particular infectious microorganism. Also, the present disclosure permits signal amplification such that microbes may be rapidly detected at lower concentrations, e.g., from a dilute culture of microorganisms or via a patient's biological sample. Additionally, the present disclosure may use Europium formulations as chemical moiety, thereby expanding the dynamic range of the methods and allowing for more accurate determinations from a range of microbial samples. Finally, the present disclosure is compatible with existing equipment, thereby enabling rapid adoption in current clinical laboratories. Accordingly, the present disclosure, in a greatly reduced amount of time and expense, relative to standard methods, can provide a patient with an appropriate treatment regimen, i.e., a specific antimicrobial and at a particular dosage. Thus, the present disclosure will improve patient outcomes, lower hospital costs, and help reduce further evolution of antimicrobial resistant microorganisms; thus, the present disclosure represents a significant breakthrough in the AST field.

An aspect of the present disclosure is a method for determining antimicrobial susceptibility of microorganisms. The method includes steps of incubating a liquid suspension of microorganisms in the presence of an antimicrobial and a signaling agent, which is capable of binding to a surface of the microorganisms, under conditions that promote growth of the microorganisms; separating the microorganisms bound by the signaling agent from the unbound signaling agent; and determining signal levels associated with the microorganisms as compared to one or more controls.

Another aspect of the present disclosure is a method for determining antimicrobial susceptibility of microorganisms. The method includes steps of incubating a liquid suspension of microorganisms in the presence of an antimicrobial under conditions that promote growth of the microorganisms; adding a signaling agent capable of binding to a surface of the microorganisms; separating the microorganisms bound by the signaling agent from the unbound signaling agent; and determining signal levels associated with the microorganisms as compared to one or more controls.

Yet another aspect of the present disclosure is a method for determining antimicrobial susceptibility of microorganisms. The method includes steps of incubating a liquid suspension of microorganisms in a cartridge including a plurality of chambers, each chamber containing one or more antimicrobials, under conditions that promote growth of the microorganisms; adding a signaling agent, which is capable of binding to a surface of the microorganisms, to the plurality of chambers; removing unbound signaling agent; and determining signaling levels in the plurality of chambers as compared to one or more controls.

An aspect of the present disclosure is a method for determining antimicrobial susceptibility of microorganisms. The method includes incubating microorganisms in the presence of an antimicrobial and a signaling agent, which includes a signal amplifier and one or more chemical moieties capable of binding non-specifically to a surface of the microorganisms, under conditions that promote growth of the microorganisms; separating the microorganisms bound by the signaling agent from the unbound signaling agent; and determining signal levels associated with the microorganisms as compared to one or more controls.

Another aspect of the present disclosure is a method for determining antimicrobial susceptibility of microorganisms. The method includes incubating microorganisms in the presence of an antimicrobial under conditions that promote growth of the microorganisms; adding a signaling agent including a signal amplifier and one or more chemical moieties capable of binding non-specifically to a surface of the microorganisms; separating the microorganisms bound by the signaling agent from the unbound signaling agent; and determining signal levels associated with the microorganisms as compared to one or more controls.

Yet another aspect of the present disclosure is a kit for determining antimicrobial susceptibility of microorganisms. The kit includes a signaling agent capable of binding to a surface of the intact microorganisms of interest; a solution for incubating a sample containing microorganisms; and one or more reagents for generating signals from the signaling agent.

In an embodiment, growth in the HMLR(s) and HMLR control(s) is assessed through the addition of one or more metabolic (viability) probes prior to a plurality of the incubation period. It is most preferred that the metabolic probe be added to the reservoirs following panel inoculation and prior to the onset of panel incubation. Suitable probes are detailed in U.S. Patent Application Publication 2020-0149086 at paragraphs [0211] through [0237], which is incorporated in its entirety herein. This probe may comprise resazurin and methylene blue together with ferric and ferrous salts. The probe may further comprise 1-methoxy-5-methylphenasinum methyl sulfate. In alternative embodiments, growth may be assessed by any number of methods including, but not limited to, absorbance, scattering, thermal measurements, mass measurements, electrical measurements.

In an embodiment, growth in the HMLR(s) is normalized by growth in the HMLR control(s). The HMLR growth or the normalized HMLR growth may then be evaluated based on the rate of growth of the strain. Strain growth rate may be determined based upon one or more positive control reservoirs inoculated with a microorganism concentration of $C_{m0}$. Growth in these reservoirs may be assessed by one or more of Europium and viability probes.

In an embodiment, the addition of the viability and Europium probes is performed following the performance of a sufficient growth assay. An exemplary method of this disclosure comprises the following steps:

introducing suspensions of one or more microorganisms to a cartridge comprising a plurality of chambers, wherein a plurality of chambers comprise one or more antimicrobial agents;

incubating the cartridge under conditions promoting microorganism growth for an initial incubation period;

performing in a subset of the cartridge chambers, one or more checkpoint assays to determine if microorganism growth has achieved a threshold value; and (a) if the threshold value is achieved, performing a plurality of different growth assays in a plurality of the cartridge chambers to determine the microorganism's susceptibility to the one or more antimicrobials, and obtaining a minimum inhibitory concentration (MIC) and/or a qualitative susceptibility result (QSR); or (b) if the threshold value is not achieved, performing one or more additional incubation periods under conditions promoting microorganism growth until (i) the threshold value is achieved, and thereafter performing step (a); or (ii) a maximum of 18 hours has transpired without the threshold value being achieved and no further assays are performed.

In one aspect, a method of determining antimicrobial susceptibility of one or more microorganisms is provided, where the method comprises performing a growth assay comprising: incubating a suspension of a microorganism in the presence of one or more antimicrobials without a metabolic probe present; introducing a metabolic probe in an aqueous-miscible solvent after the incubation of the one or more microorganisms; and determining antimicrobial susceptibility of the one or more microorganisms based on relative microorganism growth.

In some embodiments, the method for determining antimicrobial susceptibility of one or more microorganisms comprises incubating a suspension of microorganisms in a plurality of chambers in a cartridge comprising antimicrobial agents for an initial time period to promote microorganism growth, performing one or more checkpoint assays in a subset of the cartridge chambers to determine if relative microorganism growth achieved a threshold value, wherein achieving the threshold value indicates a sufficient growth for the assay system to provide MIC or QSR data for the microorganism, then performing the assay for obtaining the MIC or QSR data.

In an embodiment, the fluorescent or absorbent signal resulting from resazurin reduction is then determined in the HMLR and HMLR control reservoirs at a minimum of two timepoints, preferably after 60-240 minutes of incubation, timepoint $T_1$, and then after a further 30-120 minutes of incubation, timepoint $T_2$. As one example, $T_1$ is approximately 180 minutes and $T_2$ is approximately 60 minutes.

In an embodiment, the HMLR assay is performed by comparing the optical signal at $T_1$ with that at $T_2$ after normalization with a control signal such as the HMLR control reservoir signal. The absolute value of the signal may also be used for interpretation. An optical signal at $T_2$ is greater than that at $T_1$ is indicative of continued microorganism growth at antimicrobial concentration A. An optical signal at $T_2$ is less than or equal to that at $T_1$ suggests that microorganism growth has subsided.

Surface Area Measurements for Rapid AST

Some embodiments of this disclosure relate to Rapid AST methods utilizing specific or non-specific surface area binding agents to measure the aggregate surface area of cells grown under varying conditions such as multiple antimicrobial agents or multiple concentrations of the same. Accordingly, one aspect of the present disclosure relates to s a method for determining antimicrobial susceptibility of microorganisms. The method includes steps of incubating a liquid suspension of microorganisms in the presence of an antimicrobial and a signaling agent under conditions that promote growth of the microorganisms, wherein the signaling agent is capable of binding to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms.

Another aspect of the present disclosure is a method for determining antimicrobial susceptibility of microorganisms. The method includes steps of incubating a liquid suspension of microorganisms in the presence of an antimicrobial under conditions that promote growth of the microorganisms; adding a signaling agent capable of binding to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms. In embodiments, adding the signaling agent occurs prior to or during the incubating step or adding the signaling agent occurs after the incubating step.

Another aspect of the present disclosure is a method for determining antimicrobial susceptibility of microorganisms. The method includes steps of incubating a liquid suspension of microorganisms in a cartridge comprising a plurality of chambers, each chamber containing one or more antimicrobials, under conditions that promote growth of the microorganisms; adding a signaling agent to the plurality of chambers, wherein the signaling agent is capable of binding to a surface of the microorganisms; removing unbound signaling agent; and determining signaling levels in the plurality of chambers as compared to one or more controls, thereby determining the susceptibility of microorganisms to the one or more antimicrobials. In embodiments, the cartridge further includes one or more control chambers (e.g., at least 2, 4, 6, 8, 12, 24, 48, 96, 192, 384, 1536 or more chambers) that do not contain antimicrobials or one or more antimicrobials for which the microorganisms are not susceptible.

In embodiments of an above aspect, binding to a surface of the microorganisms is non-specific, e.g., comprising a non-covalent interaction and via forming a covalent bond.

In embodiments of an above aspect, the signaling agent may include a chemical and/or biochemical group capable of binding a surface of the microorganisms, wherein the surface comprises one or more of membranes, walls, proteins, organelles, saccharides, lipids, cell envelope, and/or nucleic acids.

In embodiments of an above aspect, the signaling agent may include a chemical and/or biochemical group capable of binding a biomolecule of the surface of the microorganisms, wherein the surface biomolecule is selected from peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof.

In embodiments of an above aspect, the signaling agent may include a signal amplifier and one or more chemical moieties capable of binding non-specifically to a surface of the microorganisms.

Another aspect of the present disclosure is a method for determining antimicrobial susceptibility of microorganisms. The method includes incubating microorganisms in the presence of an antimicrobial and a signaling agent under conditions that promote growth of the microorganisms, wherein the signaling agent comprises a signal amplifier and one or more chemical moieties capable of binding non-specifically to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms.

Another aspect of the present disclosure is a method for determining antimicrobial susceptibility of microorganisms. The method includes incubating microorganisms in the presence of an antimicrobial under conditions that promote growth of the microorganisms; adding a signaling agent comprising a signal amplifier and one or more chemical moieties capable of binding non-specifically to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms. In embodiments, the signaling agent occurs prior to, at the beginning of, or during the incubating step, preferably during the incubating step. In embodiments, the microorganisms are incubated in a liquid suspension.

In embodiments of an above aspect, the liquid suspension may be prepared by inoculating a liquid media with a microbial isolate grown from a biological sample.

In embodiments of an above aspect, the liquid suspension of microorganisms may be prepared from an unprocessed biological sample, e.g., an unprocessed biological sample has not undergone a culturing step.

In embodiments of an above aspect, the biological sample is selected from blood, cerebrospinal fluid, urine, stool, vaginal, sputum, bronchoalveolar lavage, throat, nasal/wound swabs, and a combination thereof.

In embodiments of an above aspect, the method does not involve a step of capturing microorganisms on a solid surface prior to or during incubation.

In embodiments of an above aspect, the method does not include a step of growing microorganisms on a solid surface during or subsequent to the incubating step.

In embodiments of an above aspect, the incubating may include agitating the liquid suspension of microorganisms.

In embodiments of an above aspect, the liquid suspension of microorganisms may be agitated by means of mechanical, acoustic, and/or magnetic agitation continuously or discretely during the incubating.

In embodiments of an above aspect, the incubating occurs at 31-37° C.

The present disclosure is superior to currently-used AST methods, in part because it provides accurate AST results in significantly less time. For instance, comparisons of the instant methods to currently used automated AST systems—BioMerieux's Vitek2, Beckman Dickinson's Phoenix, and Beckman-Coulter's MicroScan—are provided in U.S. Pat. No. 10,501,772 at column 20, line 30 through column 22, line 29 and FIGS. 3 and 4, which is incorporated by reference for all purposes.

Figure 5:
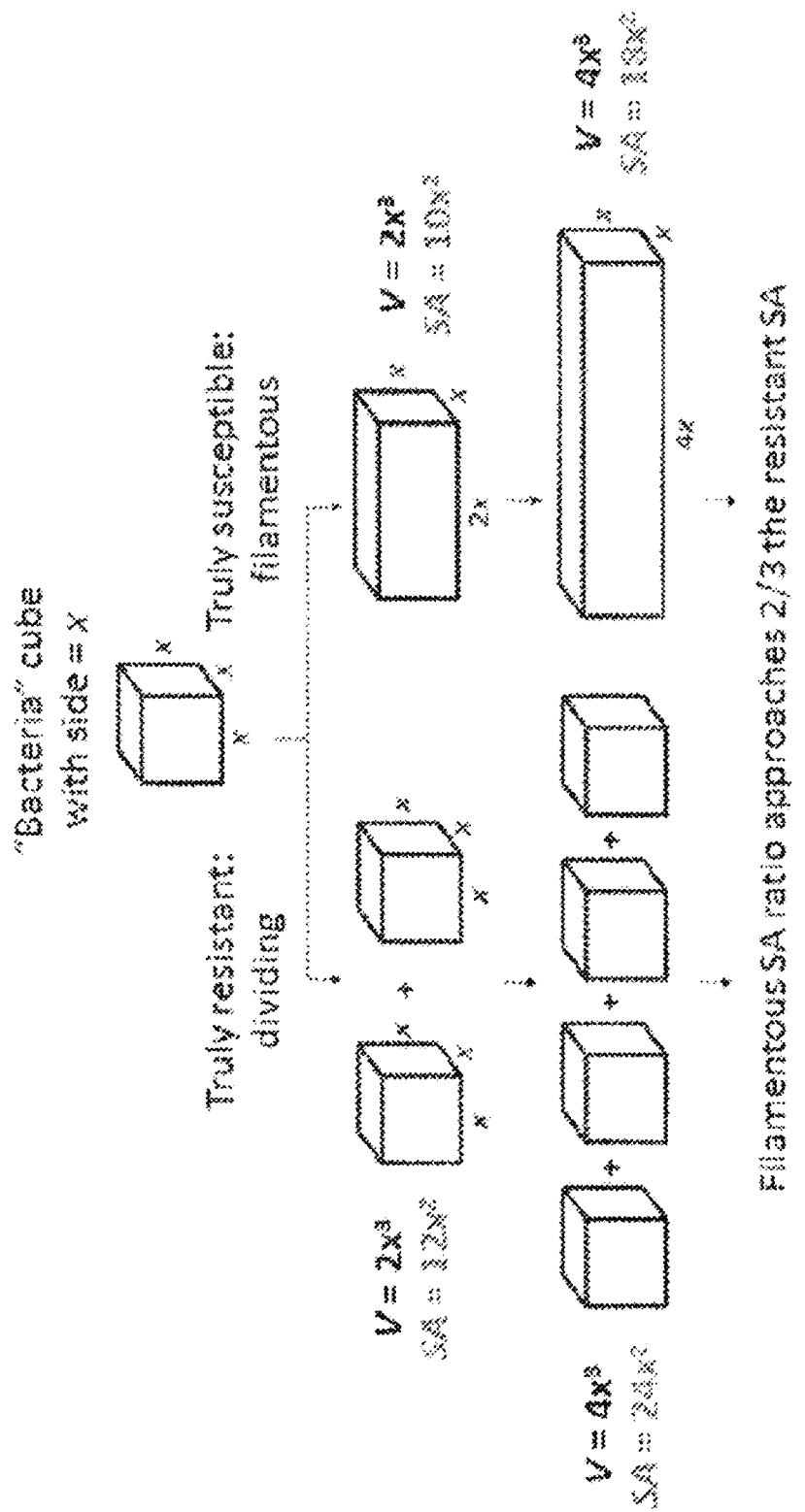
FIG. 5 is a schematic that illustrates the confounding effect that filamentous growth has on volumetric-based determinations of microorganism's antimicrobial susceptibilities. Susceptible bacteria entering filamentous growth may appear falsely resistant due to their increased volume.

Measurements of relative microorganism surface area, as used in the present disclosure, overcome the pitfalls of metabolic probes for AST. First, since relative surface area is not confounded by shifts in metabolic activity, fast-AST enables rapid, accurate resistance calls. Second, surface area measurements prevent over-resistance calls. In contrast to volumetric measurements obtained with metabolic probes of the currently-used AST systems, surface area measurements enable accurate differentiation between true resistance and filamentous growth. As illustrated in the schematic of FIG. 5, volumes of resistant and susceptible filamentous bacteria are difficult to distinguish. But the lack of septation creates a filamentous surface area significantly lower than that of truly resistant bacteria. Thus, by amplifying each bacteria's surface area, the present disclosure is able to accurately call four-hour, β-lactam (ampicillin) MICs for $E.\ coli$ samples (see, the below Examples). As illustrated in FIG. 5, the surface area differential between elongation and "true" resistance approaches ⅔, which may be detected with an amplified signal.

Another aspect of the present disclosure is a kit for determining antimicrobial susceptibility of microorganisms. The kit includes a signaling agent capable of binding to a surface of the intact microorganisms of interest; a solution for incubating a sample containing microorganisms; and one or more reagents for generating signals from the signaling agent.

In embodiments, the signaling agent is associated with one or more binding moieties capable of binding directly or indirectly to the intact microorganisms of interest.

In embodiments, this disclosure features a signaling agent capable of binding to the surface of a microorganism. In embodiments, said binding is non-specific. In embodiments, said binding is specific.

In embodiments, a signaling agent is present during an incubating step of a method described herein. In embodiments, a signaling agent is present after an incubating step of a method described herein.

In embodiments, binding comprises the formation of a covalent bond. In embodiments, a signaling agent is capable of binding to the surface of a microorganism, wherein said binding comprises the formation of a covalent bond. In embodiments, a method as described herein results in the formation of a covalent bond between a group on a microorganism surface (e.g., via a reactive group such as an electrophilic or nucleophilic group as described herein) and a signaling agent as described herein. In embodiments, a signaling agent has formed a covalent bond to the surface of a microorganism.

In embodiments, binding comprises the formation of a non-covalent interaction. In embodiments, a signaling agent is capable of binding to the surface of a microorganism, wherein said binding comprises the formation of a non-covalent interaction. In embodiments, a method as described herein results in the formation of non-covalent interaction between a group on a microorganism surface (e.g., via a reactive group such as an electrophilic or nucleophilic group as described herein) and a signaling agent as described herein. In embodiments, a signaling agent has formed a non-covalent interaction with the surface of a microorganism.

In embodiments, a non-covalent interaction comprises: ionic interaction, ion-ion interaction, dipole-dipole interaction, ion-dipole interaction, electrostatic interaction, London dispersion, van der Waals interaction, hydrogen bonding, π-π interaction, hydrophobic interaction, or any combination thereof. In embodiments, a non-covalent interaction is: ionic interaction, ion-ion interaction, dipole-dipole interaction, ion-dipole interaction, electrostatic interaction, London dispersion, van der Waals interaction, hydrogen bonding, π-π interaction, hydrophobic interaction, or any combination thereof.

In embodiments, a non-covalent interaction comprises ionic interactions, van der Waals interactions, hydrophobic interactions, π-π interactions, or hydrogen bonding, or any combination thereof. In embodiments, a non-covalent interaction comprises ionic interaction, van der Waals interaction, hydrogen bonding, or π-π interaction, or any combination thereof.

In embodiments, a signaling agent capable of binding to a microorganism's surface comprises a group (e.g., a chemical or biochemical group) capable of binding microorganism membranes, walls, proteins, organelles, saccharides, lipids, cell envelope, or nucleic acids, or any combination thereof. In embodiments, a signaling agent capable of binding to a microorganism's surface comprises a chemical group (e.g., a nucleophilic group or an electrophilic group) capable of binding microorganism membranes, walls, proteins, organelles, saccharides, lipids, cell envelope, or nucleic acids, or any combination thereof. In embodiments, a signaling agent capable of binding to a microorganism's surface comprises a biochemical group capable of binding microorganism membranes, walls, proteins, organelles, saccharides, lipids, cell envelope, or nucleic acids, or any combination thereof.

In embodiments, the surface may include a biomolecule to which the signaling agent binds or associates. Exemplary biomolecules include peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof.

In embodiments, a signaling agent capable of binding to a microorganism's surface comprises a biochemical group capable of binding microorganism membranes, walls, proteins, organelles, saccharides, lipids, cell envelope, or nucleic acids, or any combination thereof.

In embodiments, a signaling agent capable of binding to a microorganism's surface comprises a chemical group (e.g., a nucleophilic or electrophilic functional group) capable of binding microorganism membranes, walls, proteins, organelles, saccharides, lipids, cell envelope, or nucleic acids, or any combination thereof. In embodiments, said chemical group is a nucleophilic functional group. In embodiments, said chemical group is an electrophilic functional group.

In embodiments, a signaling agent is a biochemical signaling agent. In embodiments, a biochemical signaling agent comprises a biomolecule such as an antibody, ligand, protein, aptamer, ss-DNA, ss-RNA, or ss-PNA).

In embodiments, a signaling agent is a chemical signaling agent. In embodiments, a chemical signaling agent is a chemical compound (e.g., a synthetic chemical compound). In embodiments, a chemical signaling agent does not comprise a biomolecule such as an antibody, ligand, protein, aptamer, ss-DNA, ss-RNA, or ss-PNA).

In embodiments, a signaling agent capable of binding to a microorganism's surface comprises
a linker group L; and
an amplifier group (e.g., an amplifier group 104 that is a chemical or biochemical amplifier).

In embodiments, an amplifier group is an amplifier group 104, which is a chemical or biochemical amplifier. In embodiments, an amplifier group 104 is a chemical amplifier. In embodiments, an amplifier group 104 is a biochemical amplifier.

In embodiments, a signaling agent is a chemical compound. In embodiments, a chemical compound comprises a chemical amplifier group such as those described herein).

In embodiments, a linker group L comprises the conserved (Fc) region of an antibody.

In embodiments, a linker group L is capable of forming a covalent bond to an amplifier group (e.g., an amplifier group 104 that is a chemical or biochemical amplifier).

In embodiments, a linker group L forms a covalent bond to a signal amplifier group (e.g., an amplifier group 104 that is a chemical or biochemical amplifier).

In embodiments, a linker group L is capable of forming one or more non-covalent interactions to an amplifier group (e.g., an amplifier group 104 that is a chemical or biochemical amplifier).

In embodiments, a linker group L forms one or more non-covalent interactions to an amplifier group (e.g., an amplifier group 104 that is a chemical or biochemical amplifier).

In embodiments, a linker group L comprises a group (e.g., a chemical or biochemical group) capable of binding a microorganism surface. In embodiments, a linker group L comprises a group (e.g., a chemical or biochemical group) that binds a microorganism surface.

In embodiments, a linker group L comprises a group (e.g., a chemical or biochemical group) that is capable of forming a covalent bond to a microorganism's surface. In embodiments, a linker group L comprises a group (e.g., a chemical or biochemical group) that forms a covalent bond to a microorganism's surface.

In embodiments, a linker group L comprises a group (e.g., a chemical or biochemical group) that is capable of forming one or more non-covalent interactions with a microorganism's surface. In embodiments, a linker group L comprises a group (e.g., a chemical or biochemical group) that forms one or more non-covalent interactions with a microorganism's surface.

In embodiments, a linker group L comprises a chemical moiety 101, wherein said chemical moiety is capable of forming a non-covalent interaction with the surface of a microorganism. In embodiments, a linker group L comprises a chemical moiety 101, wherein said chemical moiety is capable of forming a covalent bond with the surface of a microorganism. In embodiments, a linker group L comprises a chemical moiety 101, wherein said chemical moiety forms a non-covalent interaction with the surface of a microorganism. In embodiments, a linker group L comprises a chemical moiety 101, wherein said chemical moiety forms a covalent bond with the surface of a microorganism.

In embodiments, a linker group L comprises a spacer moiety 102. In embodiments, spacer moiety 102 is covalently attached to chemical moiety 101 and/or to chemical moiety 103. In embodiments, spacer moiety 102 is covalently attached to chemical moiety 101. In embodiments, spacer moiety 102 is covalently attached to chemical moiety 103. In embodiments, spacer moiety 102 is covalently attached to chemical moiety 101 and to chemical moiety 103. In embodiments, spacer moiety 102 forms a non-covalent interaction with chemical moiety 101 and/or with chemical moiety 103. In embodiments, spacer moiety 102 forms a non-covalent interaction with chemical moiety 101. In embodiments, spacer moiety 102 forms a non-covalent interaction with chemical moiety 103. In embodiments, spacer moiety 102 forms a non-covalent interaction with chemical moiety 101 and with chemical moiety 103.

In embodiments, a linker group L comprises a chemical moiety 103, wherein said chemical moiety is capable of forming a covalent bond to an amplifier group (e.g., an amplifier group 104 that is a chemical or biochemical amplifier). In embodiments, a linker group L comprises a chemical moiety 103, wherein said chemical moiety has formed a covalent bond to an amplifier group (e.g., an amplifier group 104 that is a chemical or biochemical amplifier). In embodiments, a linker group L comprises a chemical moiety 103, wherein said chemical moiety is capable of forming a non-covalent interaction with an amplifier group (e.g., an amplifier group 104 that is a chemical or biochemical amplifier). In embodiments, a linker group L comprises a chemical moiety 103, wherein said chemical moiety has formed a non-covalent interaction with an amplifier group (e.g., an amplifier group 104 that is a chemical or biochemical amplifier).

In embodiments, a signaling agent is a chemical compound comprising a linker group L that comprises: a chemical moiety 101, wherein said chemical moiety is capable of forming a covalent bond or a non-covalent interaction with the surface of the microorganisms; a spacer moiety 102, wherein spacer moiety is covalently attached to chemical moiety 101 and to chemical moiety 103; and a chemical moiety 103, wherein said chemical moiety has formed or can form a covalent bond to an amplifier group 104 that is a chemical or biochemical amplifier.

In embodiments, a signaling agent is a chemical compound comprising a linker group L that comprises: a chemical moiety 101, wherein said chemical moiety is capable of forming a covalent bond or a non-covalent interaction with the surface of a microorganism; a spacer moiety 102, wherein spacer moiety is covalently attached to chemical moiety 101 and to chemical moiety 103; and a chemical moiety 103, wherein said chemical moiety has formed or can form a non-covalent interaction with an amplifier group 104 that is a chemical or biochemical amplifier.

In embodiments, a linker group comprises one chemical moiety 101. In embodiments, a linker group comprises more than one chemical moiety 101 (e.g., a linker group comprises 1, 2, 3, 4, 5, or 6 chemical moieties 101).

In embodiments, a linker group comprises one spacer moiety 102. In embodiments, a linker group comprises more than one spacer moiety 102 (e.g., a linker group comprises 1, 2, 3, 4, 5, or 6 spacer moieties 102).

In embodiments, a linker group comprises one chemical moiety 103. In embodiments, a linker group comprises more than one chemical moiety 103 (e.g., a linker group comprises 1, 2, 3, 4, 5, or 6 chemical moieties 103).

In embodiments, a linker group comprises: one chemical moiety 101, one spacer moiety 102, and one chemical moiety 103. In embodiments, a linker group consists of: one chemical moiety 101, one spacer moiety 102, and one chemical moiety 103.

In embodiments, a linker group has the structure of substructure (I):

$$-101\text{-}102\text{-}103\text{-}, \quad (I)$$

wherein
"101" represents a chemical moiety 101;
"102" represents a spacer moiety 102; and
"103" represents a chemical moiety 103.

In embodiments, a chemical moiety 101 is capable of forming a covalent bond with the surface of a microorganism.

In embodiments, a chemical moiety 101 is capable of forming a covalent bond with the surface of a microorganism in the presence of one or more agents that promote coupling (also referred to herein as coupling agents).

In embodiments, agents that promote coupling include glutaraldehyde, formaldehyde, paraformaldehyde, 1-ethyl-3-(3-dimethylaminopropyl)carbodiimide (EDC), N,N'-dicyclohexylcarbodiimide (DCC), N-cyclohexyl-N'-(2-morpholinoethyl)carbodiimide-methyl-p-toluenesulfonate (CMC), diisopropylcarbodiimide (DIC), (1-[bis(dimethylamino)methylene]-1H-1,2,3-triazolo[4,5-b]pyridinium 3-oxide hexafluorophosphate) (HATU), Woodward's Reagent, N,N'-carbonyl diimidazole, N-hydroxysuccinimide (NHS), or N-hydroxysulfosuccinimide (sulfo-NHS), or any combination thereof.

In embodiments, agents that promote coupling include aldehydes, acrylates, amides, imides, anhydrides, chlorotriazines, epoxides, isocyanates, isothiocyanates, organic acids, monomers, polymers, silanes, or silcates, or any combination thereof.

In embodiments, agents that promote coupling include a carbodiimide, a phosphonium salt, or an ammonium salt, or any combination thereof.

In embodiments agents that promote coupling include glutaraldehyde, N-(3-dimethylaminopropyl)-N'-ethylcarbonate (EDC), (1-[bis(dimethylamino)methylene]-1H-1,2,3-triazolo[4,5-b]pyridinium 3-oxide hexafluorophosphate) (HATU), (0-benzotriazol-1-yl-N,N,N,N-tetramethyluronium hexafluorophosphate) (HBTU), N-hydroxysuccinimide (NHS), N,N'-dicyclohexylcarbodiimide (DCC), diisopropylcarbodiimide (DIC), hydroxy-3,4-dihydro-4-oxo-1,2,3-benzotriazine (HOOBt), hydroxybenzotriazole (HOBT), 1-hydroxy-7-azabenzotriazole (HOAt), (N-(3-dimethylaminopropyl)-N'-ethylcarbodiimide (EDAC), 4-(N,N-dimethylamino)pyridine (DMAP), benzotriazol-1-yloxy-tris(dimethylamino)-phosphonium hexafluorophosphate (BOP), benzotriazol-1-yloxy-tripyrrolidino-phosphonium hexafluorophosphate (PyBOP), bromo-tripyrrolidino-phosphonium hexafluorophosphate (PyBrOP), 7-aza-benzotriazol-1-yloxy-tripyrrolidinophosphonium hexafluorophosphate (PyAOP), ethyl cyano(hydroxyimino)acetato-O2)-tri-(1-pyrrolidinyl)-phosphonium hexafluorophosphate (PyOxim), 3-(diethoxy-phosphoryloxy)-1,2,3-benzo[d] triazin-4(3H)-one (DEPBT), 2-(6-chloro-1H-benzotriazol-1-yl)-N,N,N',N'-tetramethylaminium hexafluorophosphate (HCTU), N-[(5-chloro-1H-benzotriazol-1-yl)-dimethylamino-morpholino]-uronium hexafluorophosphate N-oxide (HDMC), 1-[1-(cyano-2-ethoxy-2-oxoethylideneaminooxy)-dimethylamino-morpholino]-uronium hexafluorophosphate (COMU), 2-(1-oxy-pyridin-2-yl)-1,1,3,3-tetramethylisothiouronium tetrafluoroborate (TOTT), tetramethylfluoroformamidinium hexafluorophosphate (TFFH), N-Ethoxycarbonyl-2-ethoxy-1,2-dihydroquinoline (EEDQ), 2-propanephosphonic acid anhydride (PPA), triphosgene, 1,1'-carbonyldiimidazole (CDI), [(6-nitrobenzotriazol-1-yl)oxy]tris(pyrrolidino)phosphonium hexafluorophosphate (PyNOP), [[6-(trifluoromethyl)benzotriazol-1-yl]oxy]tris(pyrroli-dino)phosphonium hexafluorophosphate (PyFOP), [[4-nitro-6-(trifluoromethyl)benzotriazol-1-yl]oxy]tris(pyrrolidino)phosphonium hexafluorophosphate (PyNFOP), [(6-nitrobenzo-triazol-1-yl)oxy]tris(dimethyl-amino)phosphonium hexafluorophosphate (NOP), 1-β-naphthalenesulfonyloxy benzotriazole (NSBt), 1-β-naphthalenesulfonyloxy-6-nitrobenzotriazole (N—NSBt), tetramethylfluoroformamidinium hexafluorophosphate (TFFH), bis(tetramethylene)fluoroformamidinium hexafluorophosphate (BTFFH), 1,3-dimethyl-2-fluoro-4,5-dihydro-1H-imidazolium hexafluorophosphate (DFIH), Cyanuric chloride (CC), or 2,4-dichloro-6-methoxy-1,3,5-triazine (DCMT), and 2-chloro-4,6-dimethoxy-1,3,5-triazine (CDMT), or any combination thereof.

In embodiments, agents that promote coupling include EDC, HATU, HBTU, NHS, DCC, HOBT, or PyBOP, or any combination thereof.

In embodiments, agents that promote coupling include EDC, DCC, CMC, DIC, or HATU, or any combination thereof.

In embodiments, agents that promote coupling include glutaraldehyde, formaldehyde, or paraformaldehyde, or any combination thereof.

In embodiments, a chemical moiety 101 is capable of forming a non-covalent interaction with the surface of a microorganism (e.g., any non-covalent interaction described herein). In embodiments, a non-covalent interaction comprises: ionic, ion-ion, dipole-dipole, ion-dipole, electrostatic, London dispersion, van der Waals, hydrogen bonding, or π-π, or any combination thereof.

In embodiments, a chemical moiety 101 comprises a nucleophilic functional group. In embodiments, a chemical moiety 101 comprises a group formed from a nucleophilic functional group.

In embodiments, a nucleophilic functional group is: amino, amido, hydrazino, hydroxyamino, hydroxy, or thio. In embodiments, a nucleophilic functional group is: amino, hydrazino, hydroxyamino, or thio. In embodiments, a nucleophilic functional group comprises: amino, hydrazino, hydroxyamino, hydroxy, or thio. In embodiments, a nucleophilic functional group is carboxamide, N-hydroxycarboxamide, carboxyl hydrazide, or guanidino.

In embodiments, a nucleophilic functional group is —NH$_2$, —NHNH$_2$, —CONHOH, —CONHNH$_2$, —ONH$_2$, —OH, or —SH. In embodiments, a nucleophilic functional group is —NH$_2$, —NHNH$_2$, —CONHNH$_2$, or —ONH$_2$.

In embodiments, a chemical moiety 101 comprises an electrophilic functional group.

In embodiments, a chemical moiety 101 comprises a group formed from an electrophilic functional group.

In embodiments, an electrophilic functional group comprises an aldehyde, a ketone, a carboxylic acid, a carboxylic ester, a carboxylic acid halide (e.g., acetyl chloride), or a carboxylic acid anhydride (e.g., acetic anhydride).

In embodiments, an electrophilic functional group comprises an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative. In embodiments, an electrophilic functional group is an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative.

In embodiments, an electrophilic functional group comprises an aldehyde, an α-halo ketone, a maleimide, a succinimide, or a hydroxysuccinimide group.

In embodiments, an electrophilic functional group comprises —CHO, —C(O)CH$_2$I, O)CH$_2$I,

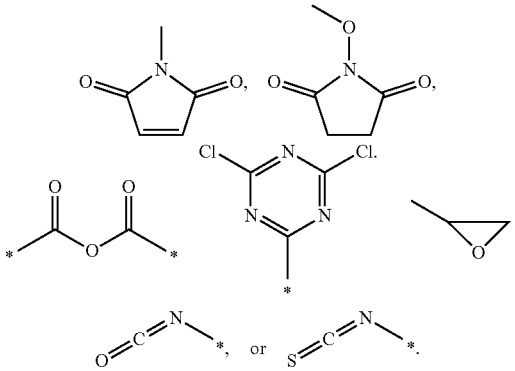

In embodiments, an electrophilic functional group comprises —CHO, —C(O)CH$_2$I,

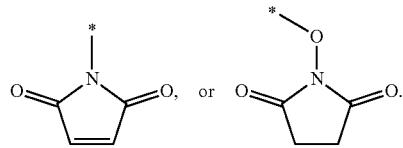

In embodiments, chemical moiety 101 comprises a group that is alkyl, alkenyl, alkynyl, phenyl, heteroaryl, haloalkyl, hydroxy, carbonyl, acyl halide, alkoxycarbonyl)oxy, carboxy, haloketone, alkoxy, alkoxyol (hemiacetal or) hemiketal, dialkoxy (e.g., ketal or acetal), trialkoxy(orthoether), carbamoyl, amino, ammonio, imino, imido, succinamido, maleidido, hydroxysuccinamido, biotin, D-Biotin, azido, azo, cyanate, isocyanato, nitroxy, cyano, isocyano, nitrosooxy, nitro, nitroso, oxime, sulfanyl, sulfinyl, sulfonyl, sulfino, sulfo, thiocyanato, isothiocyanato, thioyl, phosphate, or boronate.

In embodiments, spacer moiety 102 is hydrophobic. In embodiments, spacer moiety 102 is hydrophilic.

In embodiments, spacer moiety 102 is peptidic (e.g., derived from peptide linkages).

In embodiments, spacer moiety 102 comprises inorganic linkages. In embodiments, spacer moiety 102 comprises organic linkages. In embodiments, spacer moiety 102 comprises only organic linkages.

In embodiments, spacer moiety 102 is oligomeric. In embodiments, spacer moiety 102 is polymeric. In embodiments, spacer moiety 102 comprises segments (e.g., 1 to about 300, 1 to about 200, 1 to about 100, 1 to about 50, 1 to about 25, or 1 to about 10, or 1, 2, 3, 4, 5, 6, 7, 8, 9, or 10 segments) of methylene (—CH$_2$—), ethylene glycol (—CH$_2$CH$_2$O—), iminoethylene (—CH$_2$CH$_2$NH—), vinyl alcohol (—CH$_2$CHOH—)$_x$, lactic acid (—CH(CH$_3$)—C(O)—O—), acrylic acid (—CH$_2$CH$_2$(CO$_2$H)—), methacrylic acid (—CH$_2$C(CH$_3$)(CO$_2$H)—), or methyl methacrylate (—CH$_2$C(CH$_3$)(CO$_2$CH$_3$)—).

In embodiments, spacer moiety 102 comprises a segment that is

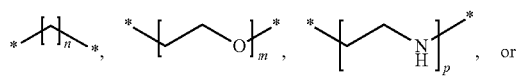

-continued

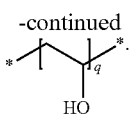

In embodiments, n, m, p, and q independently is an integer of 1 to about 300 (e.g., 1 to about 200, 1 to about 100, 1 to about 50, 1 to about 25, or 1 to about 10). In embodiments, each of n, m, p, and q is independently 1, 2, 3, 4, 5, 6, 7, 8, 9, or 10.

In embodiments, spacer moiety 102 comprises

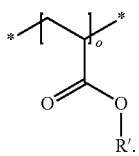

In embodiments, R' is independently hydrogen or a group that is $C_1$-$C_{12}$ alkyl, $C_2$-$C_{12}$ alkenyl, or $C_2$-$C_{12}$ alkynyl. In embodiments, o is an integer of 1 to about 300 (e.g., 1 to about 200, 1 to about 100, 1 to about 50, 1 to about 25, or 1 to about 10). In embodiments, o is independently 1, 2, 3, 4, 5, 6, 7, 8, 9, or 10.

In embodiments, spacer moiety 102 comprises

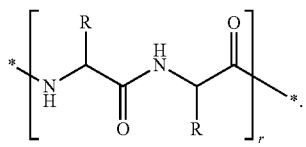

In embodiments, R is independently hydrogen or a group that is $C_1$-$C_{12}$ alkyl, $C_2$-$C_{12}$ alkenyl, or $C_2$-$C_{12}$ alkynyl. In embodiments, r is an integer of 1 to about 300 (e.g., 1 to about 200, 1 to about 100, 1 to about 50, 1 to about 25, or 1 to about 10). In embodiments, r is independently 1, 2, 3, 4, 5, 6, 7, 8, 9, or 10.

In embodiments, spacer moiety 102 comprises

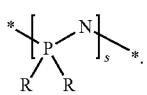

In embodiments, R is independently hydrogen or a group that is $C_1$-$C_{12}$ alkyl, $C_2$-$C_{12}$ alkenyl, or $C_2$-$C_{12}$ alkynyl. In embodiments, s is an integer of 1 to about 300 (e.g., 1 to about 200, 1 to about 100, 1 to about 50, 1 to about 25, or 1 to about 10). In embodiments, s is independently 1, 2, 3, 4, 5, 6, 7, 8, 9, or 10.

In embodiments, spacer moiety 102 comprises

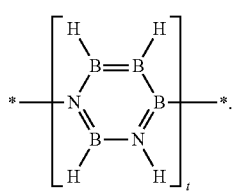

In embodiments, t is an integer of 1 to about 300 (e.g., 1 to about 200, 1 to about 100, 1 to about 50, 1 to about 25, or 1 to about 10). In embodiments, t is independently 1, 2, 3, 4, 5, 6, 7, 8, 9, or 10.

In embodiments, spacer moiety 102 comprises:

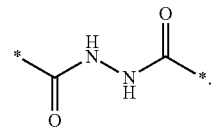

In embodiments, spacer moiety 102 is a polymer comprising repeating groups, comprising alkyl, alkoxy, ester, acrylic, amino, hydroxyl, or acyl hydrazine functional groups, or any combination thereof.

In embodiments, the spacer moiety 102 is:

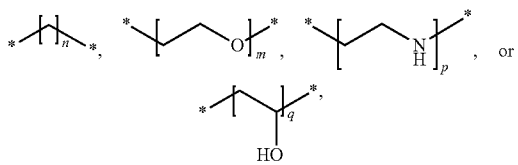

wherein n, m, p, and q are as defined herein.

In embodiments, each of n, m, o, p, q, r, s, or t independently is an integer of 1 to 100, of 10 to 90, of 10 to 80, of 10 to 70, of 10 to 60, of 10 to 50, of 10 to 40, of 10 to 30, of 10 to 20, or of 1 to 10.

In embodiments, a chemical moiety 103 comprises a group that is a nucleophilic functional group.

In embodiments, a chemical moiety 103 comprises a group formed from a nucleophilic functional group.

In embodiments, a nucleophilic functional group is: amino, amido, hydrazino, hydroxyamino, hydroxy, or thio.

In embodiments, a nucleophilic functional group is: amino, hydrazino, hydroxyamino, or thio.

In embodiments, a nucleophilic functional group comprises: amino, hydrazino, hydroxyamino, hydroxy, or thio.

In embodiments, a nucleophilic functional group is carboxamide, N-hydroxycarboxamide, carboxyl hydrazide, or guanidino.

In embodiments, a nucleophilic functional group is —$NH_2$, —$NHNH_2$, —CONHOH, —$CONHNH_2$, —$ONH_2$, —OH, or —SH. In embodiments, a nucleophilic functional group is —$NH_2$, —$NHNH_2$, —$CONHNH_2$, or —$ONH_2$.

In embodiments, a chemical moiety 103 comprises a group that is a electrophilic functional group.

In embodiments, a chemical moiety 103 comprises a group formed from a electrophilic functional group.

In embodiments, an electrophilic functional group comprises an aldehyde, a ketone, a carboxylic acid, a carboxylic ester, a carboxylic acid halide (e.g., acetyl chloride), or a carboxylic acid anhydride (e.g., acetic anhydride).

In embodiments, an electrophilic functional group comprises an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative. In embodiments, an electrophilic functional group is an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative.

In embodiments, an electrophilic functional group comprises an aldehyde, an α-halo ketone, a maleimide, a succinimide, or a hydroxysuccinimide group.

In embodiments, an electrophilic functional group comprises —CHO, —C(O)CH$_2$I,

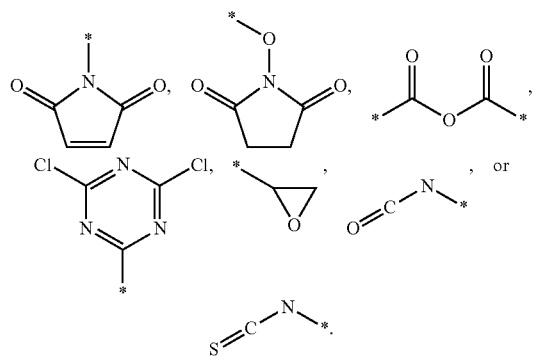

In embodiments, an electrophilic functional group comprises —CHO, —C(O)CH$_2$I,

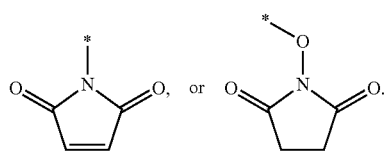 [SMILES: *N1C(=O)C=CC1=O ; *ON1C(=O)CCC1=O]

In embodiments, a chemical moiety 103 comprises a chemical structure that is carbonyl, alkenyl, alkynyl, hydroxyl, amino, thiol, maleimide, succinimide, hydroxy succinimide, biotinyl, anhydride, chlorotriazine, epoxide, isocyanate, or isothiocyanate. In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate is capable of forming a covalent bond to an amplifier group (e.g., an amplifier group 104). In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate is capable of forming non-covalent interaction with an amplifier group (e.g., an amplifier group 104).

In embodiments, a chemical moiety 103 is formed from a chemical structure comprising a group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate. In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate has formed a covalent bond to an amplifier group (e.g., an amplifier group 104). In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate has formed a non-covalent interaction with an amplifier group (e.g., an amplifier group 104).

In embodiments, a chemical moiety 103 comprises a group that is carbonyl, alkenyl, alkynyl, hydroxyl, amino, thiol, maleimide, succinimide, hydroxysuccinimide, or biotinyl.

In embodiments, a chemical moiety 103 comprises a carbonyl, alkenyl, alkynyl, hydroxyl, amino, thiol, maleimide, succinimide, hydroxysuccinimide, or biotinyl functional group.

In embodiments, a chemical moiety 103 comprises:

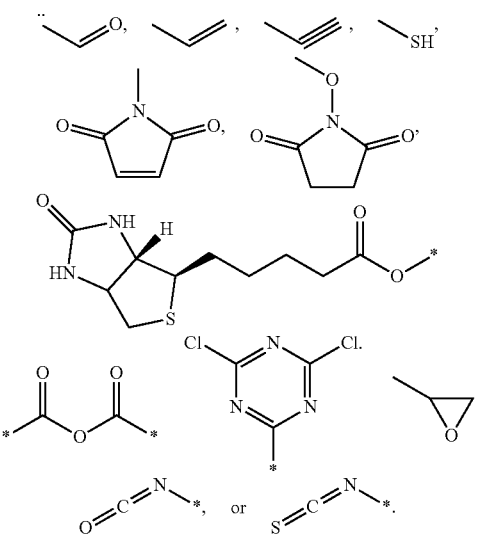

In embodiments, a chemical moiety 103 comprises a group formed from a chemical structure comprising a group that is carbonyl, alkenyl, alkynyl, hydroxyl, amino, thiol, maleimide, succinimide, hydroxysuccinimide, or biotinyl functional group.

In embodiments, a linker group L has the structure of substructure (II):

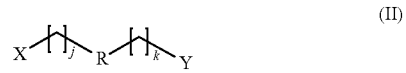

(II)

wherein:
X represents a chemical moiety 101 (e.g., any chemical moiety 101 as described herein;
R represents a spacer moiety 102 (e.g., any spacer moiety 102 as described herein);
Y represents a chemical moiety 103 (e.g., any chemical moiety 103 as described herein); and
each of j and k independently is an integer of 0 to 100.
In embodiments, X is

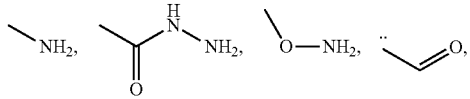

59
-continued

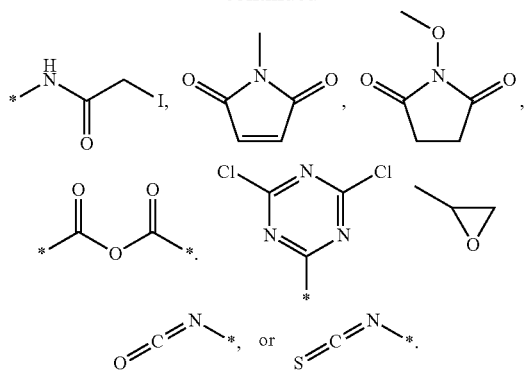

In embodiments, R is

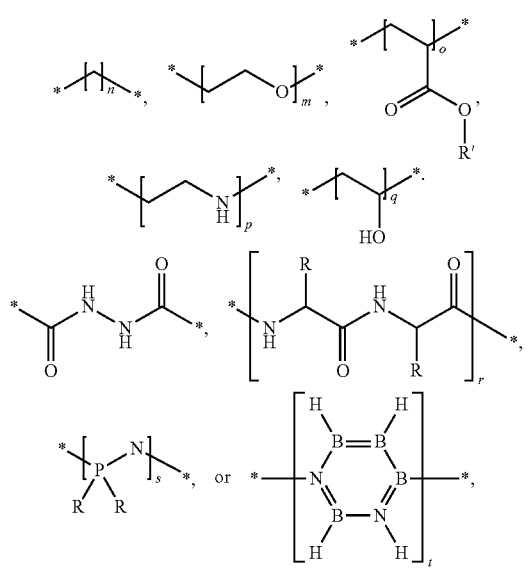

wherein each of n, m, o, p, q, r, s, or t is as described herein (e.g., an integer of 1 to about 300).

In embodiments, Y is

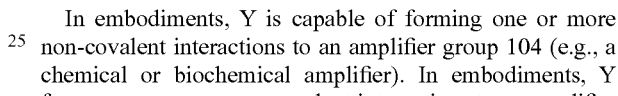

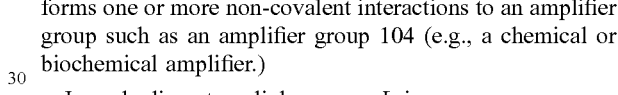

60
-continued

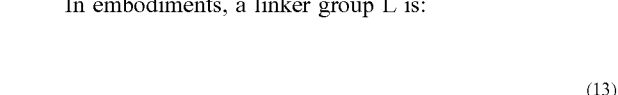

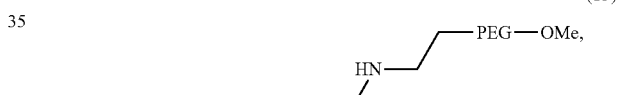

In embodiments, X is capable of forming a covalent bond to a microorganism's surface. In embodiments, X forms a covalent bond to a microorganism's surface.

In embodiments, X is capable of forming one or more non-covalent interactions with a microorganism's surface. In embodiments, X forms one or more non-covalent interactions with a microorganism's surface.

In embodiments, Y is capable of forming a covalent bond to an amplifier group 104 (e.g., a chemical or biochemical amplifier). In embodiments, Y forms a covalent bond to an amplifier group such as an amplifier group 104 (e.g., a chemical or biochemical amplifier.)

In embodiments, Y is capable of forming one or more non-covalent interactions to an amplifier group 104 (e.g., a chemical or biochemical amplifier). In embodiments, Y forms one or more non-covalent interactions to an amplifier group such as an amplifier group 104 (e.g., a chemical or biochemical amplifier.)

In embodiments, a linker group L is:

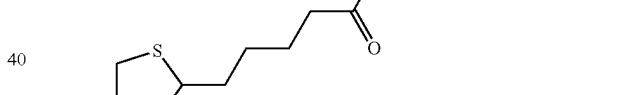
(13)

(14)

(15)
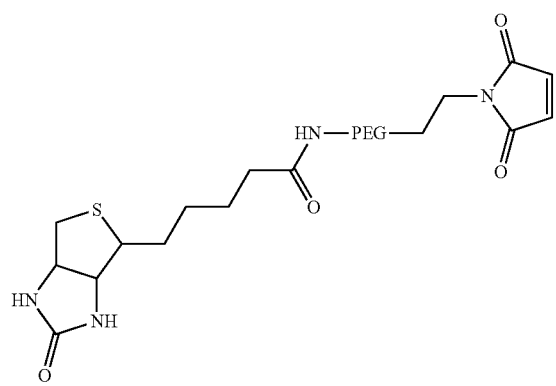

(20)
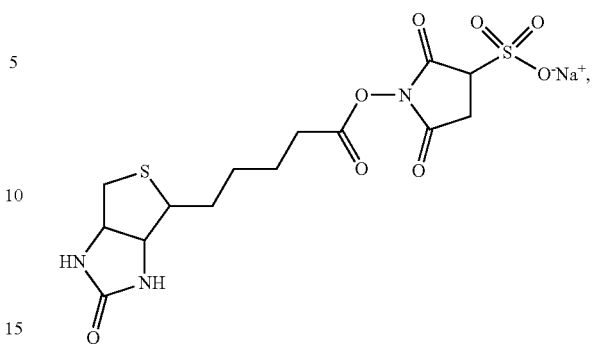

(16)
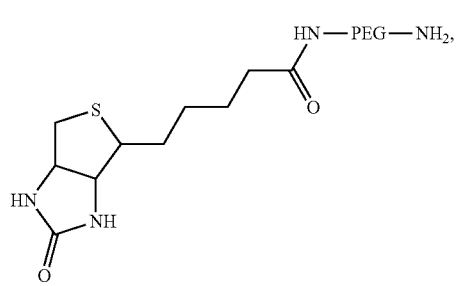

(17)
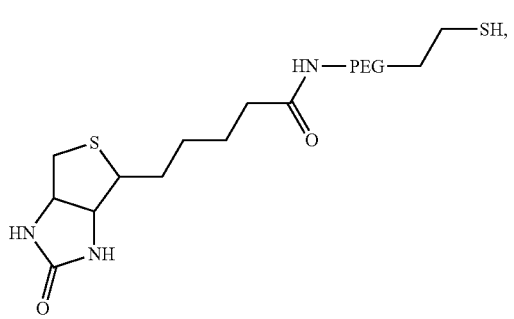

(18)
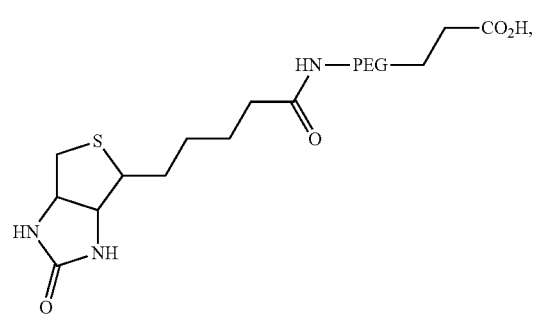

(19)
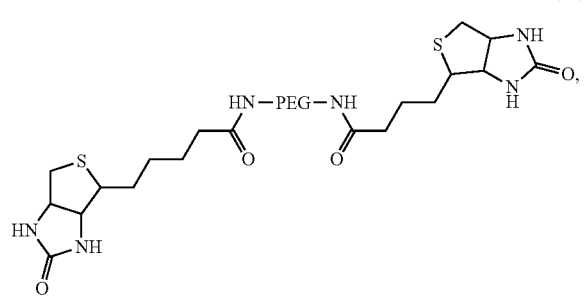

WGA-Biotin, PolymixinB-Biotin, monoclonal antibody, polyclonal antibody, biotinylated monoclonal antibody, biotinylated polyclonal antibody, europium chelate-antibody, horseradish peroxidase-conjugated antibody, and antibody variants (e.g., Fab: fragment, antigen-binding (one arm); F(ab')2: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager).

Exemplary amplifier groups include those described in, e.g., International Publication No. WO 2016/015027 and in International Application No. PCT/US16/42589, each of which is incorporated by reference in its entirety.

In embodiments, an amplifier group (e.g., an amplifier group 104) comprises a catalyst, a fluorophore, or a colormetric dye. In embodiments, an amplifier group (e.g., an amplifier group 104) is a catalyst, a fluorophore, or a colormetric dye.

In embodiments, an amplifier group (e.g., an amplifier group 104) comprises an enzyme, a catalyst, or a nanoparticle. In embodiments, an amplifier group (e.g., an amplifier group 104) is an enzyme, a catalyst, or a nanoparticle.

In embodiments, a chemical amplifier group comprises a catalyst, a fluorophore, a nanoparticle, or a colormetric dye. In embodiments, a chemical amplifier group is a catalyst, a fluorophore, a nanoparticle, or a colormetric dye.

In embodiments, an amplifier group (e.g., an amplifier group 104) comprises a catalyst. In embodiments, an amplifier group (e.g., an amplifier group 104) is a catalyst.

In embodiments, an amplifier group (e.g., an amplifier group 104) comprises a fluorophore. In embodiments, an amplifier group (e.g., an amplifier group 104) is a fluorophore. Exemplary fluorophores include those described in Table 1 of International Application No. PCT/US16/42589, which is incorporated by reference in its entirety.

In embodiments, an amplifier group (e.g., an amplifier group 104) comprises a colormetric dye. In embodiments, an amplifier group (e.g., an amplifier group 104) is a colormetric dye.

In embodiments, an amplifier group (e.g., an amplifier group 104) comprises an enzyme. In embodiments, an amplifier group (e.g., an amplifier group 104) is an enzyme.

In embodiments, an amplifier group (e.g., an amplifier group 104) comprises a nanoparticle. In embodiments, an amplifier group (e.g., an amplifier group 104) is a nanoparticle.

In embodiments, an amplifier group (e.g., an amplifier group 104) comprises a lanthanide.

In embodiments, an amplifier group (e.g., an amplifier group 104) comprises a lanthanide that is europium, strontium, terbium, samarium, or dysprosium. In embodiments, an amplifier group (e.g., an amplifier group 104) comprises a lanthanide selected from the group consisting of: europium, strontium, terbium, samarium, and dysprosium.

In embodiments, an amplifier group (e.g., an amplifier group 104) comprises an organic fluorophore.

In embodiments, an amplifier group (e.g., an amplifier group 104) comprises a fluorophore that is a coordination complex.

In embodiments, an amplifier group (e.g., an amplifier group 104) comprises a europium coordination complex. In embodiments, a coordination complex is a europium coordination complex. In embodiments, an amplifier group (e.g., an amplifier group 104) comprises a ruthenium coordination complex. In embodiments, a coordination complex is a ruthenium coordination complex. In embodiments, an amplifier group (e.g., an amplifier group 104) comprises a rhenium coordination complex. In embodiments, a coordination complex is a rhenium coordination complex. In embodiments, an amplifier group (e.g., an amplifier group 104) comprises a palladium coordination complex. In embodiments, a coordination complex is a palladium coordination complex. In embodiments, an amplifier group (e.g., an amplifier group 104) comprises a platinum coordination complex. In embodiments, a coordination complex is a platinum coordination complex.

In embodiments, an amplifier group (e.g., an amplifier group 104) comprises a chemiluminophore, a quantum dot, an enzyme, an iron coordination catalyst, a europium coordination complex, a ruthenium coordination complex, a rhenium coordination complex, a palladium coordination complex, a platinum coordination complex, a samarium coordination complex, a terbium coordination complex, or a dysprosium coordination complex.

In embodiments, an amplifier group (e.g., an amplifier group 104) comprises a chemiluminophore. In embodiments, an amplifier group (e.g., an amplifier group 104) comprises a quantum dot. In embodiments, an amplifier group (e.g., an amplifier group 104) comprises an enzyme. In embodiments, an amplifier group (e.g., an amplifier group 104) comprises an iron coordination catalyst. In embodiments, an amplifier group (e.g., an amplifier group 104) comprises a europium coordination complex. In embodiments, an amplifier group (e.g., an amplifier group 104) comprises a ruthenium coordination complex. In embodiments, an amplifier group (e.g., an amplifier group 104) comprises a rhenium coordination complex. In embodiments, an amplifier group (e.g., an amplifier group 104) comprises a palladium coordination complex. In embodiments, an amplifier group (e.g., an amplifier group 104) comprises a platinum coordination complex. In embodiments, an amplifier group (e.g., an amplifier group 104) comprises a samarium coordination complex. In embodiments, an amplifier group (e.g., an amplifier group 104) comprises a terbium coordination complex. In embodiments, an amplifier group (e.g., an amplifier group 104) comprises a dysprosium coordination complex.

In embodiments, an amplifier group 104 comprises a moiety that is:

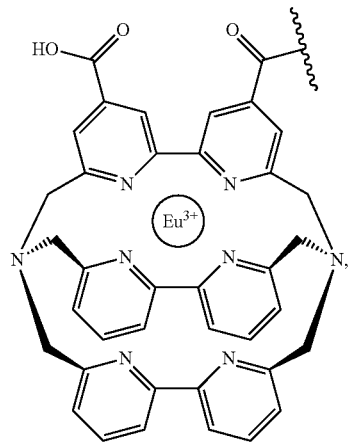

(III)

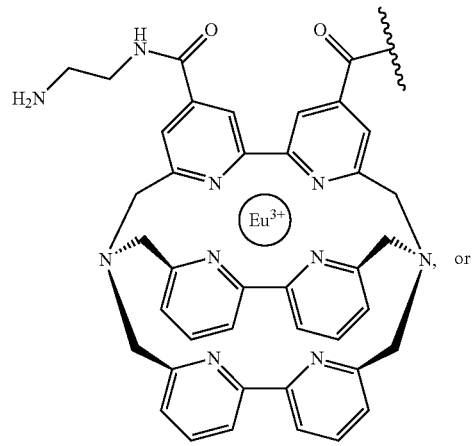

(IV)

In embodiments, an amplifier group 104 comprises a moiety that is:

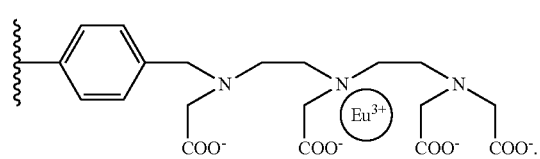

(V)

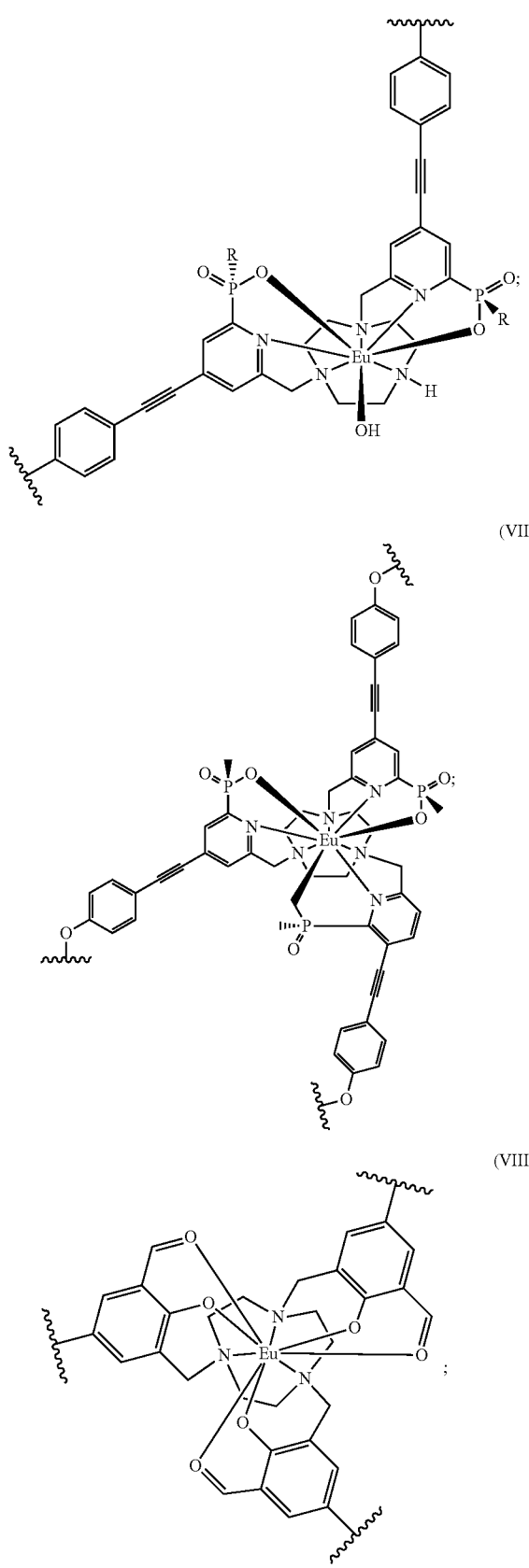

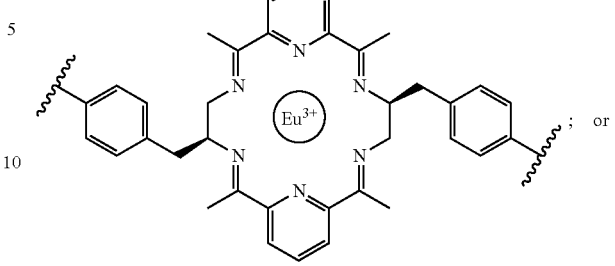

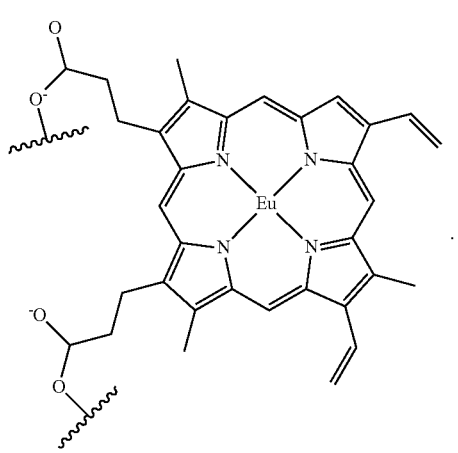

In embodiments, an amplifier group 104 is a catalyst or enzyme. In embodiments, an amplifier group is horseradish peroxidase, alkaline phosphatase, acetyl cholinesterase, glucose oxidase, beta-D-galactosidase, or beta-lactamase.

In embodiments, amplifier group 104 is horseradish peroxidase.

In embodiments, amplifier group 104 is a fluorophore or colormetric dye.

Suitable fluorophores and colormetric dyes are well known to those skilled in the art and are described in *The Molecular Probes® Handbook: A Guide to Fluorescent Probes and Labeling Technologies*, 11$^{th}$ Ed. (2010) and Gomes, Fernandes, and Lima *J. Biochem. Biophys. Methods* 65 (2005) pp 45-80, which are herein incorporated by reference in their entirety. Exemplary fluorophores also include those described in, e.g., International Publication No. WO 2016/015027 and in International Application No. PCT/US16/42589, each of which is incorporated by reference in its entirety.

Examples of suitable fluorophore or colormetric dyes include, but are not limited to, ethidium bromide, propidium iodide, SYTOX green, phenanthridines, acridines, indoles, imidazoles, cyanine, TOTO, TO-PRO, SYTO, 5-carboxy-2,7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-ROX (carboxy-X-rhodamine), 6-Carboxyrhodamine 6G, 7-Amino-4-methylcoumarin, 7-Aminoactinomycin D (7-AAD), 7-Hydroxy-4-methylcoumarin, 9-Amino-6-chloro-2-methoxyacridine, ACMA (9-Amino-6-chloro-2-methoxyacridine), Acridines, Alexa Fluors, Alizarin, Allophycocyanin (APC), AMCA (Aminomethylcoumarin), Bodipy, Carboxy-X-rhodamine, Catecholamine, Fluorescein (FITC), Hydroxycoumarin, Lissamine Rhodamine, Monobromobimane, Oregon Green, Phycoerythrin, SYTO, Thiadicarbocyanine (DiSC3), Thioflavin, X-Rhodamine, C or TetramethylRodaminelsoThio-Cyanate.

In embodiments, amplifier group 104 is an organometallic compound, transition metal complex, or coordination complex. Exemplary examples are described in but not limited to EP 0 180 492, EP 0 321 353, EP 0 539 435, EP 0 539 477, EP 0 569 496, EP139675, EP64484, U.S. Pat. Nos. 4,283,382, 4,565,790, 4,719,182, 4,735,907, 4,808,541, 4,927,923, 5,162,508, 5,220,012, 5,324,825, 5,346,996, 5,373,093, 5,432,101, 5,457,185, 5,512,493, 5,527,684, 5,534,622, 5,627,074, 5,696,240, 6,100,394, 6,340,744, 6,524,727, 6,717,354, 7,067,320, 7,364,597, 7,393,599, 7,456,023, 7,465,747, 7,625,930, 7,854,919, 7,910,088, 7,955,859, 7,968,904, 8,007,926, 8,012,609, 8,017,254, 8,018,145, 8,048,659, 8,067,100, 8,129,897, 8,174,001, 8,183,586, 8,193,174, 8,221,719, 8,288,763, 8,362,691, 8,383,249, 8,492,783, 8,632,753, 8,663,603, 8,722,881, 8,754,206, 8,890,402, 8,969,862, 9,012,034, 9,056,138, 9,118,028, 9,133,205, 9,187,690, 9,193,746, 9,312,496, 9,337,432, 9,343,685, 9,391,288, and 9,537,107, which are incorporated by reference in their entirety. Exemplary organometallic compounds, transition metal complexes, or coordination complexes also include those described in, e.g., International Publication No. WO 2016/015027 and in International Application No. PCT/US16/42589, each of which is incorporated by reference in its entirety.

In embodiments, amplifier group 104 is a lanthanide coordination complex.

In embodiments, a lanthanide coordination complex is a complex between a lanthanide (e.g., Eu or Tb) and a tetradentate ligand.

In embodiments, a lanthanide coordination complex is a complex between a lanthanide (e.g., Eu or Tb) and a cryptate ligand.

In embodiments, amplifier group 104 is a coordination complex of Lanthanum (La), Cerium (Ce), Praseodymium (Pr), Neodymium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Ruthenium (Ru), Rhodium (Rh), Palladium (Pd), Osmium (Os), Iridium (Ir), or Platinum (Pt).

In embodiments, amplifier group 104 is a coordination complex of a rare earth metal collectively refers to 17 elements consisting of a group of 15 elements from lanthanum having an atomic number of 57 to lutetium having an atomic number of 71 (lanthanides), and two additional elements consisting of scandium having an atomic number of 21 and yttrium having an atomic number of 39. Specific examples of rare earth metals include europium, terbium, lanthanum, cerium, praseodymium, neodymium, promethium, samarium, gadolinium, dysprosium, holmium, erbium, thulium, ytterbium, lutetium, scandium and yttrium, with europium and terbium being preferable, and europium being more preferable.

In embodiments, amplifier group 104 is a coordination complex of a lanthanide (e.g., Europium or Terbium) with diethylenetriaminetetraacetic acid or a cryptate ligand.

In embodiments, amplifier group 104 is a coordination complex of a lanthanide (e.g., Europium or Terbium) with diethylenetriaminetetraacetic acid.

In embodiments, amplifier group 104 is a coordination complex of a lanthanide (e.g., Europium or Terbium) with a cryptate ligand.

In embodiments, a signaling agent (e.g., a chemical signaling agent) comprises or is formed from:

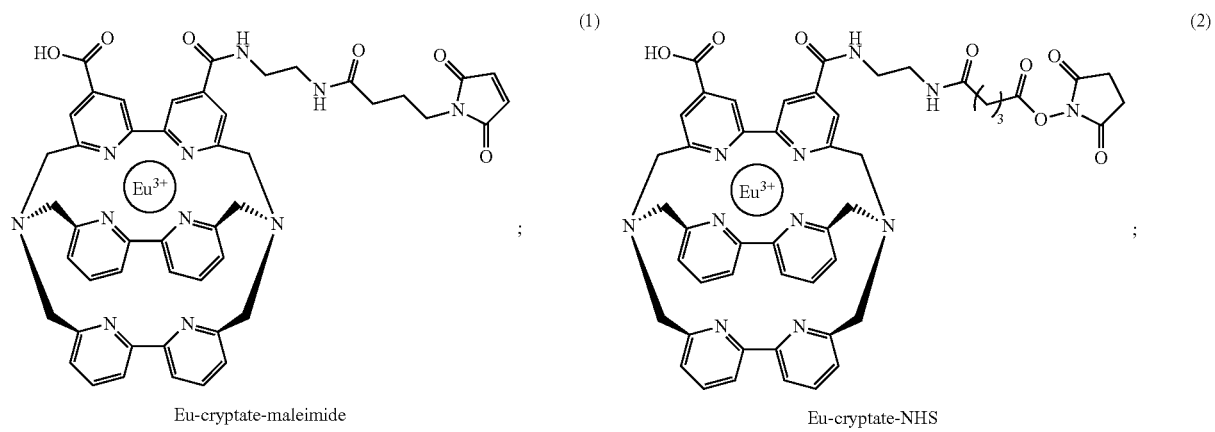

Eu-cryptate-maleimide (1); Eu-cryptate-NHS (2);

-continued
(3)
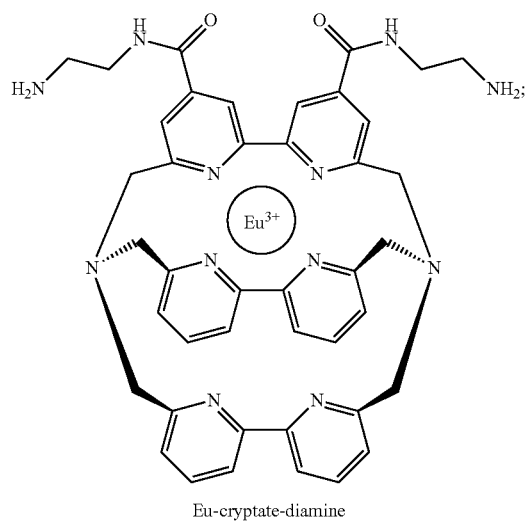
Eu-cryptate-diamine
(4)
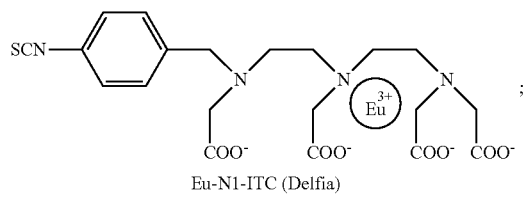
Eu-N1-ITC (Delfia)
(5)
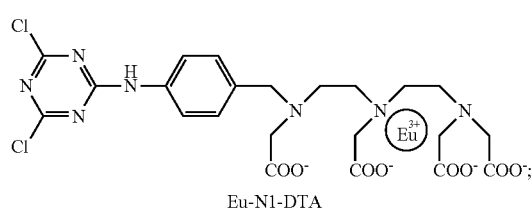
Eu-N1-DTA
(6)
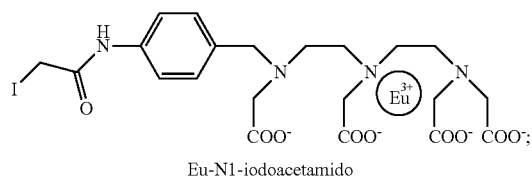
Eu-N1-amino
(7)
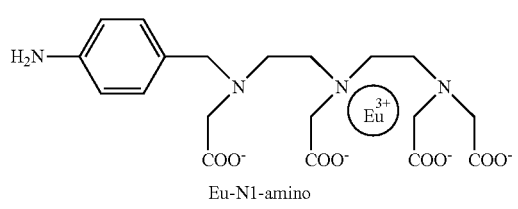
Eu-N1-iodoacetamido
(8)
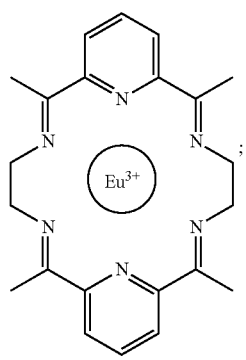
(9)
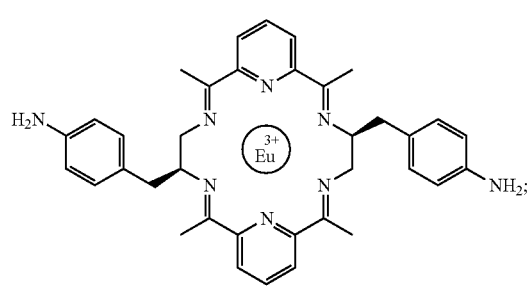
(10)
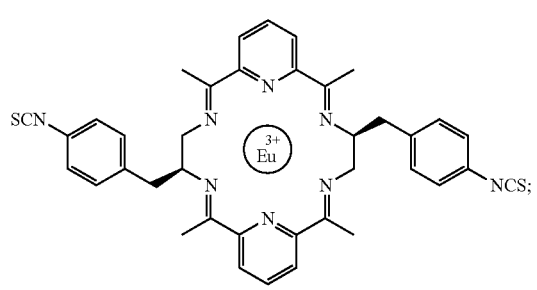

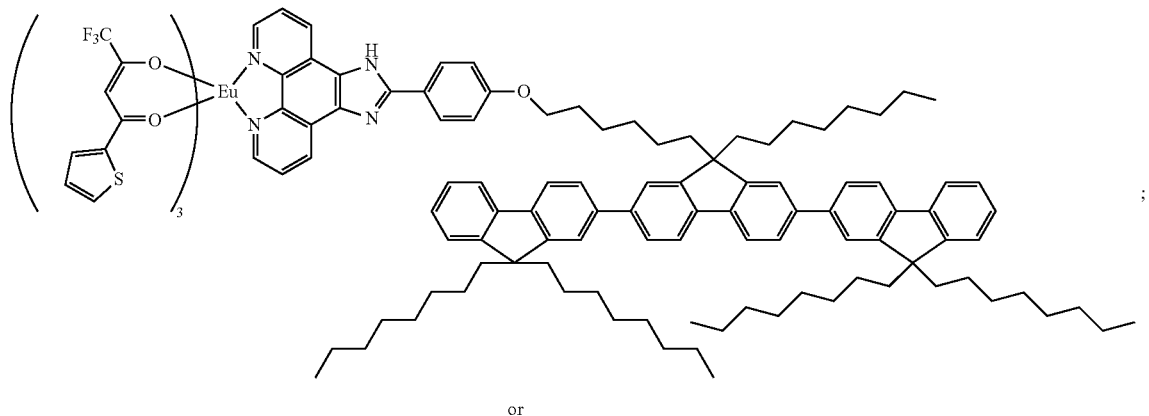

(11)

or

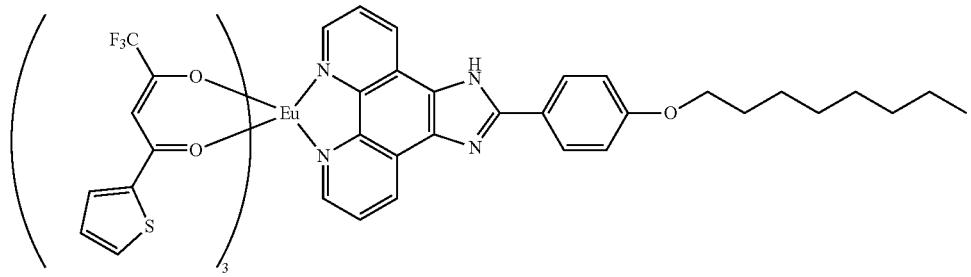

(12)

In embodiments, a signaling agent may comprise one or more paramagnetic metal chelates in order to form a contrast agent. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III). Additionally, a signaling agent of the present disclosure may also comprise one or more superparamagnetic particles.

In embodiments, a signaling agent may comprise one or more metals that are included in a metal complex along with or as a part of a fluorescent compound: The metal complex includes metal complexes having Al, Zn, Be, or the like; a rare-earth metal such as Tb, Eu, or Dy; or a transition metal such as Pt or Ir as a central metal, and having an oxadiazole, thiadiazole, phenylpyridine, phenylbenzimidazole, or quinoline structure as a ligand, such as aluminum quinolinol complexes, benzoquinolinol beryllium complexes, benzoxazole zinc complexes, benzothiazole zinc complexes, azomethyl zinc complexes, porphyrin zinc complexes, and europium complexes.

In embodiments, a signaling agent may comprise a luminophore (donor) which features high luminescence quantum efficiency and long luminescence decay time (>100 ns). Preferred luminophores are cationic, metalorganic complexes of palladium, rhodium, platinum, ruthenium, osmium, rare earths (in particular, europium and lanthanum). The organic portion of these metalorganic complexes may consist, for example, of ligands from the group of porphyrins, bipyridyls, phenanthrolines or other heterocyclical compounds.

In embodiments, a signaling agent capable of binding a microorganism surface comprises an antibody (e.g., monoclonal or polyclonal), modified antibodies (e.g., biotinylated monoclonal antibody, biotinylated polyclonal antibody, europium chelate-antibody, horseradish peroxidase-conjugated antibody), antibody variants (e.g., Fab: fragment, antigen-binding (one arm); F(ab')$_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), WGA-Biotin, PolymixinB-Biotin, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In embodiments, a signaling agent capable of binding a microorganism surface comprises an amplifier group 104 that comprises a lanthanide coordination complex, and/or an enzyme and streptavidin and/or an antibody and/or aptamer.

In embodiments, a signaling agent capable of binding to a microorganism surface comprises:

an antibody; and a europium coordination complex.

In embodiments, a signaling agent capable of binding to a microorganism surface comprises a linker group L that comprises NH2-PEG-Biotin (2K), NH2-PEG-Biotin (4K), sulfo-NHS-Biotin, WGA-Biotin, or polymixinB-Biotin.

In embodiments, a signaling agent capable of binding to a microorganism surface comprises a Europium complex comprising:

(III)

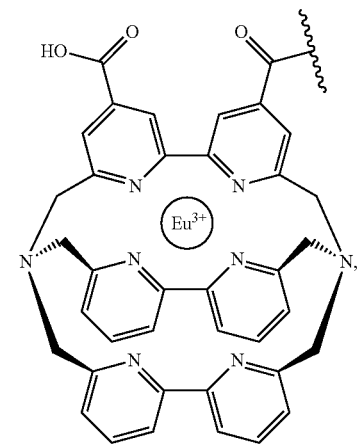

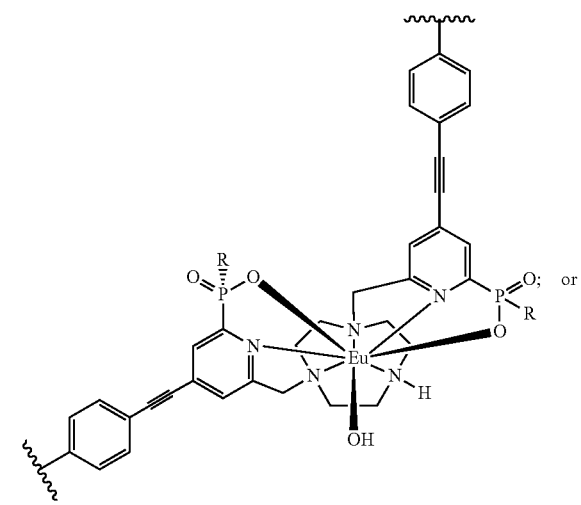

(IV)

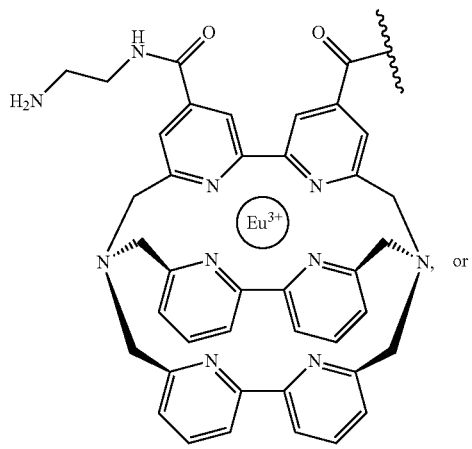, or (V)

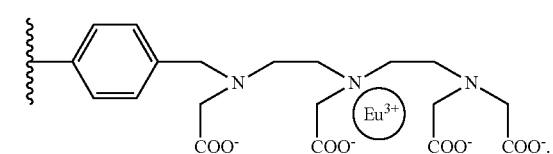

In embodiments, a signaling agent capable of binding to a microorganism surface comprises a Europium complex comprising:

As disclosed throughout the Specification and Drawings, the present disclosure provides, at least:
- >89.9% MIC agreement (±1 dilution) between presently-disclosed methods and CLSI standard with no major/very major errors for seventy-five strains of twelve bacterial species (including β-lactams with gram-negative rods);
- Equivalent MICs between the presently-disclosed method for direct-from-positive-blood culture and CLSI standard blood culture sample processing,
- Detection of gram-positive and negative species down to 2×10³ CFU/ml;
- Non-specific binding of a microorganism by a signaling agent;
- Use of Europium formulations;
- Semi-automated device use with data output.

Additional teaching relevant to the present disclosure are described in one or more of the following: EP139675; EP64484; US 2013/0217063; US 2014/0278136; US 2014/0323340; US 2014/0363817; US 2015/0064703; US 2015/0337351; US 2016/0010138; U.S. Pat. Nos. 3,798,320; 4,565,790; 4,647,536; 4,808,541; 4,927,923; 5,457,185;

5,489,401; 5,512,493; 5,527,684; 5,627,074; 5,665,554; 5,695,946; 6,284,470; 6,385,272; 6,844,028; 7,341,841; 7,629,029; 7,868,144; 8,178,602; 8,895,255; PCT/US2016/042589; and WO/2016015027 each of which is incorporated herein by reference in their entireties.

Any of the above aspects and embodiments can be combined with any other aspect or embodiment as disclosed in the Drawings, in the Summary of this disclosure, and/or in the Detailed Description, including the below Examples.

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

AST Assays Utilizing Sufficient Growth Checkpoints

The rapid AST methods described herein can provide accurate results that are consistent with results obtained using the Clinical Laboratory Standards Institute (CLSI) reference methods when tested with multiple antimicrobials and on a plurality of microorganisms; however, these methods can require significantly less time to provide results than the CLSI methods. The methods described herein, in a greatly reduced amount of time and expense, relative to standard methods, can provide a patient with an appropriate treatment regimen, i.e., a specific antimicrobial and at a particular dosage. Thus, the methods described herein can improve patient outcomes, lower hospital costs, and help reduce further evolution of antimicrobial resistant microorganisms; thus, the methods described herein represent a significant breakthrough in the AST field.

The methods provided by the present application are, in one aspect, intended to be performed in conjunction with rapid AST methods, such as those described in PCT/US17/14343 and devices such as those described in PCT/US17/28906, which are incorporated by reference herein in their entirety.

For example, a rapid AST method can provide for introducing a suspension of microorganisms to a cartridge comprising a plurality of chambers comprising antimicrobials at pre-determined antimicrobial concentrations. A cartridge can be a multi-well plate. A cartridge comprises one or more reservoirs of wells. In some embodiments, the cartridge is a microplate. The cartridge can comprise at least 2, 4, 6, 8, 12, 24, 48, 96, 192, 384, or 1536 chambers. Further, cartridge chambers can be wells or reservoirs on a microplate. The suspension of microorganisms can comprise medium that comprises at least one nutrient.

Further, a rapid AST method can include incubating the cartridge for a time period under conditions promoting microorganism growth. The incubation time period can occur for about 1 hour, 2 hours, 3 hours, 4 hours, 5 hours, or 6 hours. The initial incubation, in some embodiments, occurs for a time period from about 1 to 2 hours, from about 1 to 3 hours, from about 1 to 4 hours, from about 1 to 5 hours, from about 1 to 6 hours, from about 2 to 3 hours, from about 2 to 4 hours, from about 2 to 5 hours, from about 2 to 6 hours, from about 3 to 4 hours, from about 3 to 5 hours, from about 3 to 6 hours, from about 4 to 5 hours, from about 4 to 6 hours, or from about 5 to 6 hours. In some embodiments, the initial incubation period is about 3 hours.

Finally, a rapid AST method can provide for performing a growth assay in order to determine a microorganism's susceptibility to an antimicrobial. Growth assays can be viability assays. Non-limiting examples of growth assays can include a metabolic probe assay, a surface-binding probe assay, a chemical probe assay, a biochemical probe assay, an ATP assay, a nucleic acid probe assay, a double-stranded nucleic acid probe assay, an optical density assay, a visual assay, or a pH molecular probe assay.

As is known to those skilled in the art, AST platforms can yield minimum inhibitory concentration (MIC) results and/or qualitative susceptibility results (QSRs) for each antimicrobial tested. According to CLSI Microbiology standards, an MIC of a given antibiotic for a given species and strain of a microorganism can be defined as the lowest concentration of the antibiotic in two-fold dilution series that inhibits growth of the microorganism and can provide physicians with dosing information. QSRs can also provide physicians with similar dosing information but cannot provide a numerical MIC.

AST assays can be predominantly configured to test multiple antimicrobials in parallel for each obtained biological sample. In order to produce MIC or QSR results, dilution series can be required for each antimicrobial. Thus, for liquid-based ASTs, termed "broth microdilution" by the CLSI, assays are commonly performed in cartridges and/or microplates, which enable parallel testing of different antimicrobials at different concentrations. These MICs, along with the microorganism species and antimicrobial, are used to determine the Clinical & Laboratory Standards Institute (CLSI) breakpoint interpretation to provide the clinical AST result for each combination of microorganism species and antimicrobial. Such results take the form of Susceptible (S), Intermediate (I), Resistant (R), Not Susceptible (NS), and No Interpretation (NI) per CLSI publication M-100S.

As disclosed, (e.g., in the Examples), the methods described herein have been shown to deliver equivalent results to the gold-standard for a broad range of microorganism species, including all six (*Enterococcus faecium, Staphylococcus aureus, Klebsiella pneumoniae, Acinetobacter baumannii, Pseudomonas aeruginosa,* and *Enterobacter* species) ("ESKAPE") pathogens. The methods described herein can be easily and cheaply adapted to new microorganism species strains and diagnostic tests.

In some embodiments, the method provides for determining antimicrobial susceptibility of a microorganism by introducing a suspension of microorganisms to a cartridge comprising a plurality of chambers comprising an antimicrobial; incubating the cartridge under conditions promoting microorganism growth for an initial time period; performing a checkpoint assay to determine if the relative microorganism concentration has reached a threshold value; and performing a plurality of different growth assays to determine the microorganism's susceptibility to the antimicrobial.

In some embodiments, the methods described herein are performed in an automated platform for antimicrobial susceptibility testing.

AST methods can perform assays that can be useful for determining MICs or QSRs in certain bacterial strains. Instances occur where one type of assay is more effective for particular strains of microorganisms over others in determining the microorganism's susceptibility to an antimicrobial. The methods described herein provide for a way to determine which of the plurality of different assays, if any, can be appropriate for determining a microorganism's susceptibility to an antimicrobial. In some embodiments, the method uses a different assay for a different antimicrobial-antibiotic combination.

Each growth assay can be selected from a group of endpoint assays such as a metabolic probe assay, a surface-binding probe assay, a chemical probe assay, a biochemical probe assay, an ATP assay, a nucleic acid probe assay, a double-stranded nucleic acid probe assay, an optical density assay, measurement for microorganism mass, a visual assay, or a pH molecular probe assay.

The plurality of different assays can be performed in parallel, where the growth assay (e.g., an endpoint assay) provides a determination of antimicrobial susceptibility for a given microorganism. The AST method can be run on a cartridge as described above. In some embodiments, the plurality of different assays is performed in different cartridge chambers. In some embodiments, the same assay is performed in a particular row or column of chambers on a cartridge.

In some embodiments, a plurality of different assays run in parallel means that the assays share an incubation period for microorganism growth. In some embodiments, the assays run in parallel are performed sequentially. In some embodiments, the assays run in parallel are performed in the same cartridge chamber. In some embodiments, the assays run in parallel overlap.

In some embodiments, this disclosure provides for performing a metabolic probe assay and a surface-binding probe assay in order to enable accurate rapid determination of a microorganism's susceptibility to an antimicrobial in less than 3, 3.5, 4, 4.5, 5, 5.5, 6, 6.5, 7, 7.5, or 8 hours, as compared to the Clinical Laboratory Standards Institute (CLSI) overnight reference method. In some embodiments, the metabolic probe assay is performed before the surface-binding probe assay. Cumulatively, data from these two assays can enable accurate determination of the antimicrobial's MICs; thus, in some embodiments, this disclosure, in a greatly reduced amount of time relative to standard methods, provides a patient with an appropriate treatment regimen, e.g., a specific antimicrobial and at a particular dosage.

The metabolic probe assay can utilize a metabolic probe that is present in an aqueous-miscible solvent. Thus, in some embodiments, the introduction of the metabolic probe does not result in an emulsion. Introducing a probe in an emulsion can be inconvenient in small chambers and can lead to inconsistent results. In some embodiments, the metabolic probe is hydrophilic or substantially hydrophilic. In some embodiments, the metabolic probe assay uses a metabolic probe that is a redox active probe. Non-limiting examples of redox active probes that can be introduced during the metabolic probe assay can include 7-hydroxy-10-oxidophenoxazin-10-ium-3-one (resazurin), 3-(4,5-dimethylthiazol-2-yl)-2,5-diphenyltetrazolium bromide (MTT), 3-(4,5-dimethylthiazol-2-yl)-5-(3-carboxymethoxyphenyl)-2-(4-sulfophenyl)-2H-tetrazolium (MTS), 3,3'-(3,3'-Dimethoxy-4,4'-biphenylene)bis[2,5-bis(p-nitrophenyl)-2H-tetrazolium chloride] (TNBT), 2,3-bis-(2-methoxy-4-nitro-5-sulfophenyl)-2H-tetrazolium-5-carboxanilide (XTT), water-soluble tetrazolium salts (WSTs), (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), 2,2'-Dibenzothiazolyl-5,5'-bis[4-di(2-sulfoethyl)carbamoylphenyl]-3,3'-(3,3'-dimethoxy 4,4'-biphenylene)ditetrazolium, disodium salt (WST-5), 5-(2,4-disulfophenyl)-3-(2-methoxy-4-nitrophenyl)-2-(4-nitrophenyl)-2H-tetrazolium, inner salt, monosodium salt (WST-8), 2,3,5-triphenyl-tetrazolium chloride (TTC), 5-cyano-2,3-di(p-tolyl)tetrazolium chloride (CTC), 3,3'(3,3'-dimethoxy-[1,1'-biphenyl]-4,4'-diyl)bis(2-(4-nitrophenyl)-5-phenyl-2H-tetrazol-3-ium)(DBNPT), 3-(naphthalen-1-yl)-2,5-diphenyl-2H-tetrazol-3-ium (NDT), Thiazolyl Blue Tetrazolium Bromide (TBTB), 2-(4-Iodophenyl)-3-(4-nitrophenyl)-5-phenyl-2H-tetrazolium chloride (INT), phenazine methyl sulfate (PMS), phenazine ethyl sulfate (PES), glycylphenylalanyl-aminofluorocoumarin (GF-AFC), 2,2'-bis(4-Nitrophenyl)-5,5'-diphenyl-3,3'-(3,3'-dimethoxy-4,4'-diphenylene)ditetrazolium chloride (NBT), 2,5-Diphenyl-3-(1-naphthyl)tetrazolium chloride (TV), 3,3'-(3,3'-Dimethoxy[1,1'-biphenyl]-4,4'-diyl)-bis(2,5-diphenyl-2H-tetrazolium) dichloride (BTC), 5-Cyano-2,3-bis(4-methylphenyl)-2H-tetrazolium chloride (CTC), 2,3-Bis(2-methoxy-4-nitro-5-sulfophenyl)-2H-tetrazolium-5-carboxanilide inner salt (XTT), RealTime-Glo™, Caspase-Glo®, acetoxymethyl ester of BATDA, ferrocene, dodecylresazurin, dihydrorhodamine 123, dihydrofluorescein, 6-carboxy-2',7'-dichlorodihydro fluorescein diacetate and its acetoxymethyl ester, 2',7'-dichlorodihydrofluorescein diacetate, 5-carboxy-2',7'-dichlorodihydrofluorescein diacetate and its acetoxymethyl ester, chloromethyl-2',7'-dichlorodihydrofluorescein diacetate acetyl ester, dihydrocalcein AM, dihydroethidium, luminol, or 2,3,4,5,6-pentafuorotetramethyldihydrorosamine.

In some embodiments, suitable metabolic probes are well known to those skilled in the art and are described in *The Molecular Probes® Handbook: A Guide to Fluorescent Probes and Labeling Technologies,* $11^{th}$ Ed. (2010) (see, e.g., Chapter 15, "Assays for Cell Viability, Proliferation and Function") and Riss T L, Moravec R A, Niles A L, et al. Cell Viability Assays. 2013 May 1 [Updated 2016 Jul. 1]. In: Sittampalam G S, Coussens N P, Nelson H, et al., editors. Assay Guidance Manual [Internet]. Bethesda (MD): Eli Lilly & Company and the National Center for Advancing Translational Sciences; 2004-. and U.S. Pat. No. 7,897,331, which are herein incorporated by reference in their entirety.

In some embodiments, the metabolic probes used are described in US Patent Application No. 2020-0149086 at paragraphs [0213] through [0237].

Checkpoint assays can be performed to ascertain microorganism growth. For example, in order to obtain accurate AST determinations, the assay can account for slow-growing strains of bacteria, and thus, the methods herein can provide for a checkpoint assay that occurs after an initial incubation period in order to ascertain whether sufficient microorganism growth has occurred. Growth, as in growth of microorganisms, can include a proliferation in number, an increase in length, an increase in volume, and/or an increase in nucleic acid and/or protein content of the microorganisms.

Although various endpoint measurements, such as ATP, DNA, RNA and surface-binding measurements, have previously been shown to be applicable to AST determinations, these assays have failed to date commercially due to their inability to account for slow-growing strains of microorganisms, such as the vancomycin-intermediate *Staphylococcus aureus* that can have significantly slower growth kinetics than other *S. aureus* strains, including methicillin-resistant and methicillin-susceptible strains.

Although various endpoint measurements, such as ATP, DNA, RNA and surface-binding measurements, have previously been shown to be applicable to AST determinations, these assays have failed to date commercially due to their inability to account for slow-growing strains of microorganisms, such as the vancomycin-intermediate *Staphylococcus aureus* that can have significantly slower growth kinetics than other *S. aureus* strains, including methicillin-resistant and methicillin-susceptible strains.

Although various endpoint measurements, such as ATP, DNA, RNA and surface-binding measurements, have previously been shown to be applicable to AST determinations, these assays have failed to date commercially due to their inability to account for slow-growing strains of microorganisms, such as the vancomycin-intermediate *Staphylococcus aureus* that can have significantly slower growth kinetics than other *S. aureus* strains, including methicillin-resistant and methicillin-susceptible strains.

Conventional AST methods can be performed on automated instruments that utilize a broth microdilution procedure in a microplate, where a growth indicator is included in the broth during inoculation and incubation in order to determine AST results by measuring indicator signals with respect to time. It was found, however, that these growth indicators, such as resazurin, can, in fact, be harmful to the microorganisms when they are added during the incubation period.

Although some growth indicators can suppress microbial growth, they can serve as a proxy for uninhibited growth through their incorporation in a growth threshold checkpoint well during microbial incubation. In order to address the slow-growing bacteria limitation, a checkpoint assay using a growth indicator can be first performed to measure that sufficient microorganism growth has reached a threshold, and then a final measurement of relative microorganism concentrations can be performed in separate wells to determine AST results (e.g. MIC or QSR). If the checkpoint assay shows that the microorganism growth has failed to reach the threshold, the microplate can be allowed to incubate for a further period of time and does not commence to the final measurement of relative microorganism concentrations until the growth threshold has been reached. In some embodiments, the additional incubation time period is performed between 1 and 20 hours, between 2 and 20 hours, between 3 and 20 hours, between 4 and 20 hours, between 5 and 20 hours, between 6 and 20 hours, between 8 and 20 hours, between 9 and 20 hours, between 10 and 20 hours, between 11 and 20 hours, between 12 and 20 hours, between 13 and 20 hours, between 14 and 20 hours, between 15 and 20 hours, between 16 and 20 hours, between 17 and 20 hours, between 18 and 20 hours, or between 19 and 20 hours. In some embodiments, the incubation period is between 2 and 19 hours, or between 3 and 18 hours, between 4 and 16 hours, between 3 and 14 hours, 3 and 12 hours or every possible time intervals in between.

In some embodiments, the threshold value is a ratio between a positive control and a background control. In some embodiments, the positive control comprises a suspension of microorganisms and a growth indicator incubated without an antimicrobial. In some embodiments, the background control comprises a medium and a growth indicator incubated without microorganisms. In some embodiments, a signal to noise ratio is measured by determining a ratio of a growth indicator such as alamar blue signal in an inoculated versus an uninoculated well. In certain embodiments, the ratio of the positive control to the background control is 1.1, 1.2, 1.3, 1.4, 1.5, 1.6, 1.7, 1.8, 1.9, 2.0, 2.1, 2.2, 2.3, 2.4, 2.5, or greater. In some embodiments, the signal to noise ratio is measured by determining the signal from a surface binding agent in an inoculated versus uninoculated well.

In some embodiments, the wells of the microplate used for these checkpoint assays do not comprise antimicrobials, nor are they utilized for the final measurements to determine an antimicrobial's efficacy. In certain embodiments, the checkpoint assay is performed in a chamber without an antimicrobial. In some embodiments, the checkpoint assay is performed in a chamber without one or more microorganisms. In some embodiments, the checkpoint assay is performed in a chamber with one or more antimicrobials of known efficacy against the microorganism.

When the threshold checkpoint assays indicate sufficient growth to initiate the AST growth assay, a plurality of different assays can be performed. AST growth assays, as previously discussed, can be utilized, such as assays for ATP, such as BacTiter-Glo®, RealTime-Glo™, Caspase-Glo®; DNA stains, such as ethidium bromide, propidium iodide, SYTOX green, phenanthridines, acridines, indoles, imidazoles, and cyanine, including TOTO, TO-PRO, SYTO; and binding assays, such as enzyme-linked immunosorbent assays, antibody assays, lectin-based assays, polymyxin B-based assays, and chemical probe-based assays.

In some embodiments, the checkpoint assay comprises nucleic acid amplification or nucleic acid sequencing. In some embodiments, the checkpoint assay comprises microscopy or mass spectrometry. In some embodiments, the checkpoint assay comprises measuring microorganism mass.

EXAMPLES

Example 1. Metabolic Dye

A metabolic (viability) dye formulation was made according to the following:
- 62.5 mg Potassium Hexacyanoferrate (III; Sigma)
- 80 mg Potassium Hexacyanoferrate (II; Sigma)
- 110 mg Resazurin Sodium Salt (Sigma)
- 320 µg Methylene Blue (Sigma; 100 mL of 0.32 mg Methylene Blue/100 mL distilled $H_2O$ solution was used)
- 900 mL distilled $H_2O$

Example 2. HMLR Testing

Figures 2A, 2B:
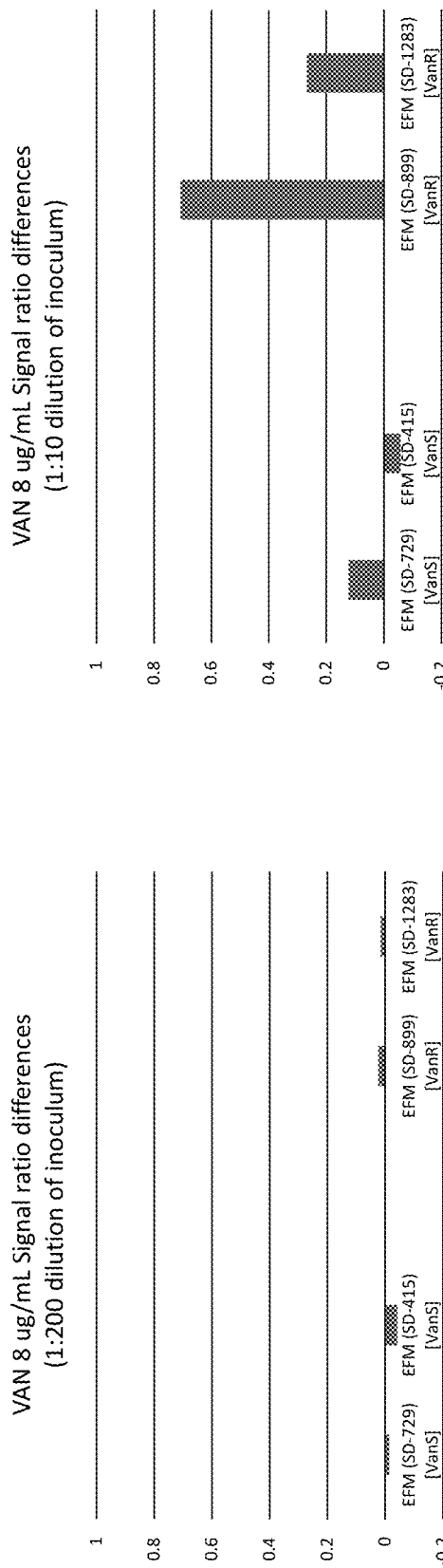
FIGS. 2A and 2B. Depiction of the difference of the ratios of signal in wells containing vancomycin to uninoculated control wells at 4 and 3 hours following inoculation for larger organism inoculum concentrations.

HMLR testing was performed as follows. Bacteria were prepared by diluting colonies in saline to obtain a 0.5 McFarland, which was measured using a spectrophotometer (Den1B). The suspensions were then inoculated into 96-well plates which contained cation-adjusted Mueller Hinton broth (MHB; BD Diagnostics) and an 8 µg/mL concentration of vancomycin (Sigma) to achieve a 1:10 or a 1:200 final dilution of the McFarland suspension. A 1:200 final dilution of the McFarland suspension is the dilution commonly used for broth microdilution AST testing, thus the 1:10 dilution represents a 20-fold concentration higher than this standard. 10 µL of Metabolic Dye containing resazurin was added to every well and the plates were incubated at 35° C. for 3 hours, shaking at 150 rpm. After incubation, fluorescence was read for every well at Ex: 560 nm/Em: 590 nm. The plates were incubated at 35° C. for one more hour with shaking at 150 rpm and the fluorescence read was repeated. Data graphed in FIG. 1 is the difference of the ratios of fluorescent signal in wells containing vancomycin to uninoculated control wells at 4 and 3 hours following inoculation. Organisms resistant to vancomycin have larger changes in signal ratios from 3 to 4 hours than sensitive organisms. Additionally, the data in FIGS. 2-3 suggest the differences between these ratios are more pronounced for larger organism inoculum concentrations.

Example 3. Vancomycin Resistance Determination

Bacteria were prepared by diluting colonies in saline to obtain a 0.5 McFarland, which was measured using a calibrated spectrophotometer. Suspensions were then diluted into cation-adjusted Mueller Hinton Broth (MHB) and inoculated into 384-well plates that contained dried-down antimicrobials, including doubling concentrations of vancomycin across multiple series. The diluted suspensions were added to achieve 1:200 or 1:5 final dilutions of the McFarland suspensions for vancomycin and supplemental vancomycin tests, respectively. 5 µL of Metabolic Dye, containing 11.1M Methylene Blue, 0.438 mM Resazurin Sodium Salt, 0.190 mM Potassium Hexacyanoferrate (III), and 0.190 mM Potassium Hexacyanoferrate (II) Trihydrate in deionized water was added to all test wells. Plates were then incubated at 35° C. for 3 hours, shaking at 150 rpm. After incubation, fluorescence was read for all wells at Ex: 560 nm/Em: 590 nm (Viability).

The reagents used in the subsequent steps are comprised as follows: Selux Blast Buffer, containing 1.65 mM Cetrimonium Bromide in a solution of 0.5% n-Hexanol by volume in deionized water. Selux Binding Dye, containing 8.92 mM Tween 20, 136.9 mM Sodium Chloride, 2.68 mM Potassium Chloride, 10.14 mM Sodium Phosphate Dibasic, 1.76 mM Potassium Phosphate Monobasic, 556.3 nM Europium Cryptate Diamine, and 0.05% DMSO by volume in deionized water. Selux Wash Buffer, containing 0.446 mM Tween 20, 136.9 mM Sodium Chloride, 2.68 mM Potassium Chloride, 10.14 mM Sodium Phosphate Dibasic, and 1.76 mM Potassium Phosphate Monobasic in deionized water. These reagents were then added to all test wells in a series of operations, each followed by a 5-minute shaking step at 150 rpm, centrifugation at 2500 rpm for 150 seconds, and aspiration of the supernatant in the wells. First, 50 µL of Selux Blast buffer was added to all wells. Next, 50 µL of Selux Binding Dye was added to all test wells. Next, 50 µL of Selux Wash Buffer was added to all test wells. After this third aspiration step was completed, 50 µL of Selux Wash Buffer was added to all wells, and fluorescence was read for all wells at Ex: 330 nm/Em: 615 nm (Surface Area). Plotted data outlines normalized viability and surface area signals in standard vancomycin test wells, as well as surface area signal of supplemental vancomycin test wells as normalized to positive control signal.

CONCLUSION

While the foregoing description and drawings represent various embodiments, it will be understood that various additions, modifications, and substitutions may be made therein without departing from the spirit and scope of the present disclosure. In particular, it will be clear to those skilled in the art that principles of the present disclosure may be embodied in other forms, structures, arrangements, proportions, compositions or processes and with other elements, materials, steps and components, without departing from the spirit or essential characteristics thereof. One skilled in the art will appreciate that the disclosure may be used with many modifications of structure, arrangement, order, proportions, materials, and components and otherwise, used in the practice of the disclosure, which are particularly adapted to specific environments and operative requirements without departing from the principles of the present disclosure. The presently disclosed embodiments are therefore to be considered in all respects as illustrative and not restrictive, the scope of the invention being indicated by the appended claims, and not limited to the foregoing description.

What is claimed is:

1. A method for determining a qualitative susceptibility result of an antimicrobial for a microorganism-comprising sample, the method comprising:
   inoculating a plurality of panels comprising a plurality of reservoirs comprising one or more dilution series reservoirs, one or more high microorganism load reservoirs (HMLRs), and one or more control reservoirs, wherein
   a microorganism is present at a first concentration $C_{m0}$ in the one or more dilution series reservoirs comprising an antimicrobial A that extends from a low concentration of antimicrobial ($C_{AL}$) that is at or below a susceptible breakpoint to a high concentration of antimicrobial ($C_{AH}$) that is at or above a resistant breakpoint;
   the microorganism is present at a second concentration $\geq 2 \times C_{m0}$ in the one or more HMLRs comprising the antimicrobial A at a third concentration $\geq C_{AL}/4$; and
   the microorganism is not present in one or more control reservoirs comprising the antimicrobial A;
   incubating the plurality of panels under conditions promoting microorganism growth;
   measuring a relative growth in the one or more dilutions series reservoirs, the one or more HMLRs, and the one or more control reservoirs; and
   determining a qualitative susceptibility interpretations from the relative growth measurements.

2. The method of claim 1, wherein growth in the reservoirs is determined following addition of a metabolic viability probe comprising resazurin and methylene blue, ferrous and ferric potassium salts, or 1-methoxy-5-methlyphenasinum methyl sulfate.

3. The method of claim 2, wherein growth in the reservoirs is determined by time-resolved fluorescence or time-gated luminescence.

4. The method of claim 2, wherein growth in the reservoirs is determined following the addition of a probe capable of binding microbial surfaces.

5. The method of claim 1, wherein the first concentration $C_{m0}$ is between $1 \times 10^5$ and $5 \times 10^6$ CFU/mL.

6. The method of claim 1, wherein the step of determining the qualitative susceptibility interpretations comprises a viability assay where a probe is added following a growth threshold being achieved and a surface area assay following the viability assay, wherein the surface area assay comprises:
   incubating a liquid suspension of the microorganism in the presence of the antimicrobial A under conditions that promote growth of the microorganism;
   adding a signaling agent configured to bind to a surface of the microorganism;
   separating the microorganism bound by the signaling agent from unbound signaling agent; and
   measuring one or more signal levels associated with the microorganism as compared to one or more controls, thereby measuring the antimicrobial susceptibility of the microorganism;
   wherein the signaling agent comprises a linker group L, and an amplifier group comprising an Europium coordination complex; and wherein,
   the linker group L forms a covalent bond to the amplifier group; or
   the linker group L forms one or more non-covalent interactions with the amplifier group.

7. The method of claim 1, wherein the one or more HMLRs comprise the antimicrobial A at a fourth concentration $\geq C_{AL}$.

8. The method of claim 1, wherein the one or more HMLRs comprise a fourth microorganism concentration $\geq 3 \times C_{m0}$, $\geq 4 \times C_{m0}$, $\geq 5 \times C_{m0}$, $\geq 6 \times C_{m0}$, $\geq 7 \times C_{m0}$, $\geq 8 \times C_{m0}$, $\geq 9 \times C_{m0}$, $\geq 10 \times C_{m0}$, $\geq 11 \times C_{m0}$, $\geq 12 \times C_{m0}$, $\geq 13 \times C_{m0}$, $\geq 14 \times C_{m0}$, $\geq 15 \times C_{m0}$, $\geq 16 \times C_{m0}$, $\geq 17 \times C_{m0}$, $\geq 18 \times C_{m0}$, $\geq 19 \times C_{m0}$, $\geq 20 \times C_{m0}$.

9. The method of claim 1, wherein the antimicrobial A is one or more of, but not limited to, the following: Amikacin, Amikacin-fosfomycin, Amoxicillin, Amoxicillin-clavulanate, Ampicillin, Ampicillin-sulbactam, Azithromycin, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Voriconazole and a salt or hydrate form thereof.

10. The method of claim 1, wherein the method further comprises performing one or more first checkpoint assays to determine if microorganism growth has achieved a threshold value; and
  (a) if the threshold value is achieved, performing at least one secondary assay to measure a relative growth in the dilution series reservoirs and the one or more HMLRs, and based upon said measuring of the relative growth, determining the qualitative susceptibility result (QSR) and obtaining a minimum inhibitory concentration (MIC); or
  (b) if the threshold value is not achieved, performing one or more additional incubation periods under conditions promoting microorganism growth until
    (i) the threshold value is achieved, and thereafter performing step (a); or
    (ii) a maximum of 18 hours has transpired without the threshold value being achieved and no further assays are performed.

11. The method of claim 10, wherein the at least one of the one or more first checkpoint assays and the secondary assay is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay, wherein the metabolic probe comprises 7-hydroxy-10-oxidophenoxazin-10-ium-3-one (resazurin).

12. The method of claim 10, wherein at least one well of the plurality of panels is a second checkpoint assay well comprising a growth indicator during the initial incubation period or the additional incubation period, wherein the growth indicator comprises resazurin.

13. The method of claim 1, wherein the dilution series comprises at least three reservoirs comprising different antimicrobial concentrations.

14. A method for determining a qualitative susceptibility result of an antimicrobial for a microorganism-comprising sample, the method comprising:
  inoculating a plurality of panels comprising a first plurality of reservoirs comprising one or more dilution series reservoirs, one or more high microorganism load reservoirs (HMLRs), and one or more control reservoirs, wherein
    a microorganism is present at first concentration $C_{m0}$ in the dilution series reservoirs of an antimicrobial A that extends from a low concentration of antimicrobial ($C_{AL}$) that is at or below a susceptible breakpoint to a high concentration of antimicrobial ($C_{AH}$) that is at or above a resistant breakpoint;
    the microorganism is present at a second concentration $\geq 2 \times C_{m0}$ in one or more HMLRs comprising antimicrobial A at a third concentration $\geq C_{AL}/4$; and
    the microorganism is not present in the one or more control reservoirs comprising the antimicrobial A;
  incubating the plurality of panels under conditions promoting microorganism growth;
  measuring relative growth in the dilutions series reservoirs, the one or more HMLRs, and the one or more control reservoirs determined by time-resolved fluorescence or time-gated luminescence; and
  determining the qualitative susceptibility interpretations from the relative growth measurements.

15. The method of claim 14, wherein growth in the reservoirs is determined following addition of a metabolic viability probe comprising resazurin and methylene blue, ferrous and ferric potassium salts, or 1-methoxy-5-methlyphenasinum methyl sulfate.

16. The method of claim 14, wherein growth in the reservoirs is determined following the addition of a probe capable of binding microbial surfaces.

17. The method of claim 14, wherein the first concentration $C_{m0}$ is between $1 \times 10^5$ and $5 \times 10^6$ CFU/mL.

18. The method of claim 14, wherein the step of determining the qualitative susceptibility interpretations comprises a viability assay where a probe is added following a growth threshold being achieved and a surface area assay following the viability assay, wherein the surface area assay comprises:
  incubating a liquid suspension of the microorganism in the presence of the antimicrobial A under conditions that promote growth of the microorganism;
  adding a signaling agent that binds to a surface of the microorganism;
  separating the microorganism bound by the signaling agent from unbound signaling agent; and
  measuring signal levels associated with the microorganism as compared to one or more controls, thereby measuring the antimicrobial susceptibility of the microorganism;
  wherein the signaling agent comprises a linker group L, and an amplifier group comprising an Europium coordination complex; and wherein,
  the linker group L forms a covalent bond to the amplifier group; or the linker group L forms one or more non-covalent interactions with the amplifier group.

19. The method of claim 1, wherein the one or more HMLRs comprises the antimicrobial A at a concentration $\geq C_{AL}$.

* * * * *